(12) United States Patent
Heppner et al.

(10) Patent No.: US 6,989,389 B2
(45) Date of Patent: Jan. 24, 2006

(54) ARYL ETHER SUBSTITUTED IMIDAZOQUINOLINES

(75) Inventors: Philip D. Heppner, Woodbury, MN (US); Leslie J. Charles, Hudson, WI (US); Joseph F. Dellaria, Woodbury, MN (US); Bryon A. Merrill, River Falls, WI (US); John W. Mickelson, Mattawan, MI (US)

(73) Assignee: 3M Innovative Properties Co., St. Paul, MN (US)

( * ) Notice: Subject to any disclaimer, the term of this patent is extended or adjusted under 35 U.S.C. 154(b) by 113 days.

(21) Appl. No.: 10/696,108

(22) Filed: Oct. 29, 2003

(65) Prior Publication Data

US 2004/0138248 A1 Jul. 15, 2004

Related U.S. Application Data

(63) Continuation of application No. 10/165,750, filed on Jun. 7, 2002, now Pat. No. 6,677,348, which is a continuation-in-part of application No. 10/013,202, filed on Dec. 6, 2001, now Pat. No. 6,670,372.

(60) Provisional application No. 60/254,218, filed on Dec. 8, 2000.

(51) Int. Cl.
*A61K 31/4745* (2006.01)
*C07D 471/04* (2006.01)
*A61P 37/02* (2006.01)
*A61P 31/12* (2006.01)

(52) U.S. Cl. .................. 514/293; 546/82; 546/84; 546/159

(58) Field of Classification Search .................. 514/293; 546/82, 84, 159
See application file for complete search history.

(56) References Cited

U.S. PATENT DOCUMENTS

| | | | |
|---|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster et al. |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,693,811 A | 12/1997 | Lindstrom |
| 5,741,908 A | 4/1998 | Gerster et al. |
| 5,756,747 A | 5/1998 | Gerster et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,451,810 B1 | 9/2002 | Coleman et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,656,938 B2 | 12/2003 | Crooks et al. |
| 6,660,735 B2 | 12/2003 | Crooks et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 2002/0055517 A1 | 5/2002 | Smith |
| 2002/0058674 A1 | 5/2002 | Hedenstrom et al. |

FOREIGN PATENT DOCUMENTS

| | | |
|---|---|---|
| EP | 0 394 026 | 10/1990 |
| EP | 1 104 764 | 6/2001 |
| JP | 9-255926 | 3/1999 |
| JP | 11-222432 | 8/1999 |
| JP | 2000-247884 | 9/2000 |
| WO | 9-208584 | 8/1997 |
| WO | WO 01/74343 | 10/2001 |
| WO | WO 02/36592 | 5/2002 |
| WO | WO 02/46188 | 6/2002 |
| WO | WO 02/46189 | 6/2002 |
| WO | WO 02/46190 | 6/2002 |
| WO | WO 02/46193 | 6/2002 |
| WO | WO 02/46749 | 6/2002 |
| WO | WO 02/102377 | 12/2002 |
| WO | WO 03/020889 | 3/2003 |
| WO | WO 03/043572 | 5/2003 |
| WO | WO 03/045391 | 6/2003 |

OTHER PUBLICATIONS

Sof'ina et al. Experimental Evaluation of Antitumor Drugs in the USA and USSR and Clinical Correlations. NCI Monograph 55. NIH Publication No. 80–1933 (1980), pp. 76–78.*

(Continued)

*Primary Examiner*—Evelyn Mei Huang
(74) *Attorney, Agent, or Firm*—Dean A. Ersfeld

(57) ABSTRACT

Imidazoquinoline and tetrahydroimidazoquinoline compounds that contain ether and aryl or alkenyl functionality at the 1-position are useful as immune response modifiers. The compounds and compositions of the invention can induce the biosynthesis of various cytokines and are useful in the treatment of a variety of conditions including viral diseases and neoplastic diseases.

1 Claim, No Drawings

OTHER PUBLICATIONS

Strandtmann et al. J. Med. Chem. (1967), 10(6):1063–1065.*

Wozniak, et al, "The Amination of 3–nitro–1, 5–naphthyridines by Liquid Ammonia/Potassium Permanganate[1,2]. A New and Convenient Amination Method.", *Journal of the Royal Netherlands Chemical Society*, 102, pp 511–513, Dec. 12, 1983.

Brennan, et al, "Automated Bioassay of Interferons in Micro–test Plates", *Biotechniques*, Jun./Jul., 78, 1983.

Testerman, et al., "Cytokine Induction by the Immunomodulators Imiquimod and S–27609", *Journal of Leukocyte Biology*, vol. 58, pp. 365–372, Sep. 1995.

Bachman, et al, "Synthesis of Substituted Quinolylamines. Derivatives of 4–Amino–7–Chloroquinoline", *J. Org. Chem*, 15, pp 1278–1284 (1950).

Jain, et al, "Chemical and Pharmacological Investigations of Some ω–Substituted Alkylamino–3–aminopyridines", *J. Med. Chem.*, 11, pp 87–92 (1968).

Baranov, et al., *Chem. Abs.* 85, 94362, (1976).

Berényi, et al, "Ring Transformation of Condensed Dihydro–as–triazines", *J. Heterocyclic Chem.*, 18, pp 1537–1540 (1981).

Chollet, et al, "Development of a Topically Active Imiquimod Formulation", *Pharmaceutical Development and Technology*, 4(1), pp 35–43 (1999).

Izumi, et al., "1H–Imidazo[4,5–c]quinoline Derivatives as Novel Potent TNF–αSuppressors: Synthesis and Structure–Activity Relationship of 1–,2– and 4–Substituted 1H–imidazo[4,5–c]pyridines", *Bioorganic & Medicinal Chemistry*, 11, pp 2541–2550 (2003).

Sidky etal., "Inhibition of Murine Tumor Growth by an Interferon–inducing Imidazoquinolinamine", *Cancer Research*, 52, 3528–3533, Jul. 1, 1992.

R.L. Miller et al., "Imiquimod applied topically: a novel immune response modifier and new class of drug", *International Journal of Immunopharmacology*, 21, 1–14 (1999).

Karl R. Beutner, MD, et al., "Therapeutic response of basal cell carcinoma to the immune response modifier imiquimod 5% cream,", *J. Am. Acad. Dermatol.*, vol. 41, No. 6, 1002–1007 (Dec. 1999).

Davis et al., "Self–Administered Topical Imiquimod Treatment of Vulvar Intraepithelial Neoplasia", *Journal of Reproductive Medicine*, vol. 45, No. 8, 619–623, (Aug. 2000).

Alexander Steinmann et al., "Topical Imiquimod Treatment of a Cutaneous Melanoma Metastasis", *J.Am.Acad. Dermatol.*, Letters, 555–556 (Sep. 2000).

* cited by examiner

ARYL ETHER SUBSTITUTED IMIDAZOQUINOLINES

CROSS REFERENCE TO RELATED APPLICATIONS

This application is a continuation of U.S. application Ser. No. 10/165,750, filed Jun. 7, 2002, now U.S. Pat. No. 6,677,348, which is a continuation-in-part of U.S. application Ser. No. 10/013,202, filed Dec. 6, 2001, now U.S. Pat. No. 6,670,372, which claims the benefit of U.S. Provisional Application No. 60/254,218, flied Dec. 8, 2000.

FIELD OF THE INVENTION

This invention relates to imidazoquinoline compounds that have a 1-substituent that contains ether and aryl or alkenyl functionality, and to pharmaceutical compositions containing such compounds. A further aspect of this invention relates to the use of these compounds as immunomodulators, for inducing cytokine biosynthesis in animals, and in the treatment of diseases, including viral and neoplastic diseases.

BACKGROUND OF THE INVENTION

The first reliable report on the 1H-imidazo[4,5-c] quinoline ring system, Backman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines were reported. For example, Jain et al., *J. Med. Chem.* 11, pp. 87–92 (1968), synthesized the compound 1-[2-(4-piperidyl) ethyl]-1H-imidazo[4,5-c]quinoline as a possible anticonvulsant and cardiovascular agent. Also, Baranov et al., *Chem. Abs.* 85, 94362 (1976), have reported several 2-oxoimidazo [4,5-c]quinolines, and Berenyi et al., *J. Heterocyclic Chem.* 18, 1537–1540 (1981), have reported certain 2-oxoimidazo [4,5-c]quinolines.

Certain 1H-imidazo[4,5-c]quinolin-4-amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640, all of which are incorporated herein by reference.

There continues to be interest in the imidazoquinoline ring system. Certain 1H-imidazo[4,5-c]naphthyridine-4-amines, 1H-imidazo[4,5-c]pyridin-4-amines, and 1H-imidazo[4,5-c]quinolin-4-amines having an ether containing substituent at the 1 position are known. These are described in U.S. Pat. Nos. 5,268,376; 5,389,640; 5,494,916; and WO 99/29693.

There is a continuing need for compounds that have the ability to modulate the immune response, by induction of cytokine biosynthesis or other mechanisms.

SUMMARY OF THE INVENTION

We have found a new class of compounds that are useful in inducing cytokine biosynthesis in animals. Accordingly, this invention provides imidazo[4,5-c]quinoline-4-amine and tetrahydroimidazo[4,5-c]quinoline-4-amine compounds that have an ether containing substituent at the 1-position. The compounds are described by Formulas (I), (II), (III) and (IV), which are defined in more detail infra. These compounds share the general structural formula:

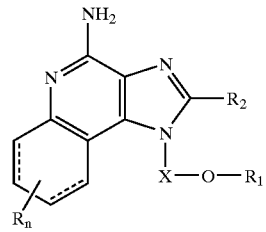

wherein X, $R_1$, $R_2$, and R are as defined herein for each class of compounds having Formulas (I), (II), (III) and (IV).

The compounds of Formulas (I), (II), (III), and (IV) are useful as immune response modifiers due to their ability to induce cytokine biosynthesis and otherwise modulate the immune response when administered to animals. This makes the compounds useful in the treatment of a variety of conditions such as viral diseases and tumors that are responsive to such changes in the immune response.

The invention further provides pharmaceutical compositions containing the immune response modifying compounds, and methods of inducing cytokine biosynthesis in an animal, treating a viral infection in an animal, and/or treating a neoplastic disease in an animal by administering a compound of Formula (I), (II), (III), or (IV) to the animal.

In addition, the invention provides methods of synthesizing the compounds of the invention and intermediates useful in the synthesis of these compounds.

DETAILED DESCRIPTION OF THE INVENTION

As mentioned earlier, we have found certain compounds that induce cytokine biosynthesis and modify the immune response in animals. Such compounds are represented by Formulas (I), (II), (III), and (IV), as shown below.

Imidazoquinoline compounds of the invention, which have ether and aryl or alkenyl functionality at the 1-position are represented by Formula (I):

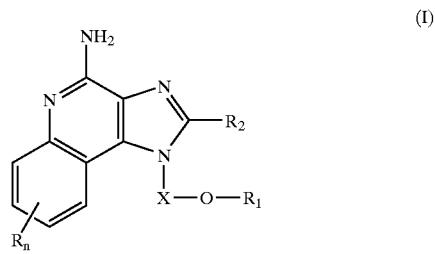

(I)

wherein: X is —$CHR_3$—, —$CHR_3$-alkyl-, or —$CHR_3$-alkenyl-;

$R_1$ is selected from the group consisting of:
-alkenyl;
-aryl;
—$R_4$-aryl;

$R_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;

-alkyl-Y-aryl; and
-alkyl or alkenyl substituted by one or more substituents selected from the group consisting of:
—OH;
-halogen;
—N($R_3$)$_2$;
—CO—N($R_3$)$_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;

$R_4$ is alkyl or alkenyl, both of which may be interrupted by one or more —O— groups;

each $R_3$ is independently H or $C_{1-10}$ alkyl;

each Y is independently —O— or —S(O)$_{0-2}$—;

n is 0 to 4; and each R present is independently selected from the group consisting of $C_{1-10}$ alkyl, $C_{1-10}$ alkoxy, hydroxy, halogen and trifluoromethyl;

or a pharmaceutically acceptable salt thereof.

The invention also provides imidazoquinoline compounds that contain ether functionality at the 1-position, where the ether containing substituent also contains an alkynyl group. These compounds are represented by structural Formula (II):

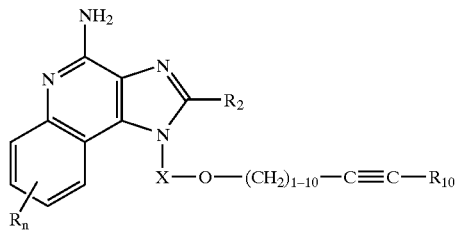

(II)

wherein X is —CHR$_3$—, —CHR$_3$-alkyl-, or —CHR$_3$-alkenyl-;

$R_{10}$ is selected from the group consisting of:
—H;
-alkyl;
-alkylaryl;
-alkenyl; and
-aryl;

$R_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—N($R_3$)$_2$;
—CO—N($R_3$)$_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;

n is 0 to 4;

each Y is independently —O— or —S(O)$_{0-2}$—;

each $R_3$ is independently H or $C_{1-10}$ alkyl; and each R present is independently selected from the group consisting of $C_{1-10}$ alkyl, $C_{1-10}$ alkoxy, hydroxy, halogen and trifluoromethyl;

or a pharmaceutically acceptable salt thereof.

The invention also includes tetrahydroimidazoquinoline compounds that bear an ether and aryl or alkenyl containing substituent at the 1-position. Such tetrahydroimidazoquinoline compounds are represented by Formula (III):

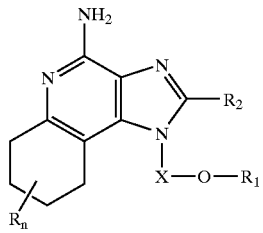

(III)

wherein:

X is —CHR$_3$—, —CHR$_3$-alkyl-, or —CHR$_3$-alkenyl-;

$R_1$ is selected from the group consisting of:
aryl;
alkenyl; and
$R_4$-aryl;

$R_2$ is selected from the group consisting of:
-hydrogen;
-alkyl;
-alkenyl;
-aryl;
-heteroaryl;
-heterocyclyl;
-alkyl-Y-alkyl;
-alkyl-Y-aryl;
-alkyl-Y-alkenyl; and
-alkyl or alkenyl substituted by one or more substituents selected from the group consisting of:
—OH;
-halogen;
—N($R_3$)$_2$;
—CO—N($R_3$)$_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;

$R_4$ is alkyl or alkenyl, both of which may be interrupted by one or more —O— groups;

each $R_3$ is independently H or $C_{1-10}$ alkyl;

each Y is independently —O— or —S(O)$_{0-2}$—;

n is 0 to 4; and each R present is independently selected from the group consisting of $C_{1-10}$ alkyl, $C_{1-10}$ alkoxy, hydroxy, halogen and trifluoromethyl;

or a pharmaceutically acceptable salt thereof.

An additional class of immune response modifying compounds of the invention are tetrahydroimidazoquinoline compounds that have an ether containing substituent at the 1-position, where the ether containing substituent also contains an alkynyl group. These compounds are represented by structural Formula (IV):

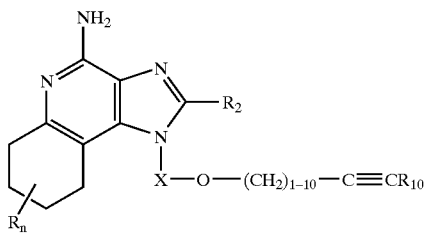

(IV)

wherein

X is —$CHR_3$—, —$CHR_3$-alkyl-, or —$CHR_3$-alkenyl-;

$R_{10}$ is selected from the group consisting of:
  —H;
  -alkyl;
  -alkylaryl;
  -alkenyl; and
  -aryl;

$R_2$ is selected from the group consisting of:
  -hydrogen;
  -alkyl;
  -alkenyl;
  -aryl;
  -heteroaryl;
  -heterocyclyl;
  -alkyl-Y-alkyl;
  -alkyl-Y-aryl;
  -alkyl-Y-alkenyl; and
  -alkyl or alkenyl substituted by one or more substituents selected from the group consisting of:
    —OH;
    -halogen;
    —$N(R_3)_2$;
    —CO—$N(R_3)_2$;
    —CO—$C_{1-10}$ alkyl;
    —CO—O—$C_{1-10}$ alkyl;
    —$N_3$;
    -aryl;
    -heteroaryl;
    -heterocyclyl;
    —CO-aryl; and
    —CO-heteroaryl;

each $R_3$ is independently H or $C_{1-10}$ alkyl;

each Y is independently —O— or —$S(O)_{0-2}$—;

n is 0 to 4; and each R present is independently selected from the group consisting of $C_{1-10}$ alkyl, $C_{1-10}$ alkoxy, hydroxy, halogen and trifluoromethyl;

or a pharmaceutically acceptable salt thereof.

Preparation of the Compounds

Compounds of the invention can be prepared according to Reaction Scheme I where R, $R_2$, X and n are as defined above and $R_{11}$ is alkyl substituted by an aryl group wherein the aryl group may be unsubstituted or may be substituted or $R_{11}$ is substituted aryl with the proviso that if $R_{11}$ is substituted aryl at least one substituent is a strong electron withdrawing group located ortho or para to the ether bond.

Reaction Scheme I

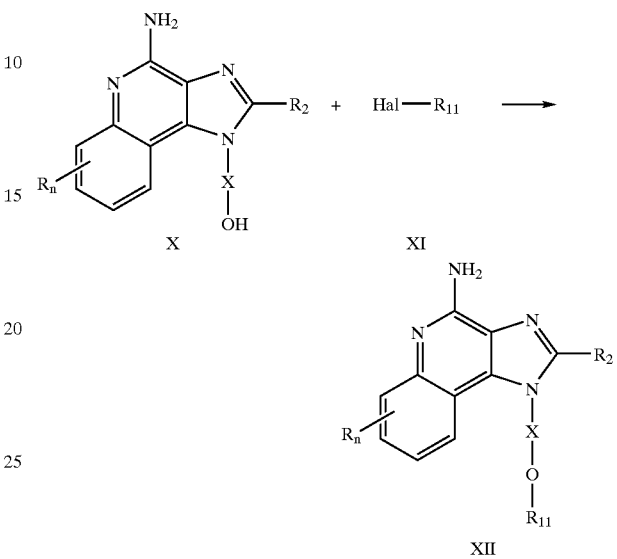

In Reaction Scheme I a 4-amino-1H-imidazo[4,5-c]quinolin-1-yl alcohol of Formula X is alkylated with a halide of Formula XI to provide a 1H-imidazo[4,5-c]quinolin-4-amine of Formula XII which is a subgenus of Formula I. The alcohol of Formula X is reacted with sodium hydride in a suitable solvent such as N,N-dimethylformamide to form an alkoxide. The halide is then added to the reaction mixture. The reaction can be carried out at ambient temperature or with gentle heating (~50° C.) if desired. The product or a pharmaceutically acceptable salt thereof can be isolated using conventional methods.

Many compounds of Formula X are known, see for example Gerster, U.S. Pat. No. 4,689,338 and Gerster et. al., U.S. Pat. No. 5,605,899, the disclosures of which are incorporated by reference herein; others can readily be prepared using known synthetic routes, see for example, Andre et. al, U.S. Pat. No. 5,578,727; Gerster, U.S. Pat. No. 5,175,296; Nikolaides et al., U.S. Pat. No. 5,395,937; and Gerster et. al., U.S. Pat. No. 5,741,908, the disclosures of which are incorporated by reference herein. Many halides of Formula XI are commercially available; others can be readily prepared using known synthetic methods.

Compounds of the invention can be prepared according to Reaction Scheme II where R, $R_2$, $R_{11}$, X and n are as defined above.

In step (1) of Reaction Scheme II a 1H-imidazo[4,5-c]quinolin-1-yl alcohol of Formula XIII is alkylated with a halide of Formula XI to provide a 1H-imidazo[4,5-c]quinolin-1-yl ether of Formula XIV. The alcohol of Formula XIII is reacted with sodium hydride in a suitable solvent such as N,N-dimethylformamide or tetrahydrofuran to form an alkoxide. The alkoxide is then combined with the halide Alternatively, the alcohol and the halide can be combined in a biphasic mixture of aqueous 50% sodium hydroxide and an inert solvent such as dichloromethane in the presence of a phase transfer catalyst such as benzyltrimethylammonium chloride. The reaction can be carried out at ambient temperature. Many compounds of Formula XIII are known, see for example, Gerster, U.S. Pat. No. 4,689,338; others can readily be prepared using known synthetic routes, see for example, Gerster et al., U.S. Pat. No. 5,605,899 and Gerster, U.S. Pat. No. 5,175,296.

In step (2) of Reaction Scheme II a 1H-imidazo[4,5-c] quinolin-1-yl ether of Formula XIV is oxidized to provide a 1H-imidazo[4,5-c]quinoline-5N-oxide of Formula XV using a conventional oxidizing agent capable of forming N-oxides. Preferably a solution of a compound of Formula XIV in a suitable solvent such as chloroform or dichloromethane is oxidized using 3-chloroperoxybenzoic acid at ambient temperature.

In step (3) of Reaction Scheme II a 1H-imidazo[4,5-c] quinoline-5N-oxide of Formula XV is aminated to provide a 1H-imidazo[4,5-c]quinolin-4-amine of Formula XII which is a subgenus of Formula I. Step (3) involves (i) reacting a compound of Formula XV with an acylating agent and then (ii) reacting the product with an aminating agent. Part (i) of step (3) involves reacting an N-oxide of Formula XV with an acylating agent. Suitable acylating agents include alkyl- or arylsulfonyl chlorides (e.g., benezenesulfonyl chloride, methanesulfonyl chloride, p-toluenesulfonyl chloride). Arylsulfonyl chlorides are preferred. Para-toluenesulfonyl chloride is most preferred. Part (ii) of step (3) involves reacting the product of part (i) with an excess of an aminating agent. Suitable aminating agents include ammonia (e.g., in the form of ammonium hydroxide) and ammonium salts (e.g., ammonium carbonate, ammonium bicarbonate, ammonium phosphate). Ammonium hydroxide is preferred. The reaction is preferably carried out by dissolving the N-oxide of Formula XV in an inert solvent such as dichloromethane, adding the aminating agent to the solution, and then slowly adding the acylating agent. The product or a pharmaceutically acceptable salt thereof can be isolated using conventional methods.

Alternatively, step (3) may be carried out by (i) reacting an N-oxide of Formula XV with an isocyanate and then (ii) hydrolyzing the resulting product. Part (i) involves reacting the N-oxide with an isocyanate wherein the isocyanato group is bonded to a carbonyl group. Preferred isocyanates include trichloroacetyl isocyanate and aroyl isocyanates such as benzoyl isocyanate. The reaction of the isocyanate with the N-oxide is carried out under substantially anhydrous conditions by adding the isocyanate to a solution of the N-oxide in an inert solvent such as chloroform or dichloromethane. Part (ii) involves hydrolysis of the product from part (i). The hydrolysis can be carried out by conventional methods such as heating in the presence of water or a lower alkanol optionally in the presence of a catalyst such as an alkali metal hydroxide or lower alkoxide. The product or a pharmaceutically acceptable salt thereof can be isolated using conventional methods.

Reaction Scheme II

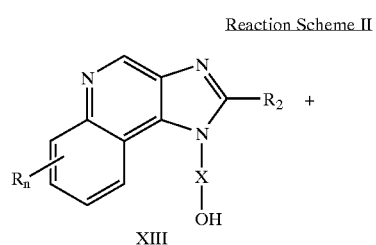

XIII

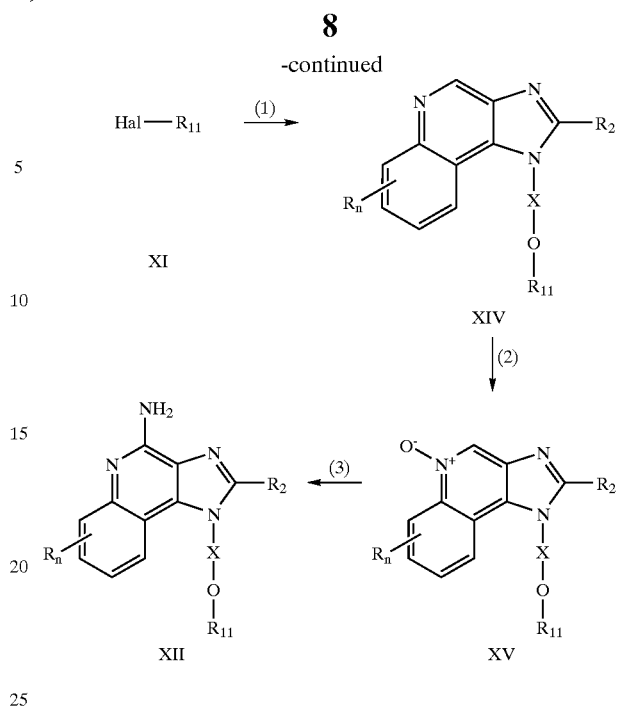

Compounds of Formula I wherein R, $R_2$, X and n are as defined above and $R_1$ is an optionally substituted phenyl can be prepared according to Reaction Scheme III where m is 0 to 3 and each R' is independently selected from the group consisting of alkyl, alkoxy, alkylthio, haloalkyl, haloalkoxy, haloalkylthio, halogen, nitro, mercapto, cyano, carboxy, formyl, aryl, aryloxy, arylthio, arylalkoxy, arylalkylthio, heteroaryl, heteroaryloxy, heteroarylthio, heteroarylalkoxy, heteroarylalkylthio, amino, alkylamino, dialkylamino, heterocyclyl, heterocycloalkyl, alkylcarbonyl, alkenylcarbonyl, arylcarbonyl, alkoxycarbonyl, haloalkylcarbonyl, haloalkoxycarbonyl, alkylthiocarbonyl, aryloxycarbonyl, alkanoyloxy, alkanoylthio, alkanoylamino, aroyloxy and aroylamino.

In Reaction Scheme III a 4-amino-1H-imidazo[4,5-c] quinolin-1-yl alcohol of Formula X is condensed with a phenol of Formula XVI to provide a 1H-imidazo[4,5-c] quinolin-4-amine of Formula XVII which is a subgenus of Formula I. Preferably, a solution of a compound of Formula X and the phenol in a suitable solvent such as N,N-dimethylformamide is treated with diethyl azodicarboxylate and triphenylphosphine at ambient temperature. The product or a pharmaceutically acceptable salt thereof can be isolated using conventional methods.

Reaction Scheme III

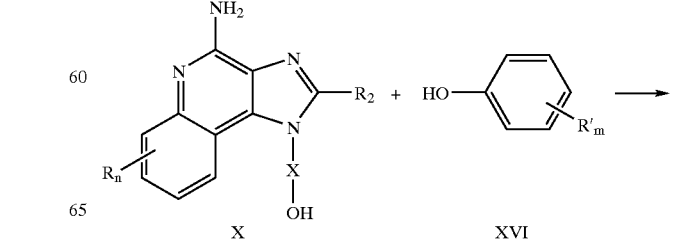

X    XVI

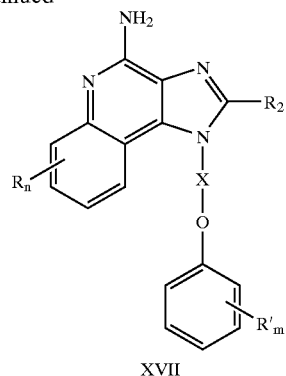

XVII

Compounds of the invention can also be prepared according to Reaction Scheme IV where R, $R_2$, $R_{11}$, X and n are as defined above.

In step (1) of Reaction Scheme IV the hydroxy group of a 1H-imidazo[4,5-c]quinolin-1-yl alcohol of Formula XIII is protected with a benzyl group. The alcohol of Formula XIII is reacted with sodium hydride in a suitable solvent such as N,N-dimethylformamide to form an alkoxide. The alkoxide is then alkylated with benzyl bromide to provide a compound of Formula XVIII. The reaction can be carried out at ambient temperature.

In step (2) of Reaction Scheme IV a compound of Formula XVIII is oxidized using the method of step (2) of Reaction Scheme II to provide a 1H-imidazo[4,5-c]quinoline-5N-oxide of Formula XIX.

In step (3) of Reaction Scheme IV a 1H-imidazo[4,5-c]quinoline-5N-oxide of Formula XIX is chlorinated to provide a 4-chloro-1H-imidazo[4,5-c]quinoline of Formula XX. Preferably a solution of a compound of Formula XIX in a suitable solvent such as toluene is treated with phosphorous oxychloride at ambient temperature.

In step (4) of Reaction Scheme IV a 4-chloro-1H-imidazo[4,5-c]quinoline of Formula XX is reacted with phenol to provide a 4-phenoxy-1H-imidazo[4,5-c]quinoline of Formula XXI. The phenol is reacted with sodium hydride in a suitable solvent such as diglyme to form a phenoxide. The phenoxide is then reacted at an elevated temperature with a compound of Formula XX.

In step (5) of Reaction Scheme IV the benzyl protecting group is removed from a compound of Formula XXI to provide a 4-phenoxy-1H-imidazo[4,5-c]quinolin-1-yl alcohol of Formula XXII. The reaction is preferably carried out by adding triflic acid in a controlled fashion to a solution of a compound of Formula XXI in a suitable solvent such as dichloromethane at ambient temperature.

In step (6) of Reaction Scheme IV a 4-phenoxy-1H-imidazo[4,5-c]quinolin-1-yl alcohol of Formula XXII is alkylated with a halide of Hal-$R_{11}$ to provide a 4-phenoxy-1H-imidazo[4,5-c]quinolin-1-yl ether of Formula XXIII. The alkoxide of a compound of Formula XXII is formed by adding the alcohol to a biphasic mixture of aqueous 50% sodium hydroxide and an inert solvent such as dichloromethane in the presence of a phase transfer catalyst such as benzyltrimethlammonium chloride. The alkoxide is then alkylated. The reaction can be carried out at ambient temperature.

In step (7) of Reaction Scheme IV a 4-phenoxy-1H-imidazo[4,5-c]quinolin-1-yl ether of Formula XXIII is aminated to provide a 1H-imidazo[4,5-c]quinolin-4-amine of Formula XII which is a subgenus of Formula I. The reaction can be carried out by combining a compound of Formula XXIII with ammonium acetate and heating the resulting mixture at ~150° C. The product or a pharmaceutically acceptable salt thereof can be isolated using conventional methods.

Reaction Scheme IV

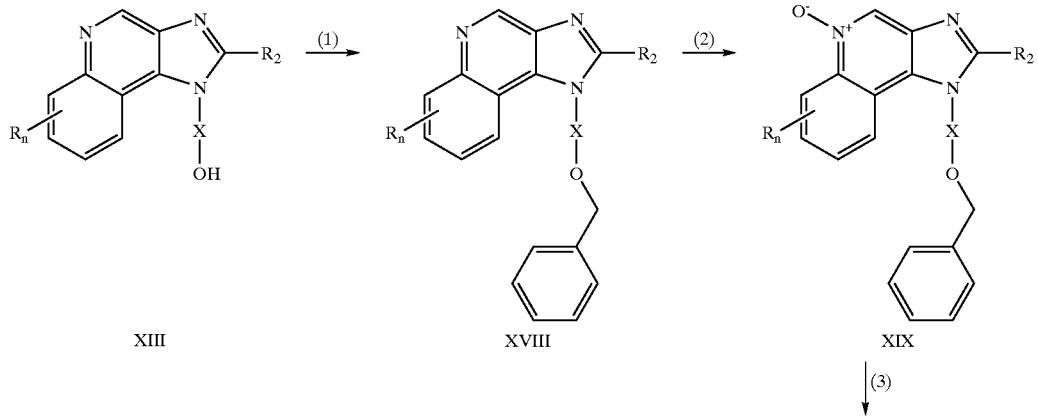

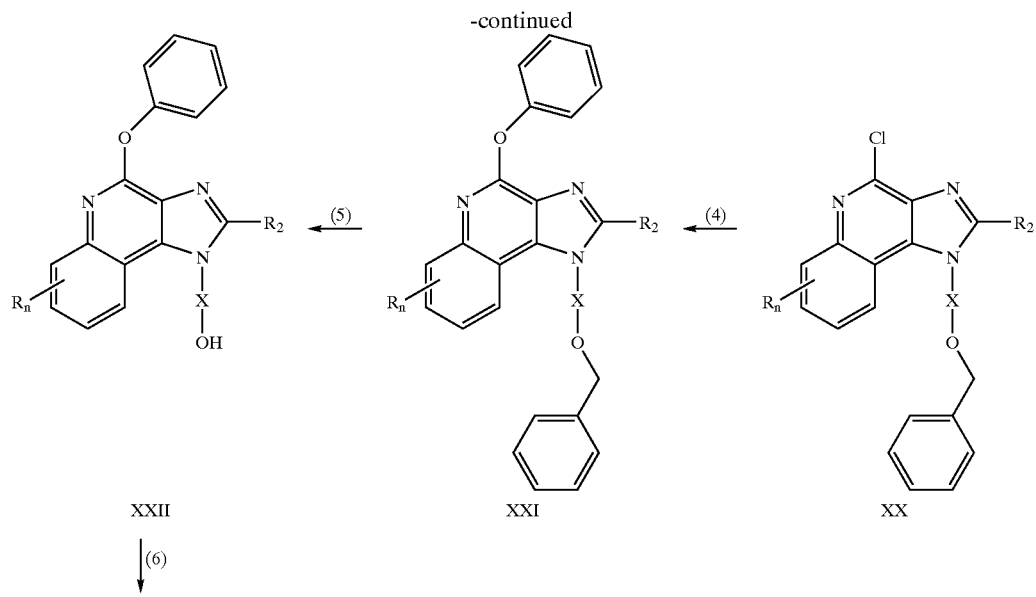

XXII    XXI    XX

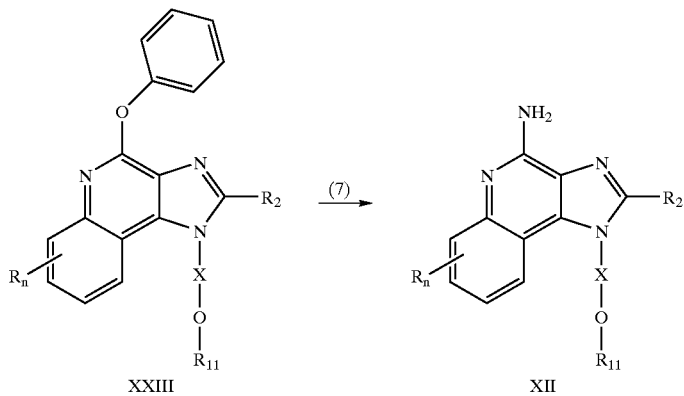

XXIII    XII

Tetrahydroimidazoquinolines of the invention can be prepared according to Reaction Scheme V where R, $R_2$, $R_{11}$, X and n are as defined above.

In Reaction Scheme V a 4-amino-6,7,8,9-tetrahydro-1H-imidazo[4,5-c]quinolin-1-yl alcohol of Formula XXIV is alkylated with a halide of Formula XI to provide a 6,7,8,9-tetrahydro-1H-imidazo[4,5-c]quinolin-4-amine of Formula XXV which is a subgenus of Formula III. The alcohol of Formula XXIV is reacted with sodium hydride in a suitable solvent such as N,N-dimethylformamide to form an alkoxide. The alkoxide is then combined with the halide. The reaction can be carried out at ambient temperature. The product or a pharmaceutically acceptable salt thereof can be isolated using conventional methods.

Many tetrahydro-1H-imidazo[4,5-c]quinolines of Formula XXIV are known, see for example, Nikolaides et al., U.S. Pat. No. 5,352,784; others can be prepared using known synthetic methods, see for example, Lindstrom, U.S. Pat. No. 5,693,811; the disclosures of which are incorporated by reference herein.

Reaction Scheme V

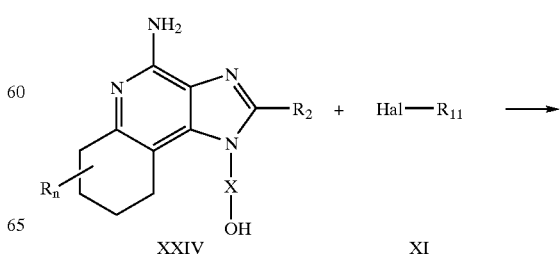

XXIV    XI

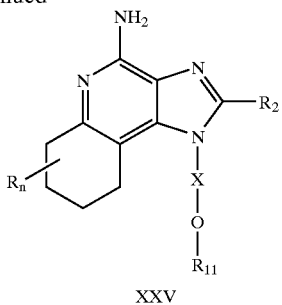

XXV

Compounds of the invention can also be prepared according to Reaction Scheme VI where R, $R_1$, $R_2$, X and n are as defined above.

In step (1) of Reaction Scheme VI a 4-chloro-3-nitroquinoline of Formula XXVI is reacted with an amine of Formula $R_1$—O—X—$NH_2$ to provide a 3-nitroquinolin-4-amine of Formula XXVII. The reaction can be carried out by adding the amine to a solution of a compound of Formula XXVI in a suitable solvent such as chloroform or dichloromethane and optionally heating. Many quinolines of Formula XXVI are known compounds (see for example, U.S. Pat. No. 4,689,338 and references cited therein).

In step (2) of Reaction Scheme VI a 3-nitroquinolin-4-amine of Formula XXVII is reduced to provide a quinoline-3,4-diamine of Formula XXVIII. Preferably, the reduction is carried out using a conventional heterogeneous hydrogenation catalyst such as platinum on carbon or palladium on carbon. The reaction can conveniently be carried out on a Parr apparatus in a suitable solvent such as isopropyl alcohol or preferably toluene.

In step (3) of Reaction Scheme VI a quinoline-3,4-diamine of Formula XXVIII is reacted with a carboxylic acid or an equivalent thereof to provide a 1H-imidazo[4,5-c]quinoline of Formula XXIX. Suitable equivalents to carboxylic acid include orthoesters, and 1,1-dialkoxyalkyl alkanoates. The carboxylic acid or equivalent is selected such that it will provide the desired $R_2$ substituent in a compound of Formula XXIX. For example, triethyl orthoformate will provide a compound where $R_2$ is hydrogen and triethyl orthoacetate will provide a compound where $R_2$ is methyl. The reaction can be run in the absence of solvent or in an inert solvent such as toluene. The reaction is run with sufficient heating to drive off any alcohol or water formed as a byproduct of the reaction. Optionally a catalyst such as pyridine hydrochloride can be included.

Alternatively, step (3) can be carried out by (i) reacting the diamine of Formula XXVIII with an acyl halide of Formula $R_2C(O)Cl$ and then (ii) cyclizing. In part (i) the acyl halide is added to a solution of the diamine in a suitable solvent such as acetonitrile, pyridine or dichloromethane. The reaction can be carried out at ambient temperature. In part (ii) the product of part (i) is heated in an alcoholic solvent in the presence of a base. Preferably the product of part (i) is refluxed in ethanol in the presence of an excess of triethylamine or heated with methanolic ammonia. Alternatively, if step (i) has been run in pyridine, step (ii) can be carried out by heating the reaction mixture after analysis indicates that step (i) is complete.

In step (4) of Reaction Scheme VI a 1H-imidazo[4,5-c]quinoline of Formula XXIX is oxidized using the method of step (2) of Reaction Scheme II to provide a 1H-imidazo[4,5-c]quinoline-5N-oxide of Formula XXX In step (5) of Reaction Scheme VI a 1H-imidazo[4,5-c]quinoline-5N-oxide of Formula XXX is aminated using the method of step (3) of Reaction Scheme II to provide a 1H-imidazo[4,5-c]quinolin-4-amine of Formula I.

Reaction Scheme VI

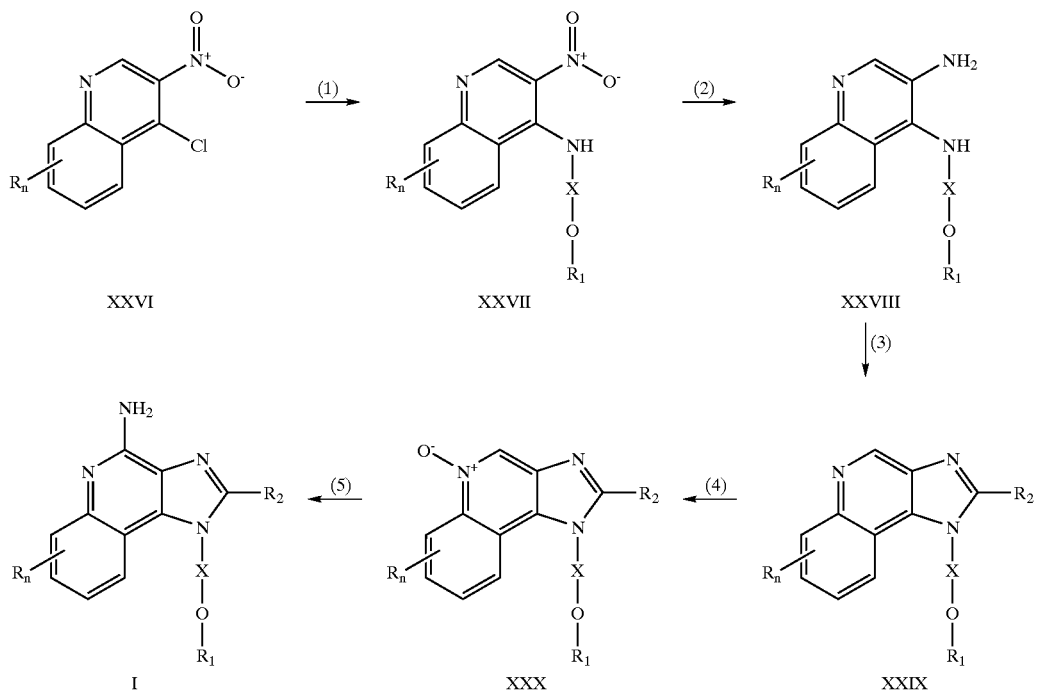

Compounds of the invention can be prepared according to Reaction Scheme VII where R, $R_2$, X and n are as defined above and $R_{12}$ is an aryl group which may be unsubstituted or substituted as defined above.

In step (1) of Reaction Scheme VII a 1H-imidazo[4,5-c]quinolin-1-yl alcohol of Formula XIII is alkylated with a halide of Formula XXXI to provide a 1H-imidazo[4,5-c]quinolin-1-yl ether of Formula XXXII. The compound of Formula XIII and the halide of Formula XXXI are combined in a biphasic mixture of 50% aqueous sodium hydroxide and a suitable solvent such as dichloromethane in the presence of a phase transfer catalyst such as benzyltrimethylammonium chloride. The reaction can be run at ambient temperature.

In step (2) of Reaction Scheme VII a 1H-imidazo[4,5-c]quinoline of Formula XXXII is oxidized using the method of step (2) of Reaction Scheme II to provide a 1H-imidazo[4,5-c]quinoline-5N-oxide of Formula XXXIII.

In step (3) of Reaction Scheme VII a 1H-imidazo[4,5-c]quinoline-5N-oxide of Formula XXXIII is reacted with trichloroacetyl isocyanate to provide a 1H-imidazo[4,5-c]quinolin-4-yl trichloroacetamide of Formula XXXIV. Preferably the isocyanate is added in a controlled fashion at ambient temperature to a solution of the 5N-oxide in a suitable solvent such as dichloromethane.

In step (4) of Reaction Scheme VII a 1H-imidazo[4,5-c]quinolin-4-yl trichloroacetamide of Formula XXXIV is hydrolyzed to provide a 1H-imidazo[4,5-c]quinolin-4-amine of Formula XXXV which is a subgenus of Formula II. The hydrolysis can be carried out by conventional methods, preferably by treating a solution of a compound of Formula XXXIV in methanol with sodium methoxide.

In step (5) of Reaction Scheme VII 1H-imidazo[4,5-c]quinolin-4-amine of Formula XXXV is coupled with a halide of formula Hal-$R_{12}$ using a transition metal catalyst to provide a 1H-imidazo[4,5-c]quinolin-4-amine of Formula XXXVI which is a subgenus of Formula II. Preferably a compound of Formula XXXV is combined with the halide in the presence of copper (I) iodide, dichlorobis(triphenylphosphine)palladium(II), and excess triethylamine in a suitable solvent such as N,N-dimethylformamide or acetonitrile. The reaction is preferably carried out at an elevated temperature (60–80° C.). The product or a pharmaceutically acceptable salt thereof can be isolated using conventional methods.

Reaction Scheme VII

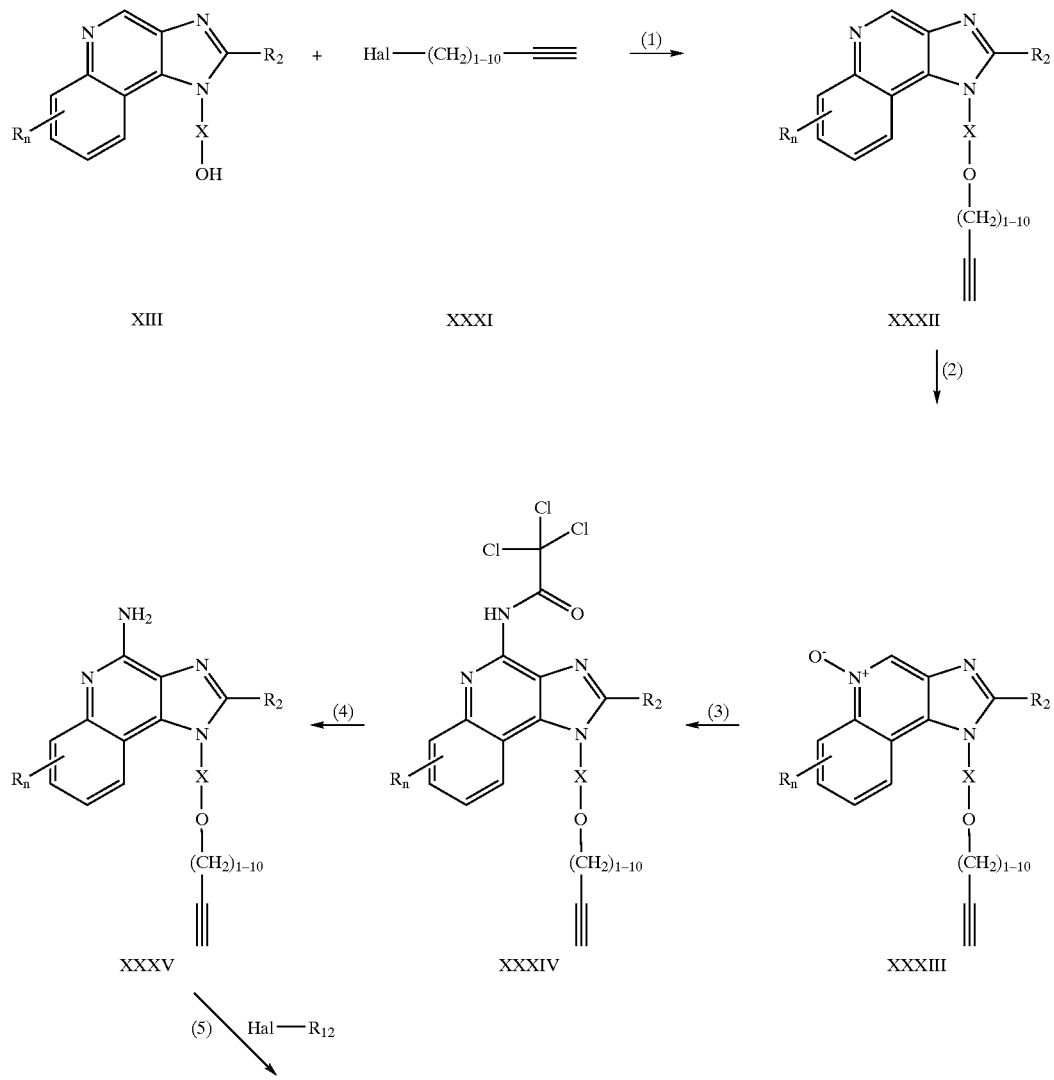

-continued

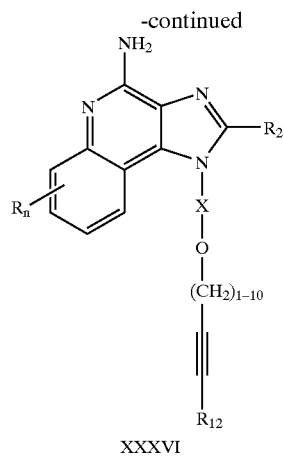

XXXVI

Compounds of the invention can be prepared according to Reaction Scheme VIII where R, $R_2$, $R_{12}$, X and n are as defined above and BOC is tert-butoxycarbonyl.

In step (1) of Reaction Scheme VIII the amino group of a 1H-imidazo[4,5-c]quinolin-4-amine of Formula XXXV is protected with two tert-butoxycarbonyl groups. A compound of Formula XXXV is combined with di-tert-butyl dicarbonate in a suitable solvent such as N,N-dimethylformamide in the presence of 4-(dimethylamino)pyridine and triethylamine. The reaction is carried out at an elevated temperature (80–85° C.).

In step (2) of Reaction Scheme VIII a protected 1H-imidazo[4,5-c]quinolin-4-amine of Formula XXXVII is coupled with a halide of formula Hal-$R_{12}$ using a transition metal catalyst to provide a protected 1H-imidazo[4,5-c]quinolin-4-amine of Formula XXXVIII. Preferably a compound of Formula XXXVII is combined with the halide in the presence of copper (I) iodide, dichlorobis(triphenylphosphine)palladium(II), and excess triethylamine in a suitable solvent such as N,N-dimethylformamide or acetonitrile. The reaction can be carried out at ambient temperature or at an elevated temperature (40–80° C.).

In step (3) of Reaction Scheme VIII the protecting groups are removed by hydrolysis under acidic conditions to provide a 1H-imidazo[4,5-c]quinolin-4-amine of Formula XXXVI which is a subgenus of Formula II. Preferably a compound of Formula XXXVIII is treated with trifluoroacetic acid in a suitable solvent such as dichloromethane. The reaction can be run at ambient temperature or at a reduced temperature (0° C.). The product or a pharmaceutically acceptable salt thereof can be isolated using conventional methods.

In step (4) of Reaction Scheme VIII the alkyne bond of a protected 1H-imidazo[4,5-c]quinolin-4-amine of Formula XXXVIII is reduced to provide a protected 1H-imidazo[4,5-c]quinolin-4-amine of Formula XXXIX. Preferably, the reduction is carried out using a conventional heterogeneous hydrogenation catalyst such as platinum oxide, platinum on carbon or palladium on carbon. The reaction can conveniently be carried out on a Parr apparatus in a suitable solvent such as methanol.

In step (5) of Reaction Scheme VIII the protecting groups of a compound of Formula XXXIX are removed in the same manner as in step (3) to provide a 1H-imidazo[4,5-c]quinolin-4-amine of Formula XL which is a subgenus of Formula I. The product or a pharmaceutically acceptable salt thereof can be isolated using conventional methods.

Reaction Scheme VIII

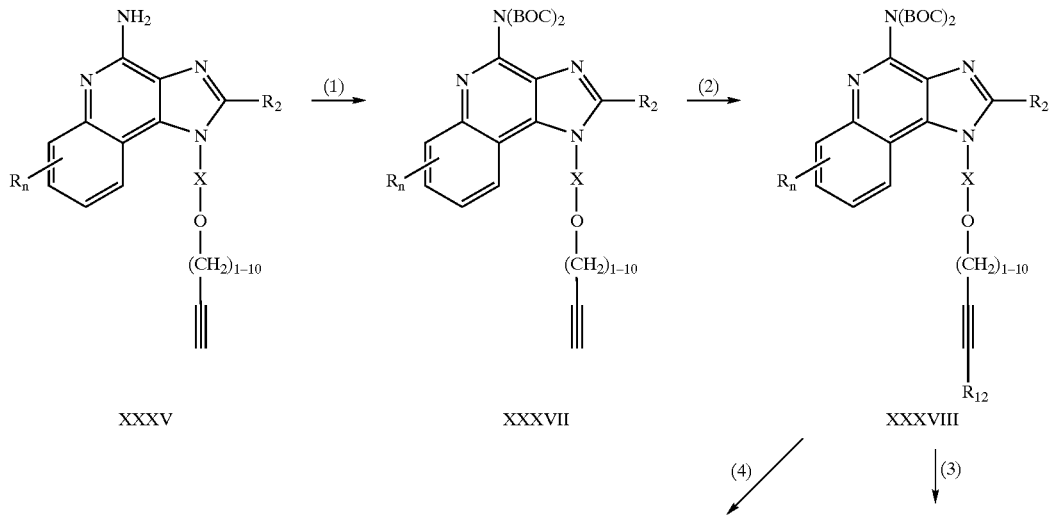

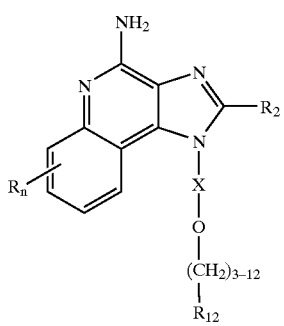

XL

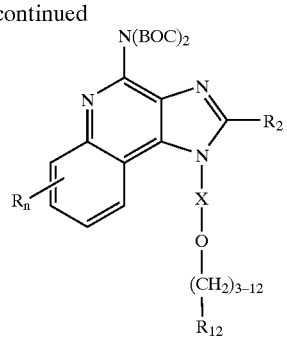

XXXIX    XXXVI

Compounds of the invention can be prepared according to Reaction Scheme IX where R, $R_2$, $R_{12}$, X and n are as defined above and CBZ is benzyloxycarbonyl.

In step (1) of Reaction Scheme IX the amino group of a 1H-imidazo[4,5-c]quinolin-4-amine of Formula XXXV is protected with benzyloxycarbonyl groups. A compound of Formula XXXV is combined with dibenzyl dicarbonate in a suitable solvent such as N,N-dimethylformamide. The reaction can be carried out at ambient temperature or with mild heating (40° C.).

In step (2) of Reaction Scheme IX a protected 1H-imidazo[4,5-c]quinolin-4-amine of Formula XLI is coupled with a halide of formula Hal-$R_{12}$ using a transition metal catalyst to provide a protected 1H-imidazo[4,5-c]quinolin-4-amine of Formula XLII. Preferably a compound of Formula XLI is combined with the halide in the presence of copper (I) iodide, dichlorobis(triphenylphosphine)palladium(II), and excess triethylamine in a suitable solvent such as N,N-dimethylformamide or acetonitrile. The reaction can be carried out at ambient temperature or at an elevated temperature (40–80° C.).

In step (3) of Reaction Scheme IX the protecting groups are removed by hydrolysis to provide a 1H-imidazo[4,5-c]quinolin-4-amine of Formula XXXVI which is a subgenus of Formula II. Preferably a compound of Formula XLII is treated with sodium methoxide in a suitable solvent such as methanol. The reaction can be run at ambient temperature. The product or a pharmaceutically acceptable salt thereof can be isolated using conventional methods.

In step (4) of Reaction Scheme IX the protecting groups of a compound of Formula XLII are removed by hydrogenolysis and the alkyne bond is reduced to provide a 1H-imidazo[4,5-c]quinolin-4-amine of Formula XL which is a subgenus of Formula I. Preferably, the hydrogenolysis/reduction is carried out using palladium hydroxide on carbon. The reaction can conveniently be carried out on a Parr apparatus in a suitable solvent such as methanol. The product or a pharmaceutically acceptable salt thereof can be isolated using conventional methods.

Reaction Scheme IX

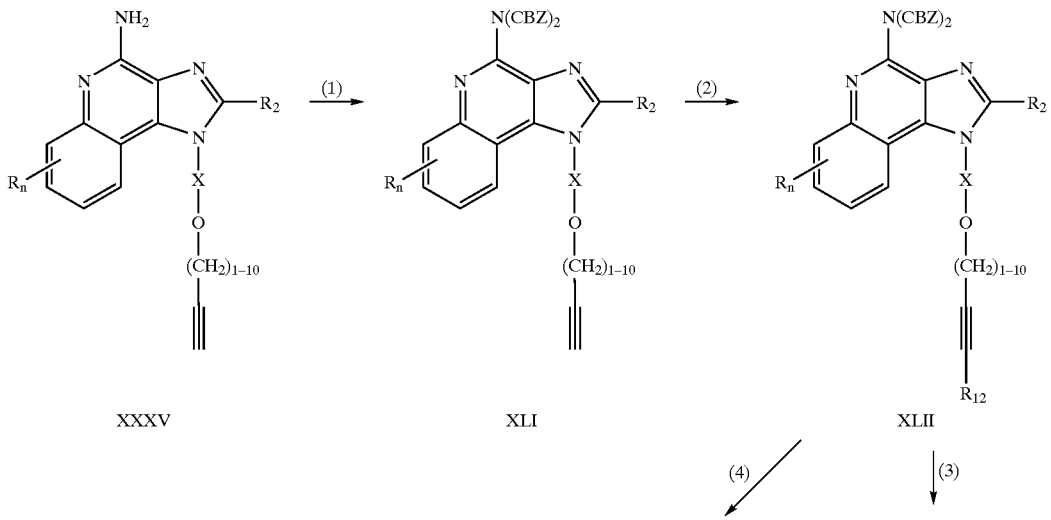

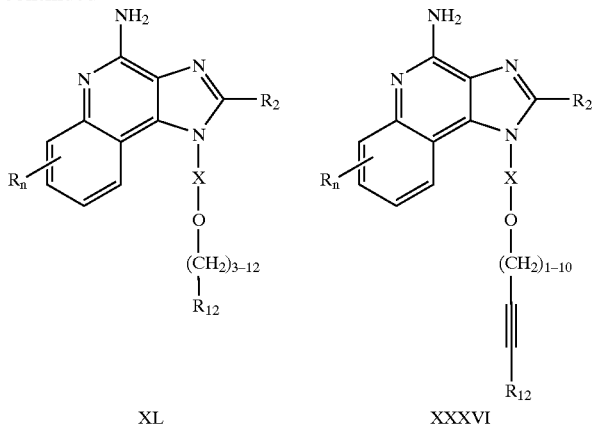

XL                                    XXXVI

Compounds of the invention can be prepared according to Reaction Scheme X where R, $R_1$, $R_2$, X and n are as defined above.

In step (1) of Reaction Scheme X a 2,4-dichloro-3-nitroquinoline of Formula XLIII is reacted with an amine of Formula $R_1$—O—X—$NH_2$ to provide a 2-chloro-3-nitroquinolin-4-amine of Formula XLIV. The reaction can be carried out by adding the amine to a solution of a compound of Formula XLIII in a suitable solvent such as chloroform or dichloromethane and optionally heating. Many quinolines of Formula XLIII are known or can be prepared using known synthetic methods (see for example, Andre et al., U.S. Pat. No. 4,988,815 and references cited therein).

In step (2) of Reaction Scheme X a 2-chloro-3-nitroquinolin-4-amine of Formula XLIV is reduced using the method of step (2) in Reaction Scheme VI to provide a 2-chloroquinoline-3,4-diamine of Formula XLV.

In step (3) of Reaction Scheme X a 2-chloroquinoline-3,4-diamine of Formula XLV is cyclized using the method of step (3) in Reaction Scheme VI to provide a 4-chloro-1H-imidazo[4,5-c]quinoline of Formula XLVI.

In step (4) of Reaction Scheme X a 4-chloro-1H-imidazo[4,5-c]quinoline of Formula XLVI is aminated to provide a 1H-imidazo[4,5-c]quinolin-4-amine of Formula I. The reaction is carried out by heating (e.g., 125–175° C.) a compound of Formula XLVI under pressure in a sealed reactor in the presence of a solution of ammonia in an alkanol. The product or a pharmaceutically acceptable salt thereof can be isolated using conventional methods.

Reaction Scheme X

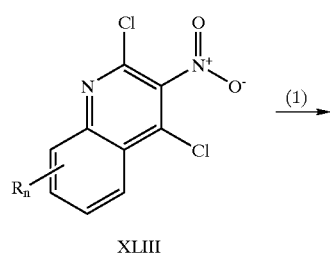

XLIII

Compounds of the invention can be prepared according to Reaction Scheme XI where R, $R_1$, $R_2$, X and n are as defined above.

In Reaction Scheme XI a 1H-imidazo[4,5-c]quinolin-4-amine of Formula XLVII is alkylated with a halide of Formula XLVIII to provide a 1H-imidazo[4,5-c]quinolin-4-amine of Formula I. The compound of Formula XLVII is reacted with sodium hydride in a suitable solvent such as N,N-dimethylformamide. The halide is then added to the reaction mixture. The reaction can be carried out at an elevated temperature (~100° C.). Alkylation occurs at both the N1 and the N3 nitrogens; however, the desired 1-isomer can be readily separated from the 3-isomer using conventional techniques such as column chromatography and recrystallization.

Many 1H-imidazo[4,5-c]quinolin-4-amines of Formula XLVII are known; others may be prepared using known synthetic methods, see for example, Gerster, U.S. Pat. No. 5,756,747 and the references cited therein.

Reaction Scheme XI

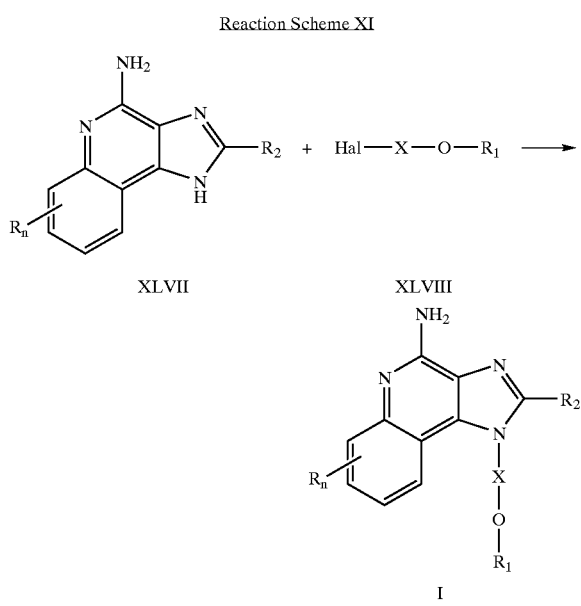

Compounds of the invention can be prepared according to Reaction Scheme XII where R, $R_1$ $R_2$, X and n are as defined above.

In step (1) of Reaction Scheme XII a 4-nitrotetrazolo[1,5-a]quinolin-5-ol of Formula XLIX is chlorinated to provide a 5-chloro-4-nitrotetrazolo[1,5-a]quinoline of Formula L. Conventional chlorinating agents can be used. Preferably the reaction is carried out using phosphorus oxychloride in a suitable solvent such as N,N-dimethylformamide.

4-Nitrotetrazolo[1,5-a]quinolin-5-ols of Formula XLIX are known or can be prepared using known synthetic methods (see for example, Gerster, et al., U.S. Pat. No. 5,741,908 and references cited therein).

In step (2) of Reaction Scheme XII a 5-chloro-4-nitrotetrazolo[1,5-a]quinoline of Formula L is reacted with an amine of Formula $R_1$—O—X—$NH_2$ to provide a 4-nitrotetrazolo[1,5-a]quinolin-5-amine of Formula LI. The reaction can be carried out by adding the amine to a solution of a compound of Formula L in a suitable solvent such as dichloromethane in the presence of triethylamine.

In step (3) of Reaction Scheme XII a 4-nitrotetrazolo[1,5-a]quinolin-5-amine of Formula LI is reduced using the method of step (2) in Reaction Scheme VI to provide a tetrazolo[1,5-a]quinolin-4,5-diamine of Formula LII.

In step (4) of Reaction Scheme XII a tetrazolo[1,5-a]quinolin-4,5-diamine of Formula LII is cyclized using the method of step (3) in Reaction Scheme VI to provide a 6H-imidazo[4,5-c]tetrazolo[1,5-a]quinoline of Formula LIII.

In step (5) of Reaction Scheme XII a 6H-imidazo[4,5-c]tetrazolo[1,5-a]quinoline of Formula LIII is reduced to provide a 1H-imidazo[4,5-c]quinolin-4-amine of Formula I. Step (5) involves (i) reacting a compound of Formula LIII with triphenylphosphine and then (ii) hydrolyzing. Part (i) can be carried out by combining a compound of Formula LIII with triphenylphosphine in a suitable solvent such as 1,2-dichlorobenzene and heating. Part (ii) involves hydrolysis of the product from part (i). The hydrolysis can be carried out by conventional methods such as heating in the presence of water or a lower alkanol optionally in the presence of a catalyst such as an alkali metal hydroxide or lower alkoxide. The product or a pharmaceutically acceptable salt thereof can be isolated using conventional methods.

Reaction Scheme XII

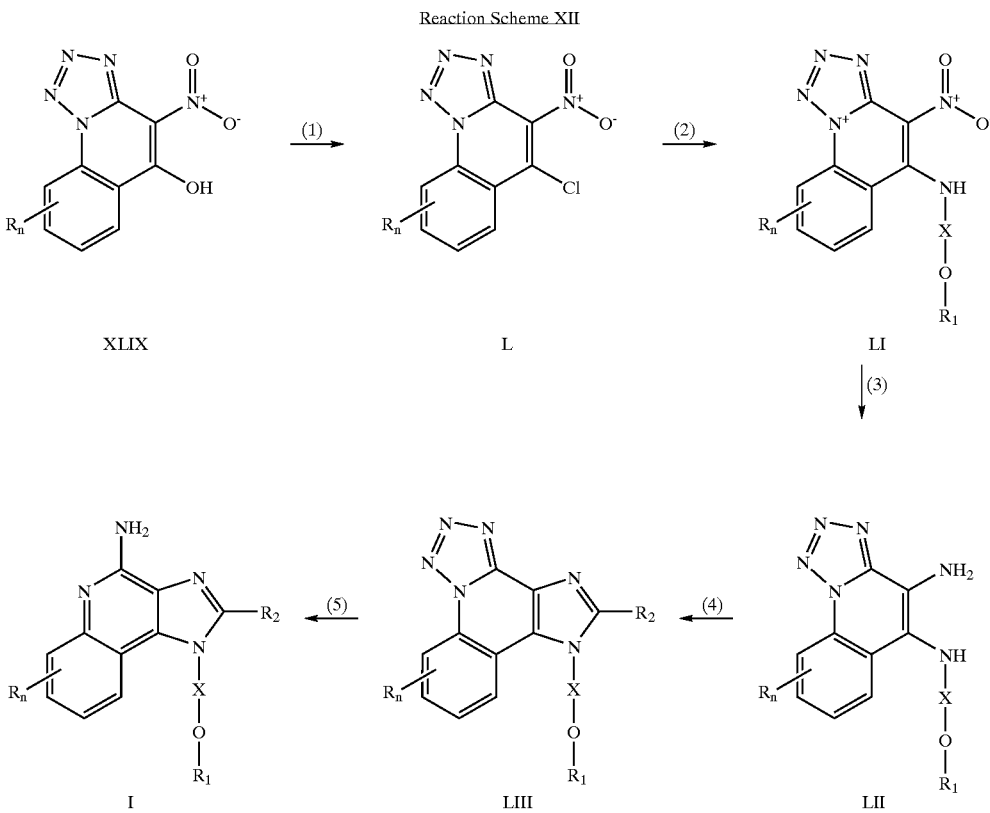

Compounds of the invention can be prepared according to Reaction Scheme XIII where R, $R_2$, $R_{12}$, X and n are as defined above.

In step (1) of Reaction Scheme XIII a 1H-imidazo[4,5-c]quinolin-1-yl ether of Formula XXXII is coupled with a halide of Formula Hal-$R_{12}$ using the method of step (5) in Reaction Scheme VII to provide a 1H-imidazo[4,5-c]quinolin-1-yl ether of Formula LIV.

In step (2) of Reaction Scheme XIII a 1H-imidazo[4,5-c]quinolin-1-yl ether of Formula LIV is oxidized using the method of step (2) in Reaction Scheme II to provide a 1H-imidazo[4,5-c]quinoline-5N-oxide of Formula LV.

In step (3) of Reaction Scheme XIII a 1H-imidazo[4,5-c]quinoline-5N-oxide of Formula LV is aminated using the method of step (3) in Reaction Scheme II to provide a 1H-imidazo[4,5-c]quinolin-4-amine of Formula XXXVI which is a subgenus of Formula II. The product or a pharmaceutically acceptable salt thereof can be isolated using conventional methods.

Reaction Scheme XIII

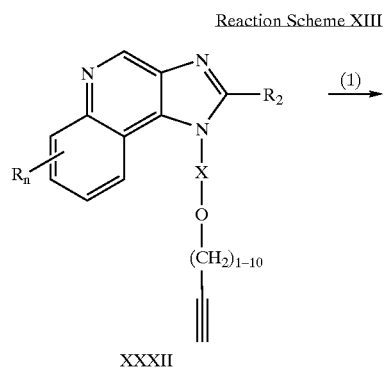

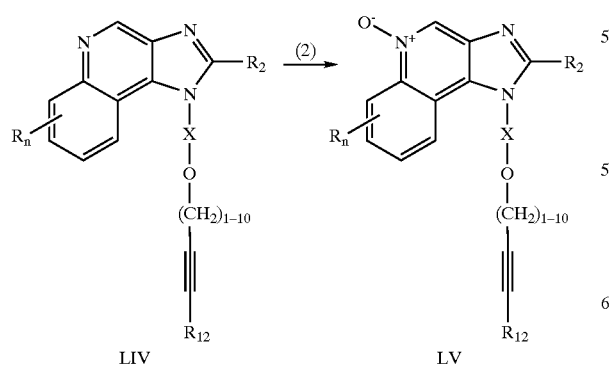

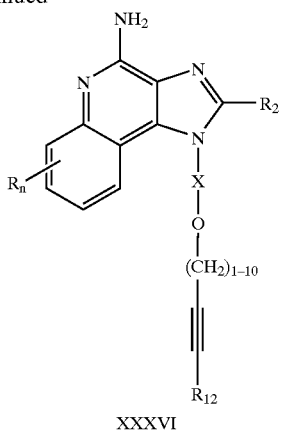

Compounds of the invention can be prepared according to Reaction Scheme XIV where R, $R_2$, $R_{12}$, X and n are as defined above.

In step (1) of Reaction Scheme XIV the alkyne bond of a 1H-imidazo[4,5-c]quinolin-1-yl ether of Formula LIV is reduced using the method of step (4) of Reaction Scheme VIII to provide a 1H-imidazo[4,5-c]quinolin-1-yl ether of Formula LVI.

In step (2) of Reaction Scheme XIV a 1H-imidazo[4,5-c]quinolin-1-yl ether of Formula LVI is oxidized using the method of step (2) in Reaction Scheme II to provide a 1H-imidazo[4,5-c]quinoline-5N-oxide of Formula LVII.

In step (3) of Reaction Scheme XIV a 1H-imidazo[4,5-c]quinoline-5N-oxide of Formula LVII is aminated using the method of step (3) in Reaction Scheme II to provide a 1H-imidazo[4,5-c]quinolin-4-amine of Formula XL which is a subgenus of Formula I. The product or a pharmaceutically acceptable salt thereof can be isolated using conventional methods.

Reaction Scheme XIV

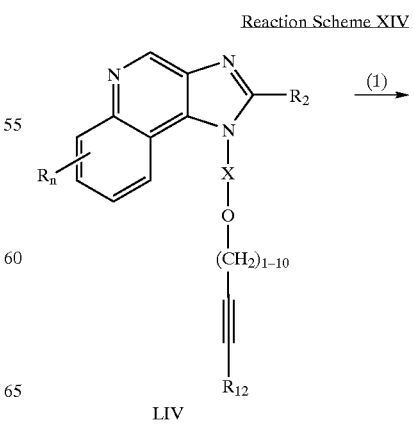

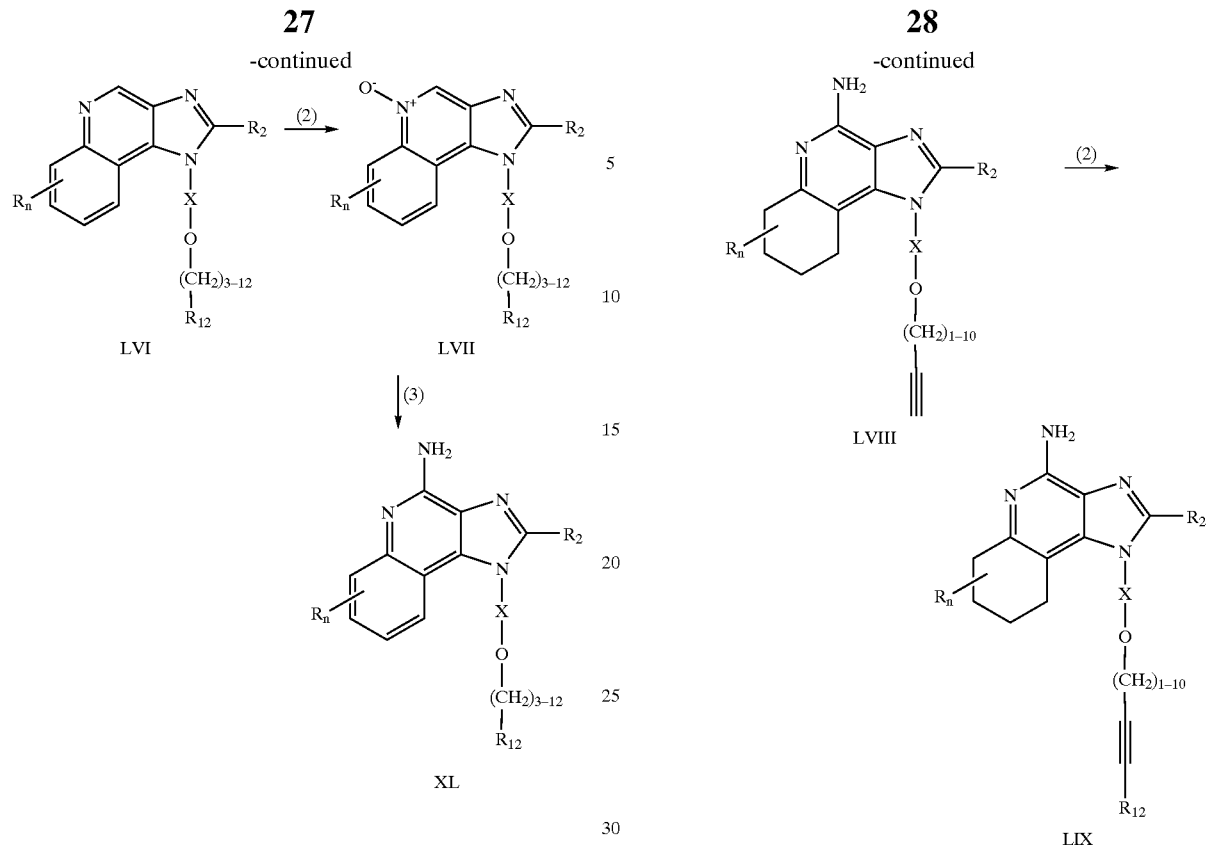

Tetrahydroimidazoquinolines of the invention can be prepared according to Reaction Scheme XV where R, $R_2$, $R_{12}$, X and n are as defined above.

In step (1) of Reaction Scheme XV a 4-amino-6,7,8,9-tetrahydro-1H-imidazo[4,5-c]quinolin-1-yl alcohol of Formula XXIV is alkylated using the method described in Reaction Scheme V with a halide of Formula Hal-$(CH_2)_{1-10}$—CH≡CH to provide a 6,7,8,9-tetrahydro-1H-imidazo[4,5-c]quinolin-4-amine of Formula LVIII which is a subgenus of Formula IV.

In step (2) of Reaction Scheme XV a 6,7,8,9-tetrahydro-1H-imidazo[4,5-c]quinolin-4-amine of Formula LVIII is coupled using the method of step (5) of Reaction Scheme VII with a halide of Formula Hal-$R_{12}$ to provide a 6,7,8,9-tetrahydro-1H-imidazo[4,5-c]quinolin-4-amine of Formula LIX which is a subgenus of Formula IV. The product or a pharmaceutically acceptable salt thereof can be isolated using conventional methods.

Reaction Scheme XV

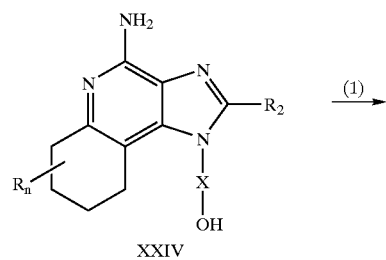

Compounds of the invention can be prepared according to Reaction Scheme XVI where R, $R_1$, $R_2$, X and n are as defined above.

In step (1) of Reaction Scheme XVI a 2,4-dihydroxy-3-nitro-6,7,8,9-tetrayhydroquinoline of Formula LX is chlorinated to provide a 2,4-dichloro-3-nitro-6,7,8,9-tetrayhydroquinoline of Formula LXI. Conventional chlorinating agents can be used. Preferably the reaction is carried out by combining a compound of Formula LX with phosphorous oxychloride and then heating (55–65° C.). Compounds of Formula LX are known or can be prepared using known synthetic methods (see for example Nikolaides et al,. U.S. Pat. No. 5,352,784 and references cited therein).

In step (2) of Reaction Scheme XVI a 2,4-dichloro-3-nitro-6,7,8,9-tetrahydroquinoline of Formula LXI is reacted with an amine of Formula $R_1$—O—X—$NH_2$ to provide a 2-chloro-3-nitro-6,7,8,9-tetrahydroquinolin-4-amine of Formula LXII. The reaction can be carried out by adding the amine to a solution of a compound of Formula LXI in a suitable solvent such as N,N-dimethylformamide and heating (55–65° C.).

In step (3) of Reaction Scheme XVI a 2-chloro-3-nitro-6,7,8,9-tetrahydroquinolin-4-amine of Formula LXII is reacted with phenol using the method of step (4) of Reaction Scheme IV to provide a 2-phenoxy-3-nitro-6,7,8,9-tetrahydroquinolin-4-amine of Formula LXIII.

In step (4) of Reaction Scheme XVI a 2-phenoxy-3-nitro-6,7,8,9-tetrahydroquinolin-4-amine of Formula LXIII is reduced using the method of step (2) of Reaction Scheme VI to provide a 2-phenoxy-6,7,8,9-tetrahydroquinolin-3,4-diamine of Formula LXIV.

In step (5) of Reaction Scheme XVI a 2-phenoxy-6,7,8,9-tetrahydroquinolin-3,4-diamine of Formula LXIV is cyclized using the method of step (3) of Reaction Scheme VI to provide a 4-phenoxy-6,7,8,9-tetrahydro-1H-imidazo[4,5-c]quinoline of Formula LXV.

In step (6) of Reaction Scheme XVI a 4-phenoxy-6,7,8,9-tetrahydro-1H-imidazo[4,5-c]quinoline of Formula LXV is aminated using the method of step (7) of Reaction Scheme IV to provide a 6,7,8,9-tetrahydro-1H-imidazo[4,5-c]quinolin-4-amine of Formula III.

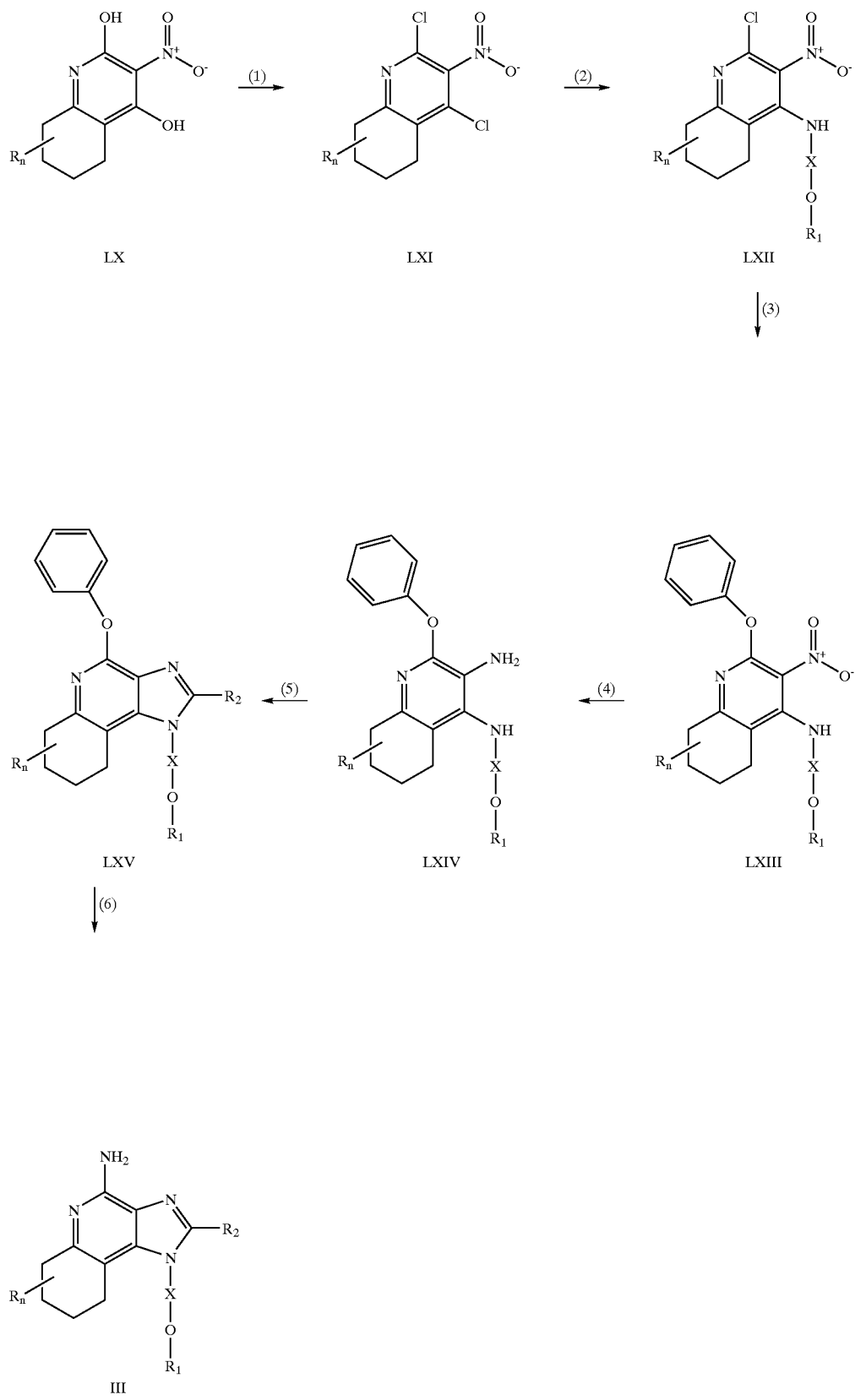

Compounds of the invention can also be prepared by combining steps from two or more of the above Reaction Schemes I–XVI. For Example, compounds of the Formula XXXVI (in Reaction Scheme VIII) can be prepared from compounds of the Formula X (in Reaction Scheme III) by combining the method of step (1) of Reaction Scheme VII with the methods of steps (1)–(3) of Reaction Scheme XIII. In another example, compounds of the Formula XL (in Reaction Scheme VIII) can be prepared from compounds of the Formula XXXVI using the method of step (4) in Reaction Scheme VIII.

The invention also provides novel compounds useful as intermediates in the synthesis of the compounds of Formulas (I), (II), (III), and (IV). These intermediate compounds have the structural Formulas (V)–(IX), described in more detail below.

One class of intermediate compounds has Formula (V):

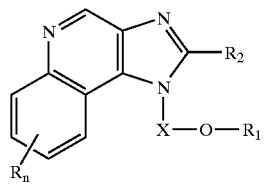

(V)

wherein X is —$CHR_3$—, —$CHR_3$-alkyl-, or —$CHR_3$-alkenyl-;
  $R_1$ is selected from the group consisting of:
    -aryl;
    -alkenyl;
    —$R_4$-aryl; and
    —$(CH_2)_{1-10}$—C≡C—$R_{10}$;
  $R_2$ is selected from the group consisting of:
    -hydrogen;
    -alkyl;
    -alkenyl;
    -aryl;
    -heteroaryl;
    -heterocyclyl;
    -alkyl-Y-alkyl;
    -alkyl-Y-alkenyl;
    -alkyl-Y-aryl; and
    -alkyl or alkenyl substituted by one or more substituents selected from the group consisting of:
      —OH;
      -halogen;
      —$N(R_3)_2$;
      —CO—$N(R_3)_2$;
      —CO—$C_{1-10}$ alkyl;
      —CO—O—$C_{1-10}$ alkyl;
      —$N_3$;
      -aryl;
      -heteroaryl;
      -heterocyclyl;
      —CO-aryl; and
      —CO-heteroaryl;
  $R_4$ is alkyl or alkenyl, which may be interrupted by one or more —O— groups;
  each $R_3$ is independently H or $C_{1-10}$ alkyl;
  $R_{10}$ is selected from the group consisting of H, alkyl, alkenyl, aryl, and -alkylaryl;
  each Y is independently —O— or —$S(O)_{0-2}$—;
  n is 0 to 4; and each R present is independently selected from the group consisting of $C_{1-10}$ alkyl, $C_{1-10}$ alkoxy, hydroxy, halogen and trifluoromethyl;
or a pharmaceutically acceptable salt thereof.

Another class of intermediates are imidazoquinoline-4-phenoxy compounds of Formula (VI):

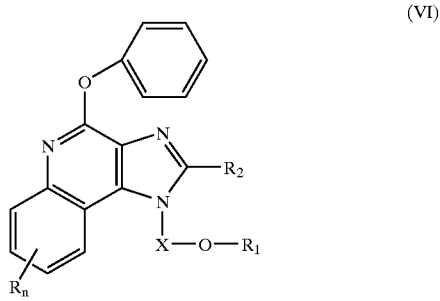

(VI)

wherein X is —$CHR_3$—, —$CHR_3$-alkyl-, or —$CHR_3$-alkenyl-;
  $R_1$ is selected from the group consisting of:
    -aryl;
    -alkenyl;
    —$R_4$-aryl; and
    —$(CH_2)_{1-10}$—C≡C—$R_{10}$;
  $R_2$ is selected from the group consisting of:
    -hydrogen;
    -alkyl;
    -alkenyl;
    -aryl;
    -heteroaryl;
    -heterocyclyl;
    -alkyl-Y-alkyl;
    alkyl-Y-alkenyl;
    alkyl-Y-aryl; and
    -alkyl or alkenyl substituted by one or more substituents selected from the group consisting of:
      —OH;
      -halogen;
      —$N(R_3)_2$;
      —CO—$N(R_3)_2$;
      —CO—$C_{1-10}$ alkyl;
      —CO—O—$C_{1-10}$ alkyl;
      —$N_3$;
      -aryl;
      -heteroaryl;
      -heterocyclyl;
      —CO-aryl; and
      —CO-heteroaryl;
  $R_4$ is alkyl or alkenyl, both of which may be interrupted by one or more —O— groups;
  each $R_3$ is independently H or $C_{1-10}$ alkyl;
  $R_{10}$ is selected from the group consisting of H, alkyl, alkenyl, aryl, and
  -alkylaryl;
  each Y is independently —O— or —$S(O)_{0-2}$—;
  n is 0 to 4; and
  each R present is independently selected from the group consisting of $C_{1-10}$ alkyl, $C_{1-10}$ alkoxy, hydroxy, halogen and trifluoromethyl;
or a pharmaceutically acceptable salt thereof.

Another class of intermediate compounds are the imidazoquinoline-N-oxide compounds of Formula (VII):

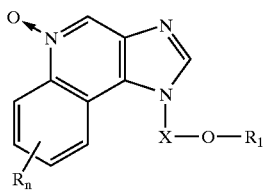

(VII)

wherein X is —CHR$_3$—, —CHR$_3$-alkyl-, or —CHR$_3$-alkenyl-;
  R$_1$ is selected from the group consisting of:
    -aryl;
    -alkenyl;
    —R$_4$-aryl; and
    —(CH$_2$)$_{1-10}$—C≡C—R$_{10}$;
  R$_4$ is alkyl or alkenyl, both of which may be interrupted by one or more —O— groups;
  each R$_3$ is independently H or C$_{1-10}$ alkyl;
  R$_{10}$ is selected from the group consisting of H, alkyl, alkenyl, aryl, and -alkylaryl;
  n is 0 to 4; and
  each R present is independently selected from the group consisting of C$_{1-10}$ alkyl, C$_{1-10}$ alkoxy, hydroxy, halogen and trifluoromethyl;
  or a pharmaceutically acceptable salt thereof.

An additional class of intermediate compounds has the Formula (VIII):

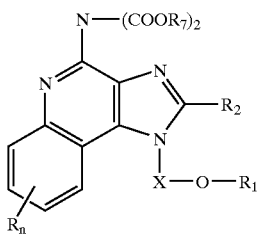

(VIII)

wherein X is —CHR$_3$—, —CHR$_3$-alkyl-, or —CHR$_3$-alkenyl-;
  R$_1$ is selected from the group consisting of:
    -aryl;
    -alkenyl;
    —R$_4$-aryl; and
    —(CH$_2$)$_{1-10}$—C≡C—R$_{10}$;
  R$_2$ is selected from the group consisting of:
    -hydrogen;
    -alkyl;
    -alkenyl;
    -aryl;
    -heteroaryl;
    -heterocyclyl;
    -alkyl-Y-alkyl;
    -alkyl-Y-alkenyl;
    -alkyl-Y-aryl; and
    -alkyl or alkenyl substituted by one or more substituents selected from the group consisting of:
      —OH;
      -halogen;
      —N(R$_3$)$_2$;
      —CO—N(R$_3$)$_2$;
      —CO—C$_{1-10}$ alkyl;
      —CO—O—C$_{1-10}$ alkyl;
      —N$_3$;
      -aryl;
      -heteroaryl;
      -heterocyclyl;
      —CO-aryl; and
      —CO-heteroaryl;
  R$_4$ is alkyl or alkenyl, which may be interrupted by one or more —O— groups;
  each R$_3$ is independently H or C$_{1-10}$ alkyl;
  R$_{10}$ is selected from the group consisting of H, alkyl, alkenyl, aryl, and -alkylaryl;
  each Y is independently —O— or —S(O)$_{0-2}$—;
  n is 0 to 4;
  each R present is independently selected from the group consisting of C$_{1-10}$ alkyl, C$_{1-10}$ alkoxy, hydroxy, halogen and trifluoromethyl; and
  R$_7$ is tert-butyl or benzyl;
  or a pharmaceutically acceptable salt thereof.

A further class of intermediates are imidazoquinoline-4-chloro compounds of the Formula (IX)

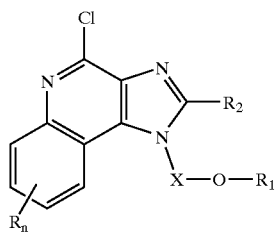

(IX)

wherein: X is —CHR$_3$—, —CHR$_3$-alkyl-, or —CHR$_3$-alkenyl-;
  R$_1$ is selected from the group consisting of:
    aryl;
    alkenyl;
    R$_4$-aryl; and
    —(CH$_2$)$_{1-10}$—C≡CH
  R$_2$ is selected from the group consisting of:
    -hydrogen;
    -alkyl;
    -alkenyl;
    -aryl;
    -heteroaryl;
    -heterocyclyl;
    -alkyl-Y-alkyl;
    -alkyl-Y-alkenyl;
    -alkyl-Y-aryl; and
    -alkyl or alkenyl substituted by one or more substituents selected from the group consisting of:
      —OH;
      -halogen;
      —N(R$_3$)$_2$;
      —CO—N(R$_3$)$_2$;
      —CO—C$_{1-10}$ alkyl;
      —CO—O—C$_{1-10}$ alkyl;
      —N$_3$;
      -aryl;
      -heteroaryl;
      -heterocyclyl;
      —CO-aryl; and
      —CO-heteroaryl;
  R$_4$ is alkyl or alkenyl, which may be interrupted by one or more —O— groups;

each $R_3$ is independently H or $C_{1-10}$ alkyl;
each Y is independently —O— or —S(O)$_{0-2}$—;
n is 0 to 4; and
each R present is independently selected from the group consisting of $C_{1-10}$ alkyl, $C_{1-10}$ alkoxy, hydroxy, halogen and trifluoromethyl;

or a pharmaceutically acceptable salt thereof.

As used herein, the terms "alkyl", "alkenyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Where "alkyl" and "alkenyl" are shown with two bonds, i.e. -alkyl- and -alkenyl-, they are understood to be alkylene and alkenylene groups, respectively. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, cyclopropylmethyl, and adamantyl.

In addition, the alkyl and alkenyl portions of —X— groups can be unsubstituted or substituted by one or more substituents, which substituents are selected from the group consisting of alkyl, alkenyl, aryl, heteroaryl, heterocyclyl, arylalkyl, heteroarylalkyl, and heterocyclylalkyl.

The term "haloalkyl" is inclusive of groups that are substituted by one or more halogen atoms, including perfluorinated groups. This is also true of groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

"Heterocyclyl" includes non-aromatic rings or ring systems that contain at least one ring hetero atom (e.g., O, S, N) and includes all of the fully saturated and partially unsaturated derivatives of any of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, and the like.

The aryl, heteroaryl, and heterocyclyl groups can be unsubstituted or substituted by one or more substituents independently selected from the group consisting of alkyl, alkoxy, alkylthio, haloalkyl, haloalkoxy, haloalkylthio, halogen, nitro, nitrilo, hydroxy, mercapto, cyano, carboxy, formyl, aryl, aryloxy, arylthio, arylalkoxy, arylalkylthio, heteroaryl, heteroaryloxy, heteroarylthio, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, aroyloxy, aroylthio, aroylamino, alkylaminosulfonyl, alkylsulfonyl, arylsulfonyl, heteroarylsulfonyl, alkylcarbonylamino, alkenylcarbonylamino, arylcarbonylamino, arylalkylcarbonylamino, heteroarylcarbonylamino, heteroarylalkylcarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylaminocarbonylamino, and, in the case of heterocyclyl, oxo. If any other groups are identified as being "substituted" or "optionally substituted", then those groups can also be substituted by one or more of the above enumerated substituents.

Certain substituents are generally preferred. For example, $R_4$-aryl is a preferred $R_1$ group and preferred $R_{10}$ groups are alkyl and aryl, with phenyl or substituted phenyl being a preferred aryl group. Preferably no R substituents are present (i.e., n is 0). Preferred $R_2$ groups include hydrogen, alkyl groups having 1 to 4 carbon atoms (i.e., methyl, ethyl, propyl, isopropyl, n-butyl, sec-butyl, isobutyl, and cyclopropylmethyl), methoxyethyl, and ethoxymethyl. For substituted groups such as substituted alkyl or substituted aryl groups, preferred substituents include halogen, nitrile, nitro, carboxy, methoxy, methylthio, trifluoromethyl, and trifluoromethoxy. One or more of these preferred substituents, if present, can be present in the compounds of the invention in any combination.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers.

Pharmaceutical Compositions and Biological Activity

Pharmaceutical compositions of the invention contain a therapeutically effective amount of a compound of the invention as described above in combination with a pharmaceutically acceptable carrier.

The term "a therapeutically effective amount" means an amount of the compound sufficient to induce a therapeutic effect, such as cytokine induction, antitumor activity, and/or antiviral activity. Although the exact amount of active compound used in a pharmaceutical composition of the invention will vary according to factors known to those of skill in the art, such as the physical and chemical nature of the compound, the nature of the carrier, and the intended dosing regimen, it is anticipated that the compositions of the invention will contain sufficient active ingredient to provide a dose of about 100 ng/kg to about 50 mg/kg, preferably about 10 μg/kg to about 5 mg/kg, of the compound to the subject. Any of the conventional dosage forms may be used, such as tablets, lozenges, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, etc.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, IL-6, IL-10 and IL-12, and a variety of other cytokines. Among other effects, these and other cytokines can inhibit virus production and tumor cell growth, making the compounds useful in the treatment of viral diseases and tumors. Accordingly, the invention provides a method of inducing cytokine biosynthesis in an animal comprising administering an effective amount of a compound or composition of the invention to the animal.

Certain compounds of the invention have been found to preferentially induce the expression of IFN-α in a population of hematopoietic cells such as PBMCs (peripheral blood mononuclear cells) containing pDC2 cells (precursor dendritic cell-type 2) without concomitant production of significant levels of inflammatory cytokines.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulate secretion of nitric oxide and the production of additional cytokines. Further, the compounds may cause proliferation and differentiation of B-lymphocytes.

Compounds of the invention also have an effect on the acquired immune response. For example, although there is not believed to be any direct effect on T cells or direct induction of T cell cytokines, the production of the T helper type 1 (Th1) cytokine IFN-γ is induced indirectly and the production of the T helper type 2 (Th2) cytokines IL-4, IL-5 and IL-13 are inhibited upon administration of the compounds. This activity means that the compounds are useful in the treatment of diseases where upregulation of the Th1 response and/or downregulation of the Th2 response is desired. In view of the ability of compounds of the invention to inhibit the Th2 immune response, the compounds are expected to be useful in the treatment of atopic diseases, e.g., atopic dermatitis, asthma, allergy, allergic rhinitis; systemic lupus erythematosis; as a vaccine adjuvant for cell mediated immunity; and possibly as a treatment for recurrent fungal diseases and chlamydia.

The immune response modifying effects of the compounds make them useful in the treatment of a wide variety of conditions. Because of their ability to induce the production of cytokines such as IFN-α and/or TNF-α, the compounds are particularly useful in the treatment of viral diseases and tumors. This immunomodulating activity suggests that compounds of the invention are useful in treating diseases such as, but not limited to, viral diseases including genital warts; common warts; plantar warts; Hepatitis B; Hepatitis C; Herpes Simplex Virus Type I and Type II; molluscum contagiosum; variola, particularly variola major; rhinovirus; adenovirus; influenza; para-influenza; HIV; CMV; VZV; intraepithelial neoplasias such as cervical intraepithelial neoplasia; human papillomavirus (HPV) and associated neoplasias; fungal diseases, e.g. candida, aspergillus, and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g. pneumocystis carnii, cryptosporidiosis, histoplasmosis, toxoplasmosis, trypanosome infection, and leishmaniasis; and bacterial infections, e.g., tuberculosis, and mycobacterium avium. Additional diseases or conditions that can be treated using the compounds of the invention include actinic keratosis; eczema; eosinophilia; essential thrombocythaemia; leprosy; multiple sclerosis; Ommen's syndrome; discoid lupus; Bowen's disease; Bowenoid papulosis; alopecia areata; the inhibition of keloid formation after surgery and other types of post-surgical scars. In addition, these compounds could enhance or stimulate the healing of wounds, including chronic wounds. The compounds may be useful for treating the opportunistic infections and tumors that occur after suppression of cell mediated immunity in, for example, transplant patients, cancer patients and HIV patients.

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased over the background level of such cytokines. The precise amount will vary according to factors known in the art but is expected to be a dose of about 100 ng/kg to about 50 mg/kg, preferably about 10 μg/kg to about 5 mg/kg.

The invention also provides a method of treating a viral infection in an animal and a method of treating a neoplastic disease in an animal comprising administering an effective amount of a compound or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose of about 100 ng/kg to about 50 mg/kg, preferably about 10 μg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

The invention is further described by the following examples, which are provided for illustration only and are not intended to be limiting in any way.

EXAMPLES

In the examples below some of the compounds were purified using semi-preparative HPLC. Two different methods were used and they are described below. Both methods used a A-100 Gilson-6 equipped with 900 Series Intelligent Interface. The semi-prep HPLC fractions were analyzed by LC-APCI/MS and the appropriate fractions were combined and lyophilized to provide the trifluoroacetate salt of the desired compound.

Method A

Column: column Microsorb C18, 21.4×250 mm, 8 micron particle size, 60 A pore; flow rate: 10 mL/min.; gradient elution from 2–95% B in 25 min., hold at 95% B for 5 min., where A=0.1% trifluoroacetic acid/water and B=0.1% trifluoroacetic acid/acetonitrile; peak detection at 254 nm for triggering fraction collection.

Method B

Column: Phenomenex Capcell PakC18, 35×20 mm, 5 micron particle size; flow rate: 20 mL/min.; gradient elution from 5–95% B in 10 min., hold at 95% B for 2 min., where A=0.1% trifluoroacetic acid/water and B=0.1% trifluoroacetic acid/acetonitrile; peak detection at 254 nm for triggering fraction collection.

Example 1

1-[2-(2-Propynyloxy)ethyl]-1H-imidazo[4,5-c]quinolin-4-amine

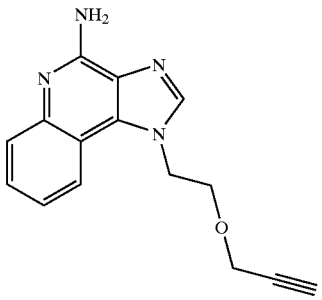

Part A 2-(1H-Imidazo[4,5-c]quinolin-1-yl)-1-ethanol (28.5 g, 0.133 mol) was added in portions over a period of 1 hour to a mixture of sodium hydroxide (240 mL of 50%), dichloromethane (240 mL), propargyl bromide (39.6 g of 80%, 0.266 mol) and benzyltrimethylammonium chloride (2.46 g, 0.013 mmol). The resulting reaction mixture was allowed to stir at ambient temperature for 16 hours. The layers were separated. The aqueous fraction was extracted with additional dichloromethane. The organic fractions were combined, washed with water, dried over magnesium sulfate and then concentrated under reduced pressure. The resulting residue was combined with diethyl ether and the mixture was allowed to stir. An orange solid was isolated by filtration. This material was recrystallized from ethyl acetate to provide 19.8 g of 2-(1H-imidazo[4,5-c]quinolin-1-yl)ethyl (2-propynyl) ether as a yellow crystalline solid, m.p. 124–126° C.

Analysis. Calculated for $C_{15}H_{13}N_3O$: % C, 71.70; % H, 5.21; % N, 16.72. Found: % C, 71.85; % H, 5.25; % N, 16.90

$^1$H NMR (300 MHz, DMSO) δ 9.21 (s, 1H), 8.44 (m, 1H), 8.36 (s, 1H), 8.18 (m, 1 H), 7.71 (m, 2H), 4.93 (t, J=5.1 Hz, 2H), 4.14 (d, J=2.4 Hz, 2H), 3.98 (t, J=5.1 Hz, 2 H), 3.35 (t, J=2.2 Hz, 1H)

HRMS(ESI) Calculated for $C_{15}H_{14}N_3O$ (MH$^+$) 252.1137, found 252.1141

Part B 2-(1H-Imidazo[4,5-c]quinolin-1-yl)ethyl (2-propynyl) ether (19.7 g, 78.4 mmol) and chloroform were combined and then cooled to 0° C. 3-Chloroperoxybenzoic acid (15.7 g of 57–86%) was added and the mixture was allowed to stir for 0.5 hour. The mixture was allowed to warm to ambient temperature by which time all material was in solution. Analysis by thin layer chromatography (TLC) indicated that some starting material was still present so more 3-chloroperoxybenzoic acid (two separate 4 g portions) was added. About 0.5 hour after the second portion was added, TLC showed no starting material. The reaction solution was extracted with 10% sodium hydroxide. The aqueous fraction was then extracted multiple times with dichloromethane. The organic fractions were combined, dried over magnesium sulfate, filtered and then concentrated under reduced pressure to provide 18.5 g of 1-[2-(2-propynyloxy)ethyl]-1H-imidazo[4,5-c]quinoline-5N-oxide as a yellow oil.

HRMS(ESI) Calculated for $C_{15}H_{14}N_3O_2$ (MH$^+$) 268.1086, found 268.1098

Part C

Under a nitrogen atmosphere trichloroacetyl isocyanate (15.5 g, 82.2 mmol) was added dropwise to a mixture of 1-[2-(2-propynyloxy)ethyl]-1H-imidazo[4,5-c]quinoline-5N-oxide (18.3 g, 68.5 mmol) and dichloromethane (300 mL). Vigorous carbon dioxide evolution was observed. After about 0.5 hour all of the material was in solution. The reaction solution was allowed to stir for about 1 hour at which time analysis by TLC indicated the presence of a small amount of starting material. More trichloroacetyl isocyanate (4.5 g) was added. After 1 hour, TLC analysis indicated that the reaction was complete. The volatiles were removed under reduced pressure to provide N-{1-[2-(2-propynyloxy)ethyl]-1H-imidazo[4,5-c]quinolin-4-yl}-2,2,2-trichloroacetamide as a pale yellow solid.

Part D

Dichloromethane (150 mL) was added to a mixture of the solid from Part C and methanol (200 mL) and all of the material went into solution. Sodium methoxide (50 g of 25% in methanol) was added and the solution was allowed to stir at ambient temperature overnight. The resulting precipitate was isolated by filtration. The filtrate was concentrated to a volume of approximately 100 mL and a second crop of precipitate was isolated by filtration. The two crops were combined and dried in a vacuum oven at 60° C. for 16 hours to provide 16.4 g of 1-[2-(2-propynyloxy)ethyl]-1H-imidazo[4,5-c]quinolin-4-amine as an off-white solid, m.p. 225–227° C.

Analysis. Calculated for $C_{15}H_{14}N_4O$ $(H_2O)_{1/4}$: % C, 66.53; % H, 5.40; % N, 20.69. Found: % C, 66.33; % H, 5.18; % N, 21.12

$^1$H NMR (300 MHz, DMSO) δ 8.13 (s, 1H), 8.08 (br d, J=7.8 Hz, 1H), 7.62 (br d, J=8.3 Hz, 1H), 7.44 (br t, J=7.6 Hz, 1H), 7.24 (br t, J=7.5 Hz, 1H), 6.54 (s, 2H), 4.81 (t, J=5.4 Hz, 2H), 4.14 (d, J=2.4 Hz, 2H), 3.93 (t, J=5.1 Hz, 2H), 3.38 (t, J=2.4 Hz, 1H)

HRMS(ESI) Calculated for $C_{15}H_{15}N_4O$ (MH$^+$) 267.1246, found 267.1253

Example 2

2-{3-[2-(4-Amino-1H-imidazo[4,5-c]quinolin-1-yl)ethoxy]-1-propynyl}benzonitrile

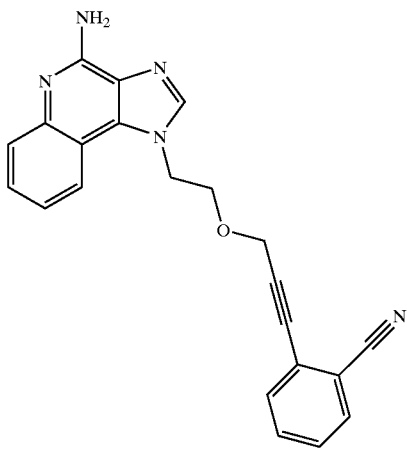

Part A

Under a nitrogen atmosphere 1-[2-(2-propynyloxy)ethyl]-1H-imidazo[4,5-c]quinolin-4-amine (16 g, 60.1 mmol), di-tert-butyl dicarbonate (32.7 g, 150 mmol), triethylamine (21 mL, 150 mol), N,N-dimethylformamide (150 mL) and 4-(dimethylamino) pyridine (0.1 g) were combined and heated to 80–85° C. After about 1 hour the mixture became homogeneous and TLC analysis indicated that very little starting material remained. The solution was heated for an additional hour. The solution was diluted with ethyl acetate and water. The layers were separated and the aqueous fraction was extracted with ethyl acetate. The organic fractions were combined, washed with water and then with brine, dried over magnesium sulfate, filtered and then concentrated under reduced pressure to provide a pale orange-yellow solid. This material was triturated with diethyl ether to provide 22.6 g of N,N-(bis tert-butoxycarbonyl)-1-[2-(2-propynyloxy)ethyl]-1H-imidazo[4,5-c]quinolin-4-amine as an off-white solid, m.p. 139–142° C.

Analysis. Calculated for $C_{25}H_{30}N_4O_5$: % C, 64.36; % H, 6.48; % N, 12.01. Found: % C, 64.40; % H, 6.43; % N, 12.06

$^1$H NMR (300 MHz, DMSO) δ 8.44 (m, 1H), 8.35 (s, 1H), 8.08 (m, 1H), 7.73 (m, 2H), 4.94 (t, J=4.9 Hz, 2H), 4.12 (d, J=2.4 Hz, 2H), 3.98 (t, J=5.1 Hz, 2H), 3.31 (t, J=2.4 Hz, 1H), 1.34 (s, 18H)

HRMS(ESI) calcd for $C_{25}H_{31}N_4O_5$ (MH$^+$) 467.2294, found 467.2307

Part B

Under a nitrogen atmosphere 2-iodobenzonitrile (0.54 g, 2.35 mmol), dichlorobis(triphenylphosphine)palladium(II) (0.09 g, 0.13 mmol), and copper(I) iodide (0.05 g, 0.26 mmol) were added to a mixture of N,N-(bis tert-butoxycarbonyl)-1-[2-(2-propynyloxy) ethyl]-1H-imidazo[4,5-c]quinolin-4-amine (1.0 g, 2.14 mmol) and anhydrous N,N-dimethylformamide (25 mL). After 2 hours the reaction mixture was slowly poured into water. The resulting precipitate was collected and dried at 35° C. for 16 hours to provide 1.18 g of 2-(3-{2-[4-(bis tert-butoxycarbonyl)amino-1H-imidazo[4,5-c]quinolin-1-yl]ethoxy}-1-propynyl)benzonitrile as a solid.

$^1$H NMR (300 MHz, DMSO) δ 8.47 (d, J=6.8 Hz, 1H), 8.39 (s, 1H), 8.06 (d, J=7.8 Hz, 1H), 7.87 (d, J=7.3 Hz, 1H), 7.40–7.80 (m, 4H), 7.34 (d, J=7.3 z, 1H), 5.00 (br s, 2H), 4.47 (br s, 2H), 4.13 (s, 2H), 1.31 (s, 18H)

HRMS(ESI) Calculated for $C_{32}H_{34}N_5O_5$ (MH$^+$) 568.2560, found 568.2565

Part C

Trifluoroacetic acid (20 mL) was added to a solution of the material from Part B in dichloromethane (20 mL). After 4 hours the reaction mixture was diluted with dichloromethane containing a small amount of methanol and 20% sodium hydroxide. The layers were separated. The aqueous fraction was extracted with dichloromethane. The organic fractions were combined, dried over magnesium sulfate, filtered and then concentrated under reduced pressure to provide a yellow powder. This material was purified by flash chromatography eluting with 9/1 dichloromethane/methanol to provide 0.48 g of 2-{3-[2-(4-amino-1H-imidazo[4,5-c]quinolin-1-yl)ethoxy]-1-propynyl}benzonitrile as a white powder, m.p. 180–183° C.

Analysis. Calculated for $C_{22}H_{17}N_5O.(H_2O)_{2/5}$: % C, 70.54; % H, 4.79; % N, 18.70. Found: % C, 70.61; % H, 4.75; % N, 18.70

$^1$H NMR (300 MHz, DMSO) δ 8.19 (s, 1H), 8.12 (d, J=8.3 Hz, 1H), 7.88 (d, J=7.8 Hz, 1H), 7.55–7.75 (m, 3H), 7.40–7.50 (m, 2H), 7.24 (br t, J=7.5 Hz, 1H), 6.68 (br s, 2H), 4.87 (t, J=5.1 Hz, 2H), 4.50 (s, 2H), 4.09 (t, J=5.1 Hz, 2H)

Example 3

1-{2-[(3-Phenyl-2-propynyl)oxy]ethyl}-1H-imidazo[4,5-c]quinolin-4-amine

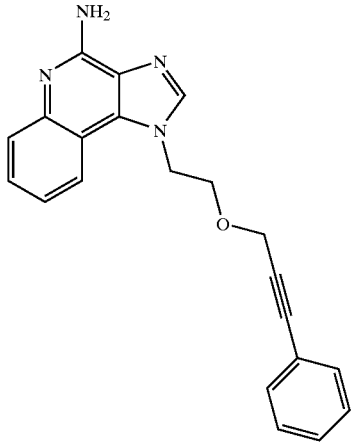

Under a nitrogen atmosphere, a mixture of 1-[2-(2-propynyloxy)ethyl]-1H-imidazo[4,5-c]quinolin-4-amine (10 g, 37.6 mmol), anhydrous N,N-dimethylformamide (150 mL) and potassium carbonate (6.23 g, 45.1 mmol) was heated to 70° C. Iodobenzene (4.43 mL, 39.5 mmol), dichlorobis(triphenylphosphine)palladium(II) (0.53 g, 0.75 mol), and copper(I) iodide (0.29 g, 1.50 mmol) were added and the mixture was allowed to stir for 0.5 hour. The temperature was raised to about 85° C. After 1.5 hours analysis by HPLC (reverse phase, acetonitrile/water with 0.1% trifluoroacetic acid) indicated that the reaction was complete. The mixture was allowed to cool to ambient temperature and then it was filtered. The filtrate was concentrated under reduced pressure. The residue was purified twice by flash chromatography (95/5 dichloromethane/methanol) to provide 2.7 g of 1-{2-[(3-phenyl-2-propynyl)oxy]ethyl}-1H-imidazo[4,5-c]quinolin-4-amine as a white solid, m.p. 196–197° C.

Analysis. Calculated for $C_{21}H_{18}N_4O$: % C, 73.67; % H, 5.30; % N, 16.36. Found: % C, 73.29; % H, 5.23; % N, 16.35

$^1$H NMR (300 MHz, DMSO) δ 8.17 (s, 1H), 8.12 (d, J=7.4 Hz, 1H), 7.63 (dd, J=8.3, 0.9 Hz, 1H), 7.44 (t, J=7.5 Hz, 1H), 7.15–7.40 (m, 6H), 6.60 (s, 2H), 4.86 (t, j=5.1 Hz, 2H), 4.39 (s, 2H), 4.03 (t, J=5.1 Hz, 2H)

HRMS(EI) Calculated for $C_{21}H_{18}N_4O$ (M$^+$) 342.1481, found 342.1490

Example 4

1-{2-[(3-Phenyl-2-propynyl)oxy]ethyl}-1H-imidazo[4,5-c]quinolin-4-amine Hydrochloride 1-{2-[(3-Phenyl-2-propynyl)oxy]ethyl}-1H-imidazo[4,5-c]quinolin-4-amine (1.0 g, 2.92 mmol) was dissolved in a mixture of methanol (15 mL) and dichloromethane (5 mL). Hydrogen chloride/diethyl ether (10 mL of 1M) was added and the reaction solution was allowed to stir for 16 hours by which time a precipitate had formed. The mixture was concentrated under reduced pressure to provide a solid. This material was recrystallized from acetonitrile containing a small amount of methanol to provide 0.52 g of 1-{2-[(3-phenyl-2-propynyl)oxy]ethyl}-1H-imidazo[4,5-c]quinolin-4-amine hydrochloride as an off-white crystalline solid, m.p. 231–236° C.

Analysis. Calculated for $C_{21}H_{19}ClN_4O\cdot(H_2O)_{1/4}$: % C, 65.79; % H, 5.13; % N, 14.61. Found: % C, 65.72; % H, 5.0; % N, 14.73

$^1$H NMR (300 MHz, DMSO) δ 8.49 (s, 1H), 8.34 (d, J=8.3 Hz, 1H), 7.81 (br d, J=8.3 Hz, 1H), 7.72 (t, J=7.8 Hz, 1H), 7.56 (t, J=7.8 Hz, 1H), 7.30–7.40 (m, 3H), 7.14 (dd, J=8.0, 1.5 Hz, 2H), 4.94 (t, J=4.8 Hz, 2H), 4.38 (s, 2H), 4.05 (t, J=4.9 Hz, 2H)

HRMS (EI) Calculated for $C_{21}H_{18}N_4O$ (M$^+$) 342.1481, found 342.1485

Example 5

1-{2-[3-(4-Methoxyphenyl)propoxy]ethyl}-1H-imidazo[4,5-c]quinolin-4-amine

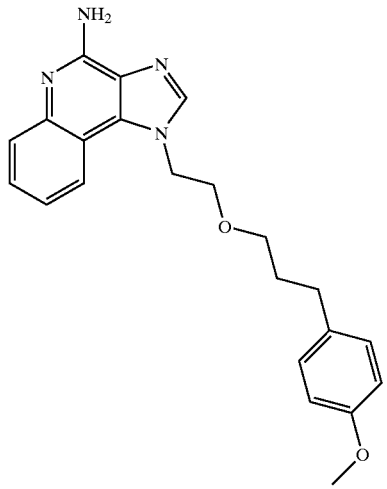

Part A

Under a nitrogen atmosphere, N,N-(bis tert-butoxycarbonyl)-1-[2-(2-propynyloxy)ethyl]-1H-imidazo[4,5-c]quinolin-4-amine (1.0 g, 2.14 mmol), triethylamine (0.8 mL, 5.56 mmol), 4-iodoanisole (0.51 g, 2.18 mmol) and anhydrous N,N-dimethylformamide (15 mL) were combined. Dichlorobis(triphenylphosphine)palladium(II) (0.09 g, 0.13 mol) and copper(I) iodide (0.05 g, 0.26 mmol) were added and the reaction mixture was stirred for 1 hour at ambient temperature at which time analysis by HPLC (reverse phase, acetonitrile/water) indicated that the reaction was complete. The reaction mixture was partitioned between ethyl acetate and aqueous sodium bicarbonate. The organic fraction was washed with water and then with brine, dried over magnesium sulfate, filtered and then concentrated under reduced pressure to provide 0.95 g of N,N-(bis tert-butoxycarbonyl)-1-(2-{[3-(4-methoxyphenyl)-2-propynyl]oxy}ethyl)-1H-imidazo[4,5-c]quinolin-4-amine as an orange solid.

HRMS(EI) Calculated for $C_{32}H_{36}N_4O_6$ (M$^+$) 572.2635, found 572.2635

Part B

N,N-(Bis tert-butoxycarbonyl)-1-(2-{[3-(4-methoxyphenyl)-2-propynyl]oxy}ethyl)-1H-imidazo[4,5-c]quinolin-4-amine (0.75 g, 1.31 mmol), ethyl acetate (25 mL) and catalyst (100 mg of 5% Pd/C with 50% water) were combined and then hydrogenated on a Parr apparatus at 40 psi (2.8 Kg/cm$^2$). No reaction occurred. Platinum oxide (150 mg) and methanol (10 mL) were added and the mixture was hydrogenated at 45 psi (3.15 Kg/cm$^2$) for 1 hour. Hydrogen consumption was observed immediately. The reaction mixture was filtered to remove the catalyst. The filtrate was concentrated under reduced pressure to provide N,N-(bis tert-butoxycarbonyl)-1-{2-[3-(4-methoxyphenyl)propoxy]ethyl}-1H-imidazo[4,5-c]quinolin-4-amine as a yellow-brown gum.

HRMS(EI) Calculated for $C_{32}H_{40}N_4O_6$ (M$^+$) 576.2948, found 576.2965

Part C

Under a nitrogen atmosphere trifluoroacetic acid (10 mL) was added to a mixture of the material from Part B and dichloromethane (10 mL). The resulting solution was allowed to stir for 4 hours. The solution was concentrated under reduced pressure. The residue was partitioned between 50% aqueous sodium hydroxide and dichloromethane containing a small amount of methanol. The organic fraction was dried over magnesium sulfate, filtered and then concentrated under reduced pressure to provide a tan foam. The foam was purified by flash chromatography (9/1 dichloromethane/methanol) to provide a light yellow glass. The glass was triturated with diethyl ether to provide a white powder. This material was dried in a vacuum oven for 4 hours at 60° C. to provide 0.41 g of 1-{2-[3-(4-methoxyphenyl)propoxy]ethyl}-1H-imidazo[4,5-c]quinolin-4-amine as a white solid, m.p. 116–118° C.

Analysis. Calculated for $C_{22}H_{24}N_4O_2$: % C, 70.19; % H, 6.43; % N, 14.88. Found: % C, 69.79; % H, 6.40; % N, 14.73

$^1$H NMR (300 MHz, DMSO) δ 8.17 (s, 1H), 8.12 (d, J=8.3 Hz, 1H), 7.64 (d, J=8.3 Hz, 1H), 7.45 (t, J=7.8 Hz, 1H), 7.24 (t, J=7.6 Hz, 1H), 6.80 (d, J=8.8 Hz, 2H), 6.66 (d, J=8.8 Hz, 2H), 6.60 (s, 2H), 4.80 (t, J=5.1 Hz, 2H), 3.81 (t, J=4.9 Hz, 2H), 3.66 (s, 3H), 3.27 (t, J=6.1 Hz, 2H), 2.32 (t, J=7.3 Hz, 2H), 1.60 m, 2H)

Example 6

$N^1$,4-Dimethyl-3-{3-[2-(4-amino-1H-imidazo[4,5-c]quinolin-1-yl)ethoxy]propyl}-1-benzensulfonamide

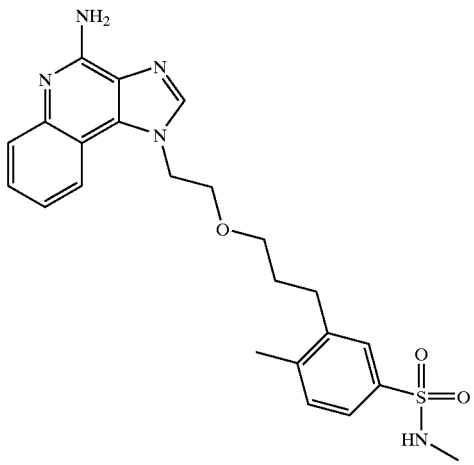

Part A

Under a nitrogen atmosphere, 1-[2-(2-propynyloxy)ethyl]-1H-imidazo[4,5-c]quinolin-4-amine (1.7 g, 6.35 mmol), dibenzyl dicarbonate (4.55 g, 15.9 mmol), triethylamine (1.8 mL, 13.0 mmol), 4-(dimethylamino)pyridine and anhydrous N,N-dimethylformamide (20 mL) were combined. The reaction mixture was heated to 90° C. at which time the reaction turned homogeneous. It was then heated to 130° C. for 4 hours. The reaction mixture was allowed to cool and then it was partitioned between dichloromethane and water. The aqueous fraction was extracted with dichloromethane. The organic fractions were combined, dried over magnesium sulfate and then concentrated to a volume of ~10 mL. The concentrate was allowed to stand over the weekend and then it was diluted with toluene. The resulting precipitate was isolated by filtration and identified as starting material. The filtrate was diluted with diethyl ether. The resulting precipitate was isolated by filtration to provide 1.1 g of benzyl N-{1-[2-(propynyloxy)ethyl]-1H-imidazo[4,5-c]quinolin-4-yl}carbamate as a white solid.

$^1$H NMR (300 MHz, DMSO) δ 9.98 (s, 1H), 8.34 (d, J=7.8 Hz, 1H), 8.30 (s, 1H), 7.97 (d, J=7.3 Hz, 1H), 7.70 (t, J=7.8 Hz, 1H), 7.58 (t, J=7.8 Hz, 1H), 7.15–7.50 (m, 5H), 5.21 (s, 2H), 4.90 (t, J=5.1 Hz, 2H), 4.14 (d, J=2.4 Hz, 2H), 3.96 (t, J=4.9 Hz, 2H), 3.38 (t, J=2.4 Hz, 2H)

Part B

Under a nitrogen atmosphere benzyl N-{1-[2-(propynyloxy)ethyl]-1H-imidazo[4,5-c]quinolin-4-yl}carbamate (0.37 g, 0.91 mmol), 3-iodo-4-methyl-1-benzenesulfonamide (0.3 g, 0.96 mmol), triethylamine (0.2 mL, 1.36 mmol) and anhydrous acetonitrile (20 mL) were combined. Dichlorobis(triphenylphosphine)palladium(II) (13 mg, 0.018 mol) and copper(I) iodide (7 mg, 0.036 mmol) were added and the reaction solution was heated to ~45° C. After 3 hours analysis by reverse phase HPLC indicated that the reaction was complete. The reaction solution was concentrated under reduced pressure and the residue was purified by flash chromatography (98/2 to 95/5 dichloromethane/methanol) to provide 0.33 g of benzyl N-(1-{2-[(3-{2-methyl-5-[(methylamino)sulfonyl]phenyl}-2-propynyl)oxy]ethyl}-1H-imidazo[4,5-c]quinolin-4-yl)carbamate as a pale yellow solid.

$^1$H NMR (300 MHz, DMSO) δ 9.96 (s, 1H), 8.36 (m, 2H), 7.96 (d, J=8.3 Hz, 1H), 7.55–7.70 (m, 4H), 7.48 (m, 2H), 7.30–7.45 (m, 5H), 5.21 (s, 2H), 4.95 (t, J=4.6 Hz, 2H), 4.40 (s, 2H), 4.06 (t, J=5.1 Hz, 2H), 2.54 (s, 3H), 2.40 (d, J=4.9 Hz, 3H)

MS (CI) 584, 476

Part C

Platinum on carbon (0.08 g of 10%) was added to a mixture of benzyl N-(1-{2-[(3-{2-methyl-5-[(methylamino)sulfonyl]phenyl}-2-propynyl)oxy]ethyl}-1H-imidazo[4,5-c]quinolin-4-yl)carbamate (0.3 g, 0.51 mmol) and methanol (10 mL). The mixture was hydrogenated on a Parr apparatus at 40 psi (2.8 Kg/cm$^2$) for 16 hours. Analysis by LC-MS indicated alkyne reduction but no phenoxycarbonyl removal. Palladium on carbon (0.1 g of 10%) was added and the reaction mixture was hydrogenated at 40 psi (2.8 Kg/cm$^2$) for 8 hours. Analysis by LC-MS indicated only a small amount of phenoxycarbonyl removal. Palladium black (0.1 g) was added and the reaction mixture was hydrogenated at 40 psi (2.8 Kg/cm$^2$) for 16 hours. Analysis by LC-MS indicated one major product with a mass consistent with the desired product. The reaction mixture was filtered and the filtrate was washed with methanol and dichloromethane. The solvents were removed under reduced pressure to provide an off-white powder. This material was recrystallized from acetonitrile to provide 0.11 g of N$^1$,4-dimethyl-3-{3-[2-(4-amino-1H-imidazo[4,5-c]quinolin-1-yl)ethoxy]propyl}-1-benzensulfonamide as a light yellow crystalline solid, m.p. 207–209° C.

Analysis. Calculated for $C_{23}H_{27}N_5O_3S$: % C, 60.91; % H, 6.00; % N, 15.44. Found: % C, 60.87; % H, 5.75; % N, 15.51

$^1$H NMR (300 MHz, DMSO) δ 8.16 (s, 1H), 8.12 (d, J=8.3 Hz, 1H), 7.62 (d, J=8.3 Hz, 1H), 7.53 (d, J=1.5 Hz, 1H), 7.44 (br t, J=7.6 Hz, 1H), 7.38 (m, 1H), 7.24 (br t, J=7.6 Hz, 1H), 7.16 (d, 7.8 Hz, 1H), 7.02 (dd, J=7.8, 2.0 Hz, 1H), 6.58 (s, 2H), 4.80 (t, 5.2 Hz, 2H), 3.82 (t, 5.2 Hz, 2H), 3.31 (t, 5.9 Hz, 2H), 2.47 (s, 3H), 2.37 (d, 4.4 Hz, 2H), 1.65 (m, 2H)

HRMS(EI) Calculated for $C_{23}H_{27}N_5O_3S$ (M$^+$) 453.1835, found 453.1834

Example 7

1-(2-{[3-(2-Isopropylphenyl)-2-propynyl]oxy}ethyl)-1H-imidazo[4,5-c]quinolin-4-amine Hydrochloride

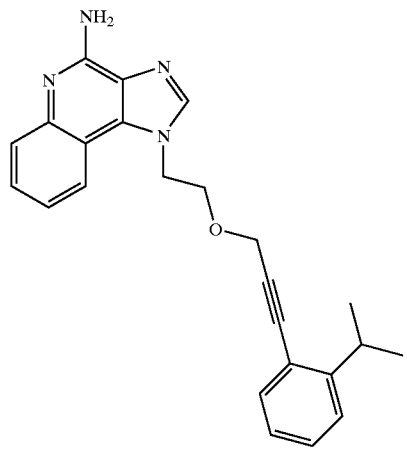

Under a nitrogen atmosphere 1-[2-(2-propynyloxy)ethyl]-1H-imidazo[4,5-c]quinolin-4-amine (0.50 g, 1.88 mmol), 2-iodoisopropylbenzene (0.65 g, 2.63 mmol), triethylamine (0.68 mL, 4.88 mmol) and N,N-dimethylformamide (10 mL) were combined and then heated to 60° C. Copper (I) iodide (0.04 g) and dichlorobis(triphenylphosphine)palladium(II) (0.08 g) were added. After 1.5 hours analysis by TLC (9/1 dichloromethane/methanol) indicated that the reaction was complete. The reaction mixture was concentrated under reduced pressure. The residue was purified by column chromatography eluting with 9/1 dichloromethane/methanol. The product fractions were combined and concentrated under reduced pressure. The residue was purified by column chromatography eluting with 9/1 dichloromethane/methanol containing 0.5% concentrated ammonium hydroxide. The product fractions were combined and concentrated under reduced pressure to provide ~0.38 g of a solid. This material was combined with hydrogen chloride/diethyl ether (3.9 mL of 1.0 M), stirred overnight and then concentrated under reduced pressure. The residue was recrystallized from isopropanol/methanol, isolated by filtration and then dried to provide 0.24 g of 1-(2-{[3-(2-isopropylphenyl)-2-propynyl]oxy}ethyl)-1H-imidazo[4,5-c]quinolin-4-amine hydrochloride as a solid, m.p. 239–241° C.

Analysis. Calculated for $C_{24}H_{24}N_4O$ •HCl•(H$_2$O)$_{1/2}$: % C, 67.06; % H, 6.09; % N, 13.03. Found: % C, 67.07; % H, 6.00; % N, 13.09.

¹H NMR (300 MHz, DMSO-d6) δ 8.54 (s, 1H), 8.39 (d, J=8.1 Hz, 1H), 7.85 (d, J=8.2 Hz, 1H), 7.76 (t, J=7.2 Hz, 1H), 7.59 (t, J=8.0 Hz, 1H), 7.30–7.38 (m, 2H), 7.11–7.19 (m, 2H), 5.00 (t, J=4.7 Hz, 2H), 4.47 (s, 2H), 4.10 (t, J=4.7 Hz, 2H), 3.16 (m, 1H), 1.13 (d, J=6.9 Hz, 6H)

IR (KBr) 3363, 3111, 2957, 1672, 753 cm⁻¹

HRMS (EI) Calculated for $C_{24}H_{24}N_4O$ (M⁺) 384.1950, found 384.1943

Example 8

1-(2-{[3-(2,6-Dimethylphenyl)-2-propynyl]oxy}ethyl)-1H-imidazo[4,5-c]quinolin-4-amine

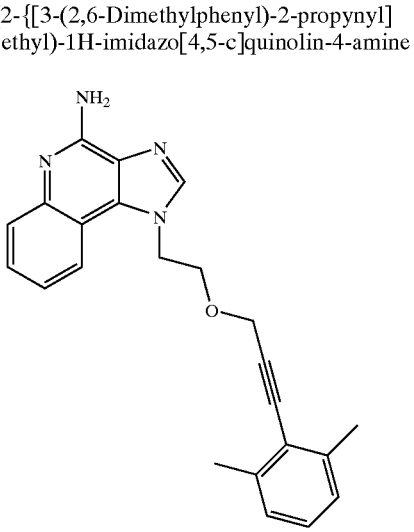

Using the general method of Example 7, 1-[2-(2-propynyloxy)ethyl]-1H-imidazo[4,5-c]quinolin-4-amine (0.50 g, 1.88 mmol) was reacted with 2,6-dimethyl iodobenzene (0.61 g, 2.63 mmol). The crude product was purified by column chromatography eluting with 95/5 dichloromethane/methanol to provide 0.056 g of 1-(2-{[3-(2,6-dimethylphenyl)-2-propynyl]oxy}ethyl)-1H-imidazo[4,5-c]quinolin-4-amine as a solid, m.p. 200–201° C.

Analysis. Calculated for $C_{23}H_{22}N_4O \cdot (H_2O)_{2/5}$: % C, 73.29; % H, 6.07; % N, 4.86. Found: % C, 73.36; % H, 5.88; % N, 14.84.

¹H NMR (300 MHz, DMSO-d6) δ 8.19 (s, 1H), 8.13 (d, J=8.1 Hz, 1H), 7.62 (d, J=7.9 Hz, 1H), 7.44 (t, J=8.0 Hz, 1H), 7.23 (t, J=7.9 Hz, 1H), 7.09–7.14 (m, 1H), 7.01–7.03 (m, 2H), 6.76 (s, 2H), 4.87 (t, J=4.9 Hz, 2H), 4.48 (s, 2H), 4.05 (t, J=4.9 Hz, 2H), 2.15 (s, 6H),

IR (KBr) 3379, 3065, 1659, 1530, 1483, 1107, 751 cm⁻¹

HRMS (EI) Calculated for $C_{23}H_{22}N_4O$ (M⁺) 370.1794, found 370.1789.

Example 9

1-(2-{[3-(4-Phenoxyphenyl)-2-propynyl]oxy}ethyl)-1H-imidazo[4,5-c]quinolin-4-amine

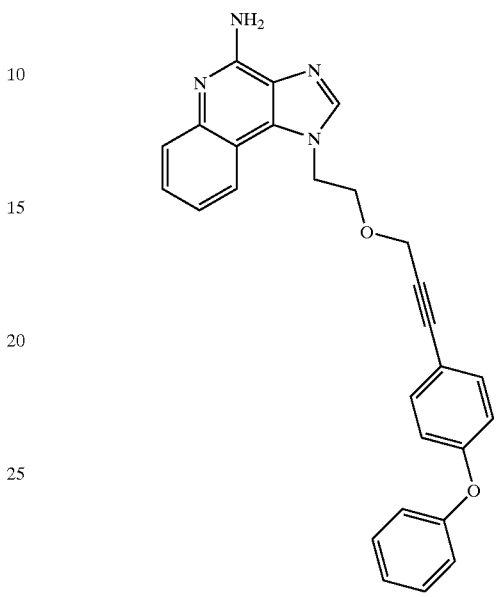

Using the general method of Example 7, 1-[2-(2-propynyloxy)ethyl]-1H-imidazo[4,5-c]quinolin-4-amine (0.50 g, 1.88 mmol) was reacted with 4-iodophenyl phenyl ether (0.78 g, 2.63 mmol). The crude product was purified by column chromatography eluting with 95/5 dichloromethane/methanol to provide a solid. The solid was slurried with aqueous sodium hydroxide to remove salts and then purified by column chromatography eluting with 9/1 ethyl acetate/methanol to provide a solid. This material was further purified by column chromatography eluting with 99/1 ethyl acetate/methanol to provide 24 mg of 1-(2-{[3-(4-phenoxyphenyl)-2-propynyl]oxy}ethyl)-1H-imidazo[4,5-c]quinolin-4-amine as a solid, m.p. 146–148° C.

Analysis. Calculated for $C_{27}H_{22}N_4O_2 \cdot (H_2O)_{4/5}$: % C, 72.24; % H, 5.30; % N, 12.48. % C, 71.82; % H, 4.85; % N, 12.35.

¹H NMR (300 MHz, DMSO-d6) δ 8.18 (s, 1H), 8.12 (d, J=7.4 Hz, 1H), 7.62 (d, J=7.7 Hz, 1H), 7.41–7.47 (m, 3H), 7.18–7.27 (m, 4H), 7.06 (dd, J=7.6, 1.0 Hz, 2H), 6.90 (dd, J=6.7 Hz, 2H), 6.71 (s, 2H), 4.85 (t, J=5.1 Hz, 2H), 4.37 (s, 2H), 4.02 (t, J=5.0 Hz, 2H)

IR (KBr) 3444, 3070, 2928, 1500, 1230, cm⁻¹

HRMS (EI) Calculated for $C_{27}H_{22}N_4O_2$ (M⁺) 434.1743, found 434.1748.

Example 10

1-[2-({3-[2-(Trifluoromethyl)phenyl]-2-propynyl}oxy)ethyl]-1H-imidazo[4,5-c]quinolin-4-amine

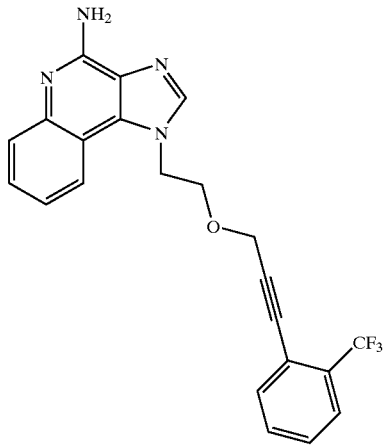

Using the general method of Example 7, 1-[2-(2-propynyloxy)ethyl]-1H-imidazo[4,5-c]quinolin-4-amine (0.50 g, 1.88 mmol) was reacted with 2-iodobenzotrifluoride (0.71 g, 2.63 mmol). The reaction mixture was concentrated under reduced pressure. The resulting glassy solid was treated with aqueous sodium bisulfite (10 mL) and methanol (20 mL). A solid was removed by filtration. The filtrate was concentrated under reduced pressure to provide a white powder. This material was washed with water and dried for 4 days in an oven at 80° C. to provide ~0.33 g of a solid. This material was partially dissolved in a mixture of dichloromethane (17 mL) and methanol (17 mL). Hydrogen chloride/diethyl ether (3.24 mL of 1.0 M) was added and the mixture turned homogeneous. The mixture was concentrated under reduced pressure to provide a brown crystalline residue. The residue was combined with 50/50 acetonitrile/ethyl acetate containing a small amount of methanol. Sodium hydroxide (0.5 mL of 20%) was added. The mixture was concentrated under reduced pressure to provide a glassy solid. This glassy solid was purified by column chromatography eluting with 9/1 ethyl acetate/methanol to provide 14 mg of 1-[2-({3-[2-(trifluoromethyl)phenyl]-2-propynyl}oxy)ethyl]-1H-imidazo[4,5-c]quinolin-4-amine as a white crystalline solid, m.p. 154–155° C.

Analysis. Calculated for $C_{22}H_{17}F_3N_4O$: % C, 64.39; % H, 4.18; % N, 13.65. Found: % C, 64.39; % H, 4.19; % N, 13.71

$^1$H NMR (300 MHz, DMSO-d6) δ 8.16 (s, 1H), 8.11 (d, J=7.4 Hz, 1H), 7.74 (d, J=7.3 Hz, 1H), 7.56–7.64 (m, 3H), 7.38–7.46 (m, 2H), 7.22 (t, J=7.6 Hz, 1H), 6.59 (s, 2H), 4.87 (t, J=5.1 Hz, 2H), 4.45 (s, 2H), 4.04 (t, J=5.1 Hz, 2H)

IR (KBr) 3375, 3102, 1657, 1583, 1530, 1484, 1320, 1103, 765 cm$^{-1}$

HRMS (EI) Calculated for $C_{22}H_{17}F_3N_4O$ (M$^+$) 410.1354, found 410.1350.

Example 11

1-(2-{3-[4-(1H-1-Pyrrolyl)phenyl]propoxy}ethyl)-1H-imidazo[4,5-c]quinolin-4-amine trifluoroacetate

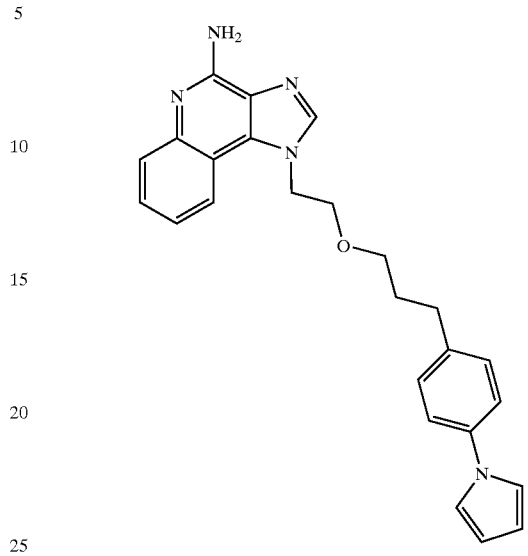

Part A

Under a nitrogen atmosphere dibenzyl dicarbonate (50 g, 174 mmol) was added to a mixture of 1-[2-(2-propynyloxy) ethyl]-1H-imidazo[4,5-c]quinolin-4-amine (16.4 g, 61.6 mmol) and anhydrous N,N-dimethylformamide (200 mL). The reaction mixture was allowed to stir at ambient temperature for 16 hours and the reaction mixture turned homogeneous. The reaction mixture was partitioned between ethyl acetate and water. The layers were separated. The aqueous layer was extracted with ethyl acetate. The organic fractions were combined, washed with water, washed with brine, dried over magnesium sulfate, filtered and then concentrated under reduced pressure to provide a semisolid. This material was triturated with diethyl ether to provide 27.4 g of N,N-(bis benzyloxycarbonyl)-1-[2-(2-propynyloxy)ethyl]-1H-imidazo[4,5-c]quinolin-4-amine as a white solid.

Part B

Under a nitrogen atmosphere N,N-(bis benzyloxycarbonyl)-1-[2-(2-propynyloxy)ethyl]-1H-imidazo[4,5-c]quinolin-4-amine (0.5 g, 0.94 mmol), anhydrous acetonitrile (5 mL), triethylamine (0.34 mL, 2.43 mmol), and 1-(4-iodophenyl)pyrrole (0.28 g, 1.03 mmol) were combined and the resulting homogeneous mixture was heated to 80° C. Copper (I) iodide (0.007 g) and dichlorobis (triphenylphosphine)palladium(II) (0.013 g) were added. The reaction was complete in 30 minutes. The product was purified by liquid chromatography using 4/6 hexane/ethyl acetate to provide a glassy solid. This material was purified on a second column using 9/1 hexane/ethyl acetate to provide 0.229 g of N,N-(bis benzyloxycarbonyl)-1-[2-({3-[4-(1H-pyrrol-1-yl)phenyl]prop-2-ynyl}oxy)ethyl]-1H-imidazo[4,5-c]quinolin-4-amine.

$^1$H NMR (500 MHz, DMSO-d6) δ 8.49 (d, J=7.7 Hz, 1H), 8.44 (s, 1H), 8.14 (d, J=7.9 Hz, 1H), 7.75–7.77 (m, 2H), 7.54 (d, J=5.1 Hz, 2H), 7.40 (s, 2H), 7.32 (d, J=6.8 Hz, 2H), 7.24–7.27 (m, 6H), 7.14–7.16 (m, 4H), 6.29 (s, 2H), 5.18 (s, 4H), 5.00 (t, J=5.2 Hz, 2H), 4.42 (s, 2H), 4.10 (t, J=5.1 Hz, 2H)

MS (CI) for $C_{41}H_{33}N_5O_5$ m/z 676 (MH$^+$), 632, 524, 408

Part C

The material from Part B, palladium hydroxide (0.24 g of 20% on carbon) and methanol (5 mL) were combined in a Parr flask and hydrogenated at 45 psi (3.2 Kg/cm$^2$) for 3–4 hours. The reaction mixture was filtered to remove catalyst, the filter cake was washed with additional methanol, and the filtrate was concentrated under reduced pressure. The residue was purified by semi-preparative HPLC using Method B to provide 36.6 mg of 1-(2-{3-[4-(1H-1-pyrrolyl)phenyl]propoxy}ethyl)-1H-imidazo[4,5-c]quinolin-4-amine trifluoroacetate as a solid, m.p. 179–181° C.

Analysis. Calculated for $C_{25}H_{25}N_5O \cdot C_2HF_3O_2$: % C, 61.71; % H, 4.99; % N, 13.33. Found: % C, 61.49; % H, 4.89; % N, 13.23

$^1$H NMR (500 MHz, DMSO-d6) δ 8.51 (s, 1H), 8.38 (d, J=8.4 Hz, 1H), 7.84 (d, J=8.4 Hz, 1H), 7.73 (t, J=7.3 Hz, 1H), 7.56 (t, J=7.8, 1H), 7.33 (d, J=8.4 Hz, 2H), 7.26 (t, J=2.1 Hz, 2H), 6.96 (d, J=8.4, 2H), 6.24 (t, J=2.1H, 2H), 4.91 (t, J=5.0, 2H), 3.85 (t, J=5.0, 2H), 3.3–3.4 (m, 2H), 2.35 (t, J=7.6, 2H), 1.61 (m, 2H),

IR(KBr) 2949, 1705, 1523, 1204, 1123, 721 cm$^{-1}$

HRMS (EI) Calculated for $C_{25}H_{25}N_5O$ (M$^+$) 411.2059, found 411.2060.

Example 12

3-{3-[2-(4-Amino-1H-imidazo[4,5-c]quinolin-1-yl)ethoxy]propyl}benzoic acid bis(trifluoroacetate)

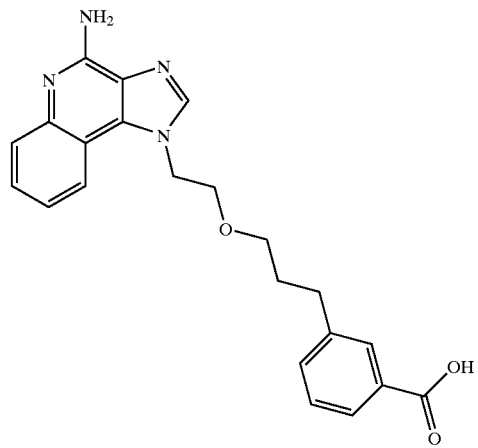

Part A

Under a nitrogen atmosphere N,N-(bis tert-butoxycarbonyl)-1-[2-(2-propynyloxy)ethyl]-1H-imidazo[4,5-c]quinolin-4-amine (2.82 g g, 6.04 mmol), benzyl 3-iodobenzoate (2.245 g, 6.64 mmol), triethylamine (2.2 mL, 15.7 mmol), and anhydrous acetonitrile (20 mL) were combined and the resulting mixture was heated to 60° C. Copper (I) iodide (0.05 g) and dichlorobis(triphenylphosphine)palladium(II) (0.0.08 g) were added. The reaction was complete in 30 minutes. The reaction mixture was concentrated under reduced pressure and the residue was purified by column chromatography eluting initially with dichloromethane and then with 98/2 dichloromethane/methanol to provide 1.82 g of benzyl 3-{3-[2-(4-(bis tert-butoxycarbonyl)amino-1H-imidazo[4,5-c]quinolin-1-yl)ethoxy]prop-1-ynyl}benzoate.

$^1$H NMR (300 MHz, DMSO-d6) δ 8.46 (d, J=9.6 Hz, 1H), 8.39 (s, 1H), 8.05 (d, J=9.8 Hz, 1H), 7.94–7.98 (m, 1H), 7.84 (s, 1H), 7.50–7.70 (m, 2H), 7.36–7.49 (m, 7H), 5.36 (s, 2H), 4.98 (t, J=4.6 Hz, 2H), 4.37 (s, 2H), 4.06–4.13 (m, 2H), 1.30 (s, 18H)

MS (CI) for $C_{39}H_{40}N_4O_7$ m/z 677 (MH$^+$), 577, 477

Part B

A solution of the material from Part A in methanol was combined with catalyst (1.0 g of 10% palladium on carbon) and the mixture was hydrogenated at 45 psi (3.2 Kg/cm$^2$) at ambient temperature for ~2.25 hours. More catalyst (0.3 g) was added and the hydrogenation was continued for an additional 2 hours. The reaction mixture was filtered to remove the catalyst and the filter cake was rinsed thoroughly with methanol. The filtrate was concentrated under reduced pressure to provide 1.2 g of N,N-(bis tert-butoxycarbonyl)-3-{3-[2-(4-amino-1H-imidazo[4,5-c]quinolin-1-yl)ethoxy]propyl}benzoic acid.

$^1$H NMR (300 MHz, DMSO-d6) δ 8.50 (d, J=9.5 Hz, 1H), 8.40 (s, 1H), 8.07–8.10 (m, 1H), 7.70–7.75 (m, 3H), 7.65 (s, 1H), 1.29 (s, 18H), 7.29 (t, J=7.6 Hz, 1H), 7.10 (d, J=7.8 Hz, 1H), 4.94 (t, J=4.5 Hz, 2H), 3.88 (t, J=4.5 Hz, 2H), 3.32 (t, J=6.0 Hz, 2H), 2.43 (t, J=7.0 Hz, 2H), 1.62 (m, 2H)

MS (CI) for $C_{32}H_{38}N_4O_7$ m/z 591 (MH$^+$), 491, 391

Part C

Under a nitrogen atmosphere the material from Part B was combined with anhydrous dichloromethane (10 mL) and trifluoroacetic acid (10 mL). The reaction mixture was stirred for 1.5 hours. The reaction mixture was concentrated under reduced pressure to provide an oil which was dried under high vacuum at ambient temperature to give a solid. This solid was triturated with ether. The resulting white powder was dried at 65° C. in a vacuum oven overnight to provide 1.19 g of 3-{3-[2-(4-amino-1H-imidazo[4,5-c]quinolin-1-1)ethoxy]propyl}benzoic acid bis(trifluoroacetate), m.p. 138–140° C.

Analysis. Calculated for $C_{22}H_{22}N_4O_3 \cdot (C_2HF_3O_2)_2$: % C, 50.49; % H, 3.91; % N. 9.06.

Found: % C, 50.37; % H, 3.67; % N, 9.08

$^1$H NMR (300 MHz, DMSO-d6) δ 9.07–7.14 (bs, 2H), 8.51 (s, 1H), 8.37 (d, J=7.8 Hz, 1H), 7.82 (d J=8.0 Hz, 1H), 7.74 (m, 2H), 7.64 (s, 1H), 7.56 (t, J=7.1 Hz, 1H), 7.30 (t, J=7.7 Hz, 1H), 7.15 (d, J=7.6 Hz, 1H), 4.91 (t, J=4.5 Hz, 2H), 3.86 (t, J=4.4 Hz, 2H), 3.34 (t, J=5.9 Hz, 2H), 2.44 (t, J=7.4 Hz, 2H), 1.64 (m, 2H)

IR (KBr) 3367, 3104, 2372, 1685, 1204, 1146 cm$^{-1}$

HRMS (EI) Calculated for $C_{22}H_{22}N_4O_3$ (M$^+$) 390.1692, found 390.1690.

Example 13

2-{3-[2-(4-Amino-1H-imidazo[4,5-c]quinolin-1-yl)ethoxy]propyl}benzoic acid trifluoroacetate

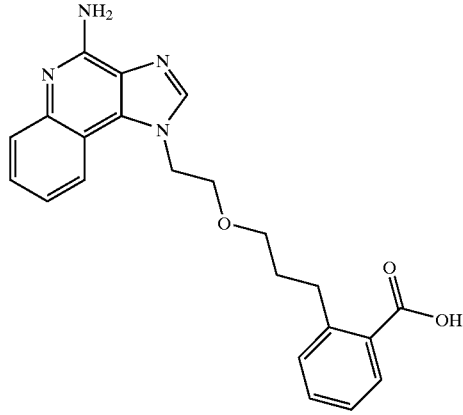

Part A

Using the general method of Example 12 Part A, N,N-(bis tert-butoxycarbonyl)-1-[2-(2-propynyloxy)ethyl]-1H- imidazo[4,5-c]quinolin-4-amine (2 g, 4.3 mmol) was coupled with benzyl 2-iodobenzoate (1.57 g, 4.71 mmol) to provide 1.79 g of a mixture of mono-and di-BOC protected benzyl 2-{3-[2-(4-amino-1H-imidazo[4,5-c]quinolin-1-yl)ethoxy]prop-1-ynyl}benzoate.

$^1$H NMR (300 MHz, DMSO-d6) δ 8.45 (d, J=7.9 Hz, 1H), 8.39 (s, 1H), 8.06–8.09 (m, 1H), 7.85–7.88 (m, 1H), 7.70–7.73 (m, 2H), 7.47–7.51 (m, 2H), 7.40–7.43 (m, 2H), 7.28–7.37 (m, 3H), 7.19 (m, 1H), 5.23 (s, 2H), 4.97 (t, J=5.0 Hz, 2H), 4.27 (s, 2H), 4.07 (t, J=4.9 Hz, 2H), 1.30 (s, 18H)

MS (CI) for $C_{39}H_{40}N_4O_7$ m/z 677 (MH$^+$), 577, 477

Part B

Using the general method of Example 12 Part B, the material from Part A was hydrogenated to provide 0.041 g of a mixture of mono-and di-BOC protected 2-{3-[2-(4-amino-1H-imidazo[4,5-c]quinolin-1-yl)ethoxy]propyl}benzoic acid.

$^1$H NMR (300 MHz, DMSO-d6) δ 8.50 (d, J=7.3 Hz, 1H), 8.39 (s, 1H), 8.08 (d, J=7.9 Hz, 1H), 7.71–7.75 (m, 3H), 7.22–7.28 (m, 2H), 6.90 (d, J=7.4 Hz, 1H), 4.93 (t, J=4.6 Hz, 2H), 3.87 (t, J=4.5 Hz, 2H), 3.30 (t, J=5.6 Hz, 2H), 2.73 (t, J=5.7 Hz, 2H), 1.61 (m, 2H), 1.28 (s, 18H)

MS (CI) for $C_{32}H_{38}N_4O_7$ m/z 591 (MH$^+$), 491, 391

Part C

Using the general method of Example 12 Part C, the material from Part B was hydrolyzed to provide 0.28 g of 2-{3-[2-(4-amino-1H-imidazo[4,5-c]quinolin-1-yl)ethoxy]propyl}benzoic acid as a solid, m.p. 186–188° C.

Analysis. Calculated for $C_{22}H_{22}N_4O_3O_3 \cdot C_2HF_3O_2$: % C, 57.14; % H, 4.59; % N, 11.11. Found: % C, 56.81; % H, 4.47; % N, 11.08

$^1$H NMR (300 MHz, DMSO-d6) δ 8.90–9.20 (bs, 1H), 8.50 (s, 1H), 8.38 (d, J=10.1 Hz, 1H), 7.84 (d, J=8.3 Hz, 1H), 7.71–7.75 (m, 2H), 7.56 (t, J=7.6 Hz, 1H), 7.21–7.32 (m, 2H), 6.88 (d, J=6.9 Hz, 2H), 4.90 (t, J=4.8 Hz, 2H), 3.84 (t, J=4.6 Hz, 2H), 3.32 (m, 2H), 2.72 (t, J=6.9 Hz, 2H), 1.62 (m, 2H)

IR (KBr) 3212, 2929, 1709, 1204, 1124, 747 cm$^{-1}$

HRMS (EI) Calculated for $C_{22}H_{22}N_4O_3$ (M$^+$) 390.1692, found 390.1693.

Example 14

4-{3-[2-(4-Amino-1H-imidazo[4,5-c]quinolin-1-yl)ethoxy]propyl}benzoic acid trifluoroacetate

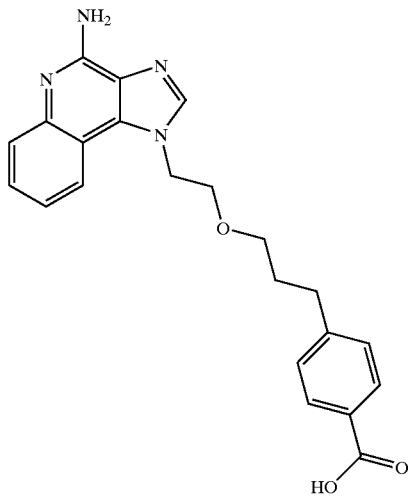

Part A

Using the general method of Example 12 Part A, N,N-(bis tert-butoxycarbonyl)-1-[2-(2-propynyloxy)ethyl]-1H-imidazo[4,5-c]quinolin-4-amine (2.82 g, 6.04 mmol) was coupled with benzyl 4-iodobenzoate (2.25 g, 6.64 mmol) to provide 2.14 g of a mixture of mono- and di-BOC protected benzyl 4-[3-(2-{4-amino-1H-imidazo[4,5-c]quinolin-1-yl}ethoxy)prop-1-ynyl]benzoate.

$^1$H NMR (300 MHz, DMSO-d6) δ 8.47 (d, J=7.2 Hz, 1H), 8.40 (s, 1H), 8.06 (d, J=6.5 Hz, 1H), 7.87–7.89 (m, 2H), 7.70–7.73 (m, 2H), 7.36–7.49 (m, 5H), 7.23–7.27 (m, 2H), 5.35 (s, 2H), 5.0 (t, J=4.5 Hz, 2H), 4.40 (s, 2H), 4.09 (t, J=4.5 Hz, 2H), 1.30 (s, 18H)

MS (CI) for $C_{39}H_{40}N_4O_7$ m/z 677 (MH$^+$), 577, 477

Part B

Using the general method of Example 12 Part B, the material from Part A was hydrogenated to provide 1.86 g of a mixture of mono-and di-BOC protected 4-{3-[2-(4-amino-1H-imidazo[4,5-c]quinolin-1-yl)ethoxy]propyl}benzoic acid.

$^1$H NMR (300 MHz, DMSO-d6) δ 8.51 (d, J=7.1 Hz, 1H), 8.40 (s, 1H), 8.07–8.10 (m, 1H), 7.72–7.75 (m, 4H), 7.01 (d, J=8.4 Hz, 2H), 4.94 (t, J=4.7 Hz, 2H), 3.88 (t, J=4.6 Hz, 2H), 3.30 (m, 2H), 2.38 (t, J=7.3 Hz, 2H), 1.62 (m, 2H), 1.29 (s, 18H)

MS (CI) for $C_{32}H_{38}N_4O_7$ m/z 591 (MH$^+$), 491, 391

Part C

Using the general method of Example 12 Part C, the material from Part B was hydrolyzed to provide 0.96 g of 4-{3-[2-(4-amino-1H-imidazo[4,5-c]quinolin-1-yl)ethoxy]propyl}benzoic acid trifluoroacetate, m.p. 235–237° C.

Analysis Calculated for $C_{22}H_{22}N_4O_3 \cdot C_2HF_3O_2$: % C, 57.14; % H, 4.59; % N, 11.11. Found: % C, 57.06; % H, 4.47; % N, 11.03

$^1$H NMR (300 MHz, DMSO-d6) δ 9.00–9.11 (bs, 2H), 8.51 (s, 1H), 8.37 (d, J=8.4 Hz, 1H), 7.83 (d, J=6.0 Hz, 1H), 7.71–7.76 (m, 3H), 7.55 (t J=9.7 Hz, 1H), 7.01 (d, J=8.2 Hz, 2H), 4.91 (t, J=5.0 Hz, 2H), 3.84 (t, J=4.7 Hz, 2H), 3.32 (t, J=5.8 Hz, 2H), 2.38 (t, J=7.1 Hz, 2H), 1.62 (m, 2H)

IR (KBr) 3266, 3014, 2361, 1667, 1277, 1201, 1142 cm$^{-1}$

HRMS (EI) Calculated for $C_{22}H_{22}N_4O_3$ (M$^+$) 390.1692, found 390.1697.

Example 15

1-(2-{3-[3-(Dimethylamino)phenyl]propoxy}ethyl)-1H-imidazo[4,5-c]quinolin-4-amine dihydrochloride

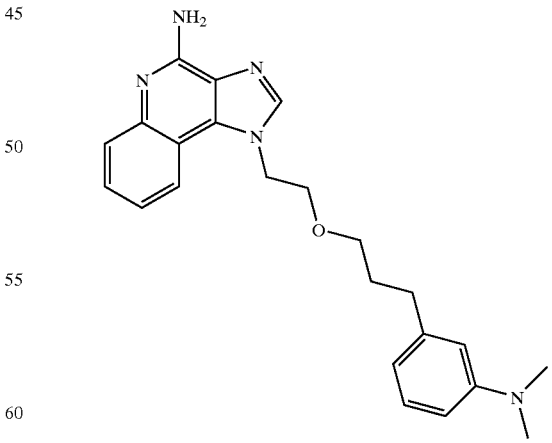

Part A

Using the general method of Example 12 Part A, except that the reaction temperature was raised to 80° C., N,N-(bis tert-butoxycarbonyl)-1-[2-(2-propynyloxy)ethyl]-1H-imidazo[4,5-c]quinolin-4-amine (3 g, 6.43 mmol) was coupled with 3-iodo-N,N-dimethylaniline (7.07 mmol) to provide 3.06 g of a mixture of mono protected and unprotected 1-[2-({3-[3-(dimethylamino)phenyl]prop-2-ynyl}oxy)ethyl]-1H-imidazo[4,5-c]quinolin-4-amine.

Part B

Using the general method of Example 12 Part B, the material from Part A was hydrogenated to provide ~2.9 g of a mixture of mono Boc protected and unprotected 1-(2-{3-[3-(dimethylamino)phenyl]propoxy}ethyl)-1H-imidazo[4,5-c]quinolin-4-amine.

Part C

The material from Part B was combined with hydrogen chloride/methanol (30 mL of 3 M) and stirred at ambient temperature for 19 hours. A precipitate was removed by filtration. The filtrate was concentrated under reduced pressure and the residue was dissolved in a small amount of methanol and then neutralized with concentrated ammonium hydroxide to pH ~11. The resulting precipitate was purified by column chromatography eluting with 95/5/1 dichloromethane/methanol/ammonium hydroxide. This material was combined with hydrogen chloride/diethyl ether. The resulting solution was concentrated under reduced pressure. The residue was triturated with diethyl ether. The resulting solid was isolated by filtration and then dried to provide 0.114 g of 1-(2-{3-[3-(dimethylamino)phenyl] propoxy}ethyl)-1H-imidazo[4,5-c]quinolin-4-amine dihydrochloride, m.p. 180–183° C.

Analysis. Calculated for $C_{23}H_{27}N_5O \cdot (HCl)_{2.1} \cdot (H_2O)_{2.1}$: % C, 54.82; % H, 6.66; % N, 13.89. Found: % C, 54.60; % H, 6.50; % N, 13.66

$^1$H NMR (300 MHz, DMSO-d6) δ 8.71–8.73 (bs, 2H), 8.44 (s, 1H), 8.35 (d, J=7.4 Hz, 1H), 7.83 (d, J=8.0 Hz, 1H), 7.72 (t, J=7.6 Hz, 1H), 7.55 (t, J=6.8 Hz, 1H), 7.15 (m, 1H), 7.05 (m, 1H), 6.96 (s, 1H), 6.66 (d, J=8.1 Hz, 1H), 4.88 (t, J=5.3 Hz, 2H), 4.02 (t, J=3.7 Hz, 2H), 3.37 (t, J=6.4 Hz, 2H), 2.94 (s, 6H), 2.40 (t, J=7.6 Hz, 2H), 1.66 (m, 2H),

IR (KBr) 3426, 3138, 2928, 1693, 1113 cm$^{-1}$

HRMS (E1) Calculated for $C_{23}H_{27}N_5O$ (M$^+$) 389.2216, found 389.2217

Example 16

2-(Ethoxymethyl)-1-[2-(3-phenylpropoxy)ethyl]-1H-imidazo[4,5-c]quinolin-4-amine Hydrochloride

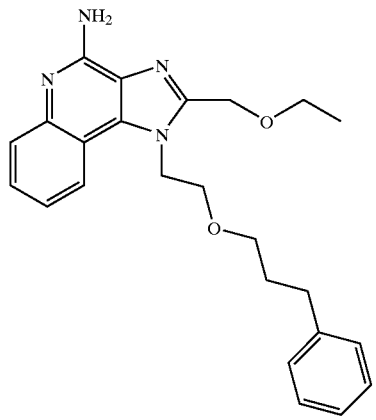

Part A

2-[2-(Ethoxymethyl)-1H-imidazo[4,5-c]quinolin-1-yl] ethanol (3.50 g, 12.9 mmol) was slowly added over a period of 20 minutes to a suspension of sodium hydride (0.67 g of 60% in mineral oil, 16.77 mmol) in anhydrous N,N-dimethylformamide. The reaction mixture was allowed to stir for 1 hour and then 1-bromo-3-phenylpropane (2.16 mL, 14.19 mmol) was added. The reaction mixture was stirred overnight. The reaction mixture was diluted with ethyl acetate, washed with water, washed with brine, dried over magnesium sulfate, filtered and then concentrated under reduced pressure. The residue was purified by column chromatography eluting with ethyl acetate to provide 2.38 g of 2-(ethoxymethyl)-1-[2-(3-phenylpropxy)ethyl]-1H-imidazo[4,5-c]quinoline as a yellow oil.

MS (CI) for $C_{24}H_{27}N_3O_2$ m/z 390 (MH+), 346.

Part B

The material from Part A was combined with chloroform (50 mL) and cooled to 0° C. 3-chloroperoxybenzoic acid (2.22 g of 57–86%) was added. After 1 hour the reaction mixture was allowed to warm to ambient temperature. The reaction mixture was partitioned between aqueous sodium bicarbonate and dichloromethane. The organic fraction was dried over magnesium sulfate, filtered and then concentrated under reduced pressure to provide 2-(ethoxymethyl)-1-[2-(3-phenylpropxy)ethyl]-1H-imidazo[4,5-c]quinoline-5N-oxide as a brown solid.

Part C

Under a nitrogen atmosphere trichloroacetyl isocyanate (0.87 mL, 7.33 mmol) was slowly added to a mixture of the material from Part B and anhydrous dichloromethane (60 mL). After 1 hour the reaction mixture was concentrated under reduced pressure to provide 2,2,2-trichloro-N-{2-(ethoxymethyl)-1-[2-(3-phenylpropxy)ethyl]-1H-imidazo[4,5-c]quinolin-1-yl}acetamide.

Part D

Sodium methoxide (4.79 mL of 25% in methanol) was added to a mixture of the material from Part C and methanol (30 mL). The reaction mixture was allowed to stir overnight and then it was concentrated under reduced pressure to provide a dark oil. The dark oil was purified by column chromatography eluting with 5% methanol in dichloromethane to provide a light yellow oil. The oil was treated with 1.0 M hydrogen chloride to provide a white solid. The material was isolated by filtration and then dried overnight in a vacuum oven at 80° C. to provide 0.79 g of 2-(ethoxymethyl)-1-[2-(3-phenylpropoxy)ethyl]-1H-imidazo[4,5-c]quinolin-4-amine hydrochloride as a white solid, m.p. 128–134° C. Analyzed for $C_{24}H_{28}N_4O_2 \cdot 1.55$ HCl: % C, 62.53; % H, 6.46; % N, 12.15; Found: % C, 62.64; % H, 6.47; % N, 11.91.

$^1$H-NMR (300 MHz, DMSO-d6) δ 8.14 (br d, J=8.3 Hz, 1H), 7.63 (dd, J=8.3, 1.0 Hz, 1H), 7.45 (m, 1H), 7.24 (m, 1H), 7.05–7.15 (m, 3H), 6.90 (m, 2H), 6.62 (s, 2H), 4.80–4.90 (m, 4H), 3.83 (t, J=5.4 Hz, 2H), 3.56 (q, J=7.0 Hz, 2H), 3.27 (t, J=6.1 Hz, 2H), 2.37 (t, J=7.6 Hz, 2H), 1.63 (m, 2H), 1.16 (t, J=6.8 Hz, 3H)

IR (KBr) 3267, 3023, 1681, 1108 cm$^{-1}$

HRMS (EI) Calculated for $C_{24}H_{28}N_4O_2$ (M$^+$) 404.2212, found 404.2215.

Example 17

1-(1-{[(3-Chlorobenzyl)oxy]methyl}propyl)-1H-imidazo[4,5-c]quinolin-4-amine

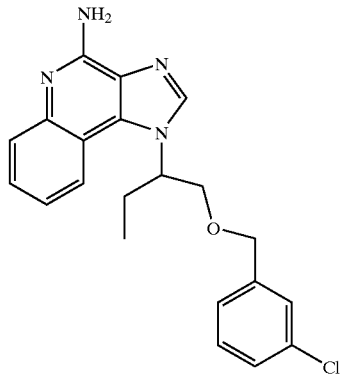

Part A

2-Ethyl-2-(1H-imidazo[4,5-c]quinolin-1-yl)-1-ethanol (3.0 g, 12.43 mmol), dichloromethane (40 mL), aqueous sodium hydroxide (40 mL of 50%), benzyltrimethylammonium chloride (0.01 g) and 3-chlorobenzyl bromide (2.81 g, 13.67 mmol) were combined and the resulting solution was stirred at ambient temperature overnight. Analysis by TLC (5% methanol in dichloromethane) indicated that the reaction was complete. The reaction was diluted with dichloromethane (100 mL) and water (100 mL). The layers were separated. The aqueous fraction was extracted with dichloromethane. The organic fractions were combined, washed with brine, dried over magnesium sulfate and then concentrated under reduced pressure. The residue was purified by flash chromatography (silica gel eluting with ethyl acetate) to provide 4.22 g of 1-(1-{[(3-chlorobenzyl)oxy]methyl}propyl)-1H-imidazo[4,5-c]quinoline as a light orange oil.

$^1$H-NMR (300 MHz, DMSO-d6) δ 9.22 (s, 1H), 8.63 (s, 1H), 8.55 (d, J=7.8 Hz, 1H), 8.17 (dd, J=7.8, 1.5 Hz, 1H), 7.69 (m, 2H), 7.23 (dd, J=4.9, 1.5 Hz, 2H), 7.08 (s, 1H), 7.03 (m, 1H), 5.40 (m, 1H), 4.47 (s, 2H), 3.34–4.07 (m, 2H), 2.11 (m, 2H), 0.88 (t, 7.3 Hz, 3H)

MS (CI) for $C_{21}H_{20}ClN_3O$ m/z 366 (MH$^+$), 332

Part B

3-Chloroperoxy benzoic acid (2.84 g of 77%) was added in portions to a solution of the material from Part A in chloroform (60 mL). After 2 hours analysis by TLC (10% methanol in dichloromethane) indicated that the reaction was complete. The reaction was diluted with chloroform, washed with saturated sodium bicarbonate, washed with brine, dried over magnesium sulfate and then concentrated under reduced pressure to provide crude 1-(1-{[(3-chlorobenzyl)oxy]methyl}propyl)-1H-imidazo[4,5-c]quinolin-5N-oxide.

Part C

Ammonium hydroxide (20 mL) was added to a solution of the material from Part B in dichloromethane (80 mL). Tosyl chloride (2.42 g) was added in portions. Analysis by TLC (5% methanol in dichloromethane) indicated that the reaction went to completion immediately after the addition of the tosyl chloride. The reaction mixture was diluted with dichloromethane and saturated sodium bicarbonate. The layers were separated. The organic layer was washed with brine, dried over magnesium sulfate and then concentrated under reduced pressure to provide a light brown oil. The oil was purified by flash chromatography (silica gel eluting with 5% methanol in dichloromethane) to provide an off-white gooey solid. This material was purified by flash chromatography (silica gel eluting with 5% methanol in dichloromethane) to provide a pinkish-white solid. This material was further purified by flash chromatography (silica gel eluting with ethyl acetate) to provide ~1.0 g of 1-(1-{[(3-chlorobenzyl)oxy]methyl}propyl)-1H-imidazo[4,5-c]quinolin-4-amine as an off-white solid, m.p. 60–62° C. Analysis: Calculated for $C_{21}H_{21}ClN_4O·¼H_2O$: % C, 65.41: % H, 5.62; % N, 14.54; Found: % C, 65.5; % H, 5.62; % N, 14.61.

$^1$H-NMR (300 MHz, DMSO-d6) δ 8.37 (s, 1H), 8.19 (d, J=8.3 Hz, 1H), 7.62 (dd, J=8.3, 1.5 Hz, 1H), 7.43 (dt, J=8.3, 1.5 Hz, 1H), 7.18–7.28 (m, 3H), 7.09 (m, 1H), 6.52 (br s, 2H), 5.24 (m, 1H), 4.48 (s, 2H), 4.01 (dd, J=10.5, 6.6 Hz, 2H), 3.92 (dd, J=10.3, 4.4 Hz, 2H), 2.10 (quintet, J=7.3 Hz, 2H), 0.88 (t, 7.3 Hz, 3H)

MS (CI) for $C_{21}H_{21}ClN_4O$ m/z 381 (MH$^+$), 185

Example 18

1-{2-[3-(2-Aminophenyl)propoxy]ethyl}-1H-imidazo[4,5-c]quinolin-4-amine trifluoroacetate

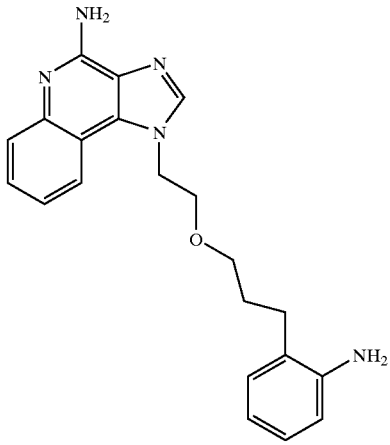

Part A

Under a nitrogen atmosphere, N,N-(bis tert-butoxycarbonyl)-1-[2-(2-propynyloxy)ethyl]-1H-imidazo[4,5-c]quinolin-4-amine (0.50 g, 1.07 mmol), triethylamine (0.39 mL, 2.79 mmol)) and anhydrous acetonitrile (10 mL) were combined. The resulting solution was heated to 80° C. As the reaction was heating, 2-iodoaniline (0.26 mL, 1.18 mmol), copper (I) iodide (0.012 g) and dichlorobis(triphenylphosphine)palladium(II) (0.023 g) were added. The reaction mixture was heated at 80° C. overnight. The acetonitrile was removed under reduced pressure and the residue was purified by flash chromatography (silica gel eluting with 3% methanol in dichloromethane) to provide 0.47 g of N,N-(bis tert-butoxycarbonyl)-1-(2-{[3-(2-aminophenyl)prop-2-ynyl]oxy}ethyl)-1H-imidazo[4,5-c]quinolin-4-amine as a brown solid.

$^1$H-NMR (300 MHz, DMSO-d6, $D_2O$) δ 8.47 (d, J=3.6 Hz, 1H), 8.37 (s, 1H), 8.10 (d, J=9.6 Hz, 1H), 7.75 (m, 2H), 7.04 (t, J=7.2 Hz, 1H), 6.80 (m, 1H), 6.65 (d, J=8.3 Hz, 1H), 6.45 (t, J=7.3 Hz, 1H), 4.98 (t, J=4.4 Hz, 2H), 4.36 (s, 2H), 4.08 (t, J=4.9 Hz, 2H), 1.31 (s, 18H)

Part B

Catalyst (5% platinum on carbon) was added to a solution of N,N-(bis tert-butoxycarbonyl)-1-(2-{[3-(2-aminophenyl)prop-2-ynyl]oxy}ethyl)-1H-imidazo[4,5-c]quinolin-4-amine in methanol. The mixture was hydrogenated on a Parr apparatus at 50 psi (3.5 Kg.cm$^2$) overnight. The reaction mixture was filtered through a layer of Celite® filter aid and the filter cake was washed with additional methanol. The filtrate was concentrated under reduced pressure to provide an off-white solid. This material was purified by flash chromatography (silica gel eluting with dichloromethane, then with 1% methanol in dichloromethane, then with 2% methanol in dichloromethane and finally with 0.3% methanol in dichloromethane) to provide ~0.25 g of N,N-(bis tert-butoxycarbonyl)-1-{2-[3-(2-aminophenyl)propoxy]ethyl}-1H-imidazo[4,5-c]quinolin-4-amine as a light yellow oil.

$^1$H-NMR (300 MHz, DMSO-d6) δ 8.23 (dd, J=8.4, 0.9 Hz, 1H), 8.16 (dd, J=8.4, 0.9 Hz, 1H), 7.97 (s, 1H), 6.96 (dt, J=7.5, 1.6 Hz, 2H), 6.87 (dd, J=7.5, 1.4 Hz, 1H), 6.62 (dt, J=7.3, 1.0 Hz, 1H), 6.57 (dd, J=8.3, 1.1 Hz, 1H), 5.29 (s, 1H), 4.71 (t, J=5.3 Hz, 2H), 3.91 (t, J=5.1 hZ, 2H), 3.38 (t, J=6.0 Hz, 2H), 2.39 (t, J=7.4 Hz, 2H), 1.76 (m, 2H), 1.41 (br s, 18H)

MS (CI) for C$_{31}$H$_{39}$N$_5$O$_5$ m/z 562 (MH$^+$), 462, 362, 229

Part C

A solution of the material from Part B in anhydrous dichloromethane (4 mL) was added with stirring to a solution of trifluoroacetic acid (2 mL) and anhydrous dichloromethane (2 mL) which had been cooled to 0° C. The reaction mixture was kept in an ice bath for about 2 hours and then it was allowed to warm to ambient temperature. The reaction mixture was stirred at ambient temperature overnight. The volatiles were removed under reduced pressure to provide a pink oil. The oil was dissolved in ethyl acetate (~3 mL) and triethylamine (~1 mL) was added dropwise. The mixture was allowed to stir for about an hour. The resulting precipitate was isolated by filtration to provide 0.13 g of 1-{2-[3-(2-aminophenyl)propoxy]ethyl}-1H-imidazo[4,5-c]quinolin-4-amine trifluoroacetate as a white solid. Analysis: Calculated for C$_{21}$H$_{23}$N$_5$O.C$_2$HF$_3$O$_2$: % C, 58.10; % H, 5.09; % N, 14.73; Found: % C, 57.78; % H, 4.97; % N, 14.59.

$^1$H-NMR (300 MHz, DMSO-d6) δ 8.87 (br s, 1H), 8.49 (s, 1H), 8.36 (d, J=7.8 Hz, 1H), 7.83 (d, J=8.3 Hz, 1H), 7.72 (t, J=7.3 Hz, 1H), 7.56 (t, J=7.6 Hz, 1H), 6.81 (t, J=7.6 Hz, 1H), 6.51 (m, 2H), 6.32 (t, J=6.8 Hz, 1H), 4.90 (t, J=4.6 Hz, 2H), 3.85 (t, J=4.9 Hz, 2H), 3.33 (t, J=6.1 Hz, 2H), 2.22 (t, J=7.3 Hz, 2H), 1.55 (m, 2H)

IR (KBr) 3414, 3335, 3253, 3019, 1738, 1202, 1185, 1131 cm$^{-1}$

HRMS (EI) Calculated for C$_{21}$H$_{23}$N$_5$O (M$^+$) 361.1903, found 361.1903

Example 19

4-{[2-(4-Amino-1H-imidazo[4,5-c]quinolin-1-yl)ethoxy]methyl}benzonitrile

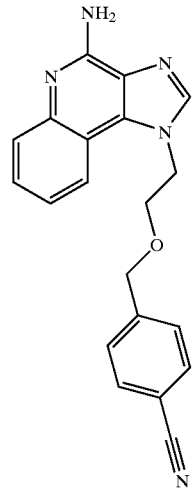

Part A 2-(1H-Imidazo[4,5-c]quinolin-1-yl)ethanol (1.5 g, 7.0 mmol) was added to a stirring mixture of α-bromo-p-tolunitrile (1.79 g, 9.1 mmol), sodium hydroxide (20 ml, 50%), dichloromethane (20 ml), and benzyltrimethylammonium chloride (0.06 g, 0.3 mmol). The reaction was maintained for 18 hours and then diluted with dichloromethane (20 ml) and water (20 ml). The two phases were separated and the aqueous fraction was extracted with additional dichloromethane. The organic fractions were combined, washed with water, dried (MgSO$_4$), filtered, and concentrated. The residue was purified by flash column chromatography (silica gel, 9/1 dichloromethane/methanol) to provide 1.8 g of 4-{[2-(1H-imidazo[4,5-c]quinolin-1-yl)ethoxy]methyl}benzonitrile.

$^1$H NMR (500 MHz, DMSO-d6) δ 9.22 (s, 1H), 8.41 (s, 1H), 8.40 (d, J=1.1 Hz, 1H), 8.17 (dd, J=8.3, 1.2 Hz, 1H), 7.72 (dt, J=7.6, 1.3 Hz, 1H), 7.66 (dt, J=7.6, 1.3 Hz, 1H), 7.63 (d, J=8.3 Hz, 2H), 7.25 (d, J=8.2 Hz, 2H), 4.97 (t, J=5.1 Hz, 2H), 4.53 (s, 2H), 3.97 (t, J=5.5 Hz, 2H);

MS (CI) m/e 329 (M+H).

Part B

3-Chloroperoxybenzoic acid (1.6 g, 5.5 mmol, 60% by weight) was slowly added to a solution of 4-{2-(1H-imidazo[4,5-c]quinolin-1-yl)ethoxy]methyl}benzonitrile (1.8 g, 5.5 mmol) in chloroform (50 ml). The reaction was maintained overnight and then sequentially washed with saturated sodium bicarbonate (200 ml), water (2×100 ml), dried (MgSO$_4$), filtered, and concentrated to provide 1.4 g of 1-{2-[(4-cyanobenzyl)oxy]ethyl}-1H-imidazo[4,5-c]quinoline-5N-oxide.

Part C

Trichloroacetyl isocyanate (0.73 ml, 6.1 mmol) was added dropwise to a solution of 1-{2-[(4-cyanobenzyl)oxy]ethyl}-1H-imidazo[4,5-c]quinoline-5N-oxide (1.4 g, 4.1 mmol) and dichloromethane (25 ml). The reaction was maintained overnight and then concentrated. The resulting red solid was dissolved in methanol (100 ml) and sodium methoxide (4 ml, 25% in methanol) was added dropwise. The reaction was maintained overnight. The crude product formed as a precipitate and was isolated by filtration. Purification of the solid by recrystallization (isopropyl alcohol) followed by flash column chromatography (silica gel, 9/1 dichloromethane/methanol) provided 1.0 g of 4-{[2-(4-amino-1H-imidazo[4,5-c]quinolin-1-yl)ethoxy]methyl}benzonitrile as a white solid, m.p. 238.1–239.2° C.

¹H NMR (300 MHz, DMSO-d6) δ 8.19 (s, 1H), 8.07 (dd, J=8.2, 1.0 Hz, 1H), 7.67 (d, J=8.4 Hz, 2H), 7.62 (dd, J=8.4, 1.1 Hz, 1H), 7.43 (dt, J=7.6, 1.3 Hz, 1H), 7.30 (d, J=8.4 Hz, 2H), 7.21 (dt, J=7.6, 1.3 Hz, 1H), 6.56 (s, 2H), 4.86 (t, J=5.1 Hz, 2H), 4.55 (s, 2H), 3.93 (t, J=5.1 Hz, 2H);

IR (KBr) 3456, 3285, 3117, 3069, 2228, 1637, 1583, 1526, 1481, 1397, 1372, 1353, 1252, 1097, 884, 822, 760 cm⁻¹;

MS (EI) m/e 343.1440 (343.1433 Calculated for $C_{20}H_{17}N_5O$);

Analysis: Calculated for $C_{20}H_{17}N_5O$: % C, 69.96; % H, 4.99; % N, 20.39. Found: % C, 70.09; % H, 4.90; % N, 20.16.

Example 20

2-(Ethoxymethyl)-1-(2-{[6-(4-phenylbutoxy)hexyl]oxy}ethyl)-1H-imidazo[4,5-c]quinoline-4-amine

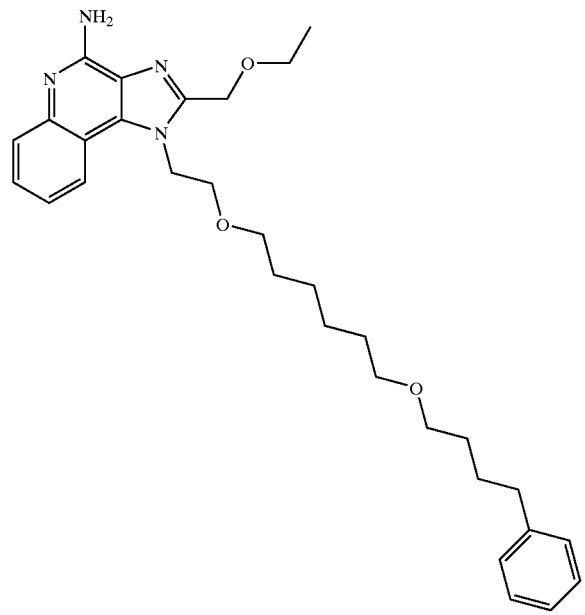

Part A

A solution of 2-[2-(ethoxymethyl)-1H-imidazo[4,5-c]quinolin-1-yl]ethanol (1.0 g, 3.7 mmol) in N,N-dimethylformamide (20 ml) was added dropwise to a suspension of sodium hydride (0.19 g of a 60% dispersion in mineral oil, 4.8 mmol) in N,N-dimethylformamide (10 ml). The reaction was maintained for 45 minutes followed by the dropwise addition of {4-[(6-bromohexyl)oxy]butyl}benzene (1.6 g, 5.1 mmol). The reaction was stirred overnight at room temperature and then partitioned between ethyl acetate and water. The two phases were separated and the aqueous fraction was extracted with additional ethyl acetate. The organic fractions were combined, washed with water, dried (MgSO₄), filtered, and concentrated. The crude product was purified by flash column chromatography (silica gel, 4:1 ethyl acetate/hexanes) to provide 0.81 g of 2-(ethoxymethyl)-1-(2-{[6-(4-phenylbutoxy)hexyl]oxy}ethyl)-1H-imidazo[4,5-c]quinoline as a brown oil.

Part B

3-Chloroperoxybenzoic acid (0.47 g, 1.6 mmol, 60% by weight) was slowly added to a solution of 2-(ethoxymethyl)-1-(2-{[6-(4-phenylbutoxy)hexyl]oxy}ethyl)-1H-imidazo[4,5-c]quinoline (0.81 g, 1.6 mmol) in chloroform (15 ml). The reaction was maintained overnight and then sequentially washed with saturated sodium bicarbonate and water, dried (MgSO₄), filtered, and concentrated to provide 0.7 g of 2-(ethoxymethyl)-1-(2-{[6-(4-phenylbutoxy)hexyl]oxy}ethyl)-1H-imidazo[4,5-c]quinolin-5N-oxide as an orange solid.

Part C

Trichloroacetyl isocyanate (0.25 ml, 2.1 mmol) was added dropwise to a solution of 2-(ethoxymethyl)-1-(2-{[6-(4-phenylbutoxy)hexyl]oxy}ethyl)-1H-imidazo[4,5-c]quinolin-5N-oxide (0.7 g, 1.4 mmol) and dichloromethane (20 ml). The reaction was maintained for 2 hours and sodium methoxide (2.5 ml, 25% in methanol) was added dropwise. The reaction was maintained overnight. The mixture was filtered and the filtrate concentrated. Purification of the filtrate by flash column chromatography (silica gel, 97:3 ethyl acetate/methanol) provided 0.22 g of 2-(ethoxymethyl)-1-(2-{[6-(4-phenylbutoxy)hexyl]oxy}ethyl)-1H-imidazo[4,5-c]quinoline-4-amine as a colorless oil.

¹H NMR (300 MHz, DMSO-d6) δ 8.10 (d, J=7.9 Hz, 1H), 7.62 (d, J=7.9 Hz, 1H), 7.43 (t, J=7.3 Hz, 1H), 7.28–7.12 (m, 6H), 6.55 (s, 2H), 4.79 (broad s, 4H), 3.82 (t, J=5.3 Hz, 2H), 3.55 (q, J=7.0 Hz, 2H), 3.33–3.22 (m, 6H), 2.56 (t, J=7.2 Hz, 2H), 1.62–1.33 (m, 8H), 1.18–1.10 (m, 7H);

MS (EI) m/e 518.3263 (518.3256 Calculated for $C_{31}H_{42}N_4O_3$);

Analysis: Calculated for $C_{31}H_{42}N_4O_3$: % C, 71.78; % H, 8.16; % N, 10.80. Found: % C, 71.20; % H, 8.39; % N, 10.68.

Example 21

1-{2-[3-(Benzyloxy)propoxy]ethyl}-2-(ethoxymethyl)-1H-imidazo[4,5-c]quinolin-4-amine

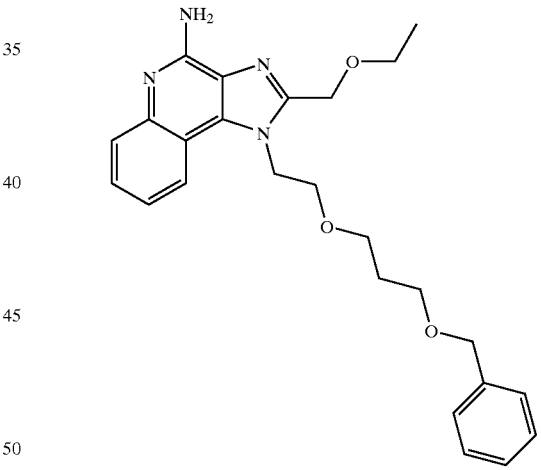

A solution of 2-[2-(ethoxymethyl)-1H-imidazo[4,5-c]quinolin-1-yl]ethanol (1.0 g, 3.7 mmol) in N,N-dimethylformamide was added dropwise to a suspension of sodium hydride (0.19 g of a 60% dispersion in mineral oil, 4.8 mmol) in N,N-dimethylformamide (20 ml). The reaction was maintained for 2 hours followed by the dropwise addition of benzyl 3-bromopropyl ether (0.72 ml, 4.1 mmol). The reaction was stirred overnight at 100° C., quenched by pouring over ice, and extracted with ethyl acetate. The organic fractions were washed with water, dried (MgSO₄), filtered, and concentrated. The crude product was purified by flash column chromatography (silica gel, 4:1 ethyl acetate/hexanes) to provide 0.45 g of 1-{2-[3-(benzyloxy)propoxy]ethyl}-2-(ethoxymethyl)-1H-imidazo[4,5-c]quinoline as a brown oil 1-{2-[3-(benzyloxy)propoxy]ethyl}-2-(ethoxymethyl)-1H-imidazo[4,5-c]quinoline was converted to 1-{2-[3-(benzyloxy)propoxy]ethyl}-2-(ethoxymethyl)-1H-imidazo[4,5-c]quinolin-4-amine using the general methods described in Parts B and C of Example 20. Purification by flash column chromatography (silica gel, 95/5 ethyl acetate/methanol) provided the desired product as a colorless oil.

$^1$H NMR (300 MHz, DMSO-d6) δ 8.11 (dd, J=8.2, 0.8 Hz, 1H), 7.62 (dd, J=8.3, 1.2 Hz, 1H), 7.44 (dt, J=7.6, 1.2 Hz, 1H), 7.32–7.19 (m, 6H), 6.56 (s, 2H), 4.85–4.77 (m, 4H), 4.26 (s, 2H), 3.84 (t, J=5.4 Hz, 2H), 3.54 (q, J=7.0 Hz, 2H), 3.40 (t, J=6.2 Hz, 2H), 3.26 (t, J=6.2 Hz, 2H), 1.63 (pentet, J=6.3 Hz, 2H), 1.15 (t, J=7.0 Hz, 3H);

$^{13}$C NMR (125 MHz, DMSO-d6) δ 152.0, 149.5, 145.2, 138.5, 133.3, 128.1, 127.4, 127.3, 126.8, 126.3, 126.25, 121.0, 120.6, 114.8, 71.8, 69.0, 67.5, 66.3, 65.4, 64.4, 45.4, 29.4, 14.9;

IR (KBr) 3305, 174, 2970, 2925, 2864, 1633, 1583, 1533, 1481, 1437, 1386, 1099, 754, 737, 698 cm$^{-1}$;

MS (EI) m/e 434.2318 (434.2317 Calculated for $C_{25}H_{30}N_4O_3$).

Example 22

1-[2-(3-Phenylpropoxy)ethyl]-1H-imidazo[4,5-c]quinolin-4-amine

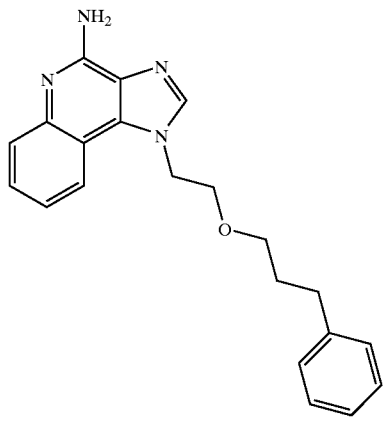

According to the general method of Example 20 (Parts A–C), 2-(1H-imidazo[4,5-c]quinolin-1-yl)ethanol and (3-bromopropyl)benzene were combined to provide 1-[2-(3-phenylpropoxy)ethyl]-1H-imidazo[4,5-c]quinolin-4-amine as a white solid.

$^1$H NMR (300 MHz, DMSO-d6) δ 8.17 (s, 1H), 8.12 (d, J=7.2 Hz, 1H), 7.64 (dd, j=8.3, 1.0 Hz, 1H), 7.45 (m, 1H), 7.24 (m, 1H), 7.16–7.08 (m, 3H), 6.92–6.89 (m, 2H), 6.60 (s, 2H), 4.81 (t, J=5.1 Hz, 2H), 3.82 (t, J=5.1 Hz, 2H), 3.29 (t, J=6.1 Hz, 2H), 2.38 (m, 2H), 1.63 (m, 2H), 1.56–1.25 (m, 8H), 0.88 (t, J=7.2 Hz, 3H);

$^{13}$C NMR (75 MHz, CDCl$_3$) δ 151.5, 144.9, 142.6, 141.4, 132.6, 128.3, 128.2, 127.4, 127.1, 125.8, 122.2, 119.8, 115.4, 70.4, 68.6, 47.6, 32.0, 30.9;

MS (EI) m/e 347.1882 (347.1872 Calculated for $C_{21}H_{22}N_4O$).

Example 23

1-(2-{[3-(3,4-Dimethylphenyl)-2-propynyl]oxy}ethyl]-1H-imidazo[4,5-c]quinolin-4-amine

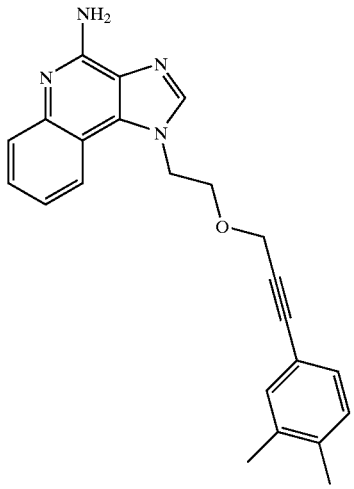

Under a nitrogen atmosphere, 1-[2-(2-propynyloxy)ethyl]-1H-imidazo[4,5-c]quinolin-4-amine (0.5 g, 1.9 mmol), copper (I) iodide (0.036 g, 0.2 mmol), 4-iodo-orthoxylene (0.5 g, 2.1 mmol) and pyrrolidine (10 mL) were combined and stirred at ambient temperature. Dichlorobis(triphenylphosphine)palladium(II) (0.066 g, 0.1 mmol) was added and the reaction mixture was stirred at ambient temperature for 1 hour. Analysis by TLC (30% methanol in chloroform) indicated that starting material was still present. The reaction mixture was heated at 65° C. overnight. The pyrrolidine was removed under reduced pressure. The resulting residue was triturated with dichloromethane containing methanol. The insoluble material was isolated by filtration and then recrystallized from toluene (40 mL) to provide 0.1 g of 1-(2-{[3-(3,4-dimethylphenyl)-2-propynyl]oxy}ethyl]-1H-imidazo[4,5-c]quinolin-4-amine as a solid, m.p. 214–216° C. Analysis: Calculated for $C_{23}H_{22}N_4O$: % C, 74.57; % H, 5.99; % N, 15.12; Found: % C, 74.24; % H, 5.98; % N, 15.08.

$^1$H-NMR (300 MHz; DMSO-d6)δ(ppm) 8.167 (s, 1H), 8.112 (d, J=7.3 Hz, 1H), 7.628 (d, J=8.3 Hz, 1H), 7.44 (t, J=7.3 Hz, 1H), 7.232 (t, J=6.8 Hz, 1H), 7.078 (d, J=7.8 Hz, 1H), 7.024 (s, 1H), 6.952 (d, J=7.9 Hz, 1H), 6.586 (s, 2H), 4.849 (t, J=5 Hz, 2H), 4.365 (s, 2H), 4.015 (t, J=5.6 Hz, 2H), 2.197 (s, 3H), 2.159 (s, 3H).

Examples 24–27

The compounds in the table below were prepared according to the synthetic method of Reaction Scheme I above using the following general method.

2-(4-Amino-1H-imidazo[4,5-c]quinolin-1-yl)-2-ethylethanol (25 mg) was placed in a 2 dram (7.4 mL) vial. Sodium hydride (1.75 eq of 60% in mineral oil) and N,N-dimethylformamide (1 mL) were added. The vial was placed on a sonicator for about 10 minutes at ambient temperature to allow the alkoxide to form. The halide (1.75 eq) was added and the vial was placed back on the sonicator for about 30 to 60 minutes at ambient temperature. The reaction mixture was analyzed by LC/MS to confirm the formation of the desired product. The reaction mixture was purified by semi-preparative HPLC. The semi-prep HPLC fractions were analyzed by LC-APCI/MS and the appropriate fractions were combined and lyophilized to provide the trifluoroacetate salt of the desired product, which was confirmed by accurate mass and ¹H NMR. The table below shows the structure of the free base and the theoretical mass (TM) and the measured mass (MM).

| Example # | Structure of the Free Base | Purification Method | Mass Measurement (Da.) |
|---|---|---|---|
| 24 | | A | TM = 346.1794<br>MM = 346.1795 |
| 25 | | A | TM = 360.1950<br>MM = 360.1955 |
| 26 | | A | TM = 414.1667<br>MM = 414.1678 |

| Example # | Structure of the Free Base | Purification Method | Mass Measurement (Da.) |
|---|---|---|---|
| | -continued | | |
| 27 | ![structure with NH2, imidazoquinoline, O-CH2-C6H4-Br] | A | TM = 424.0899<br>MM = 424.0902 |

Examples 28–41

The compounds in the table below were prepared according to the synthetic method of Reaction Scheme I above using the following general method.

The 4-amino-1H-imidazo[4,5-c]quinolin-1-yl alcohol (25 mg) was placed in a 2 dram (7.4 mL) vial. Sodium hydride (1.2 eq of 60% in mineral oil) and N,N-dimethylformamide (1 mL) were added. The vial was placed on a sonicator for about 1 hour at 50° C. to allow the alkoxide to form. The halide (1.2 eq) was added and the vial was placed back on the sonicator for about 1 to 2 hours at 50° C. The reaction mixture was analyzed by LC/MS to confirm the formation of the desired product. The reaction mixture was purified by semi-preparative HPLC. The semi-prep HPLC fractions were analyzed by LC-APCI/MS and the appropriate fractions were combined and lyophilized to provide the trifluoroacetate salt of the desired product, which was confirmed by accurate mass and $^1$H NMR. The table below shows the structure of the free base and the theoretical mass (TM) and the measured mass (MM).

| Example # | Structure of the Free Base | Purification Method | Mass Measurement (Da.) |
|---|---|---|---|
| 28 | ![structure with NH2, imidazoquinoline, CH2-CH(Ph)-O-CH2-Ph] | A | TM = 394.1794<br>MM = 394.1791 |

-continued

| Example # | Structure of the Free Base | Purification Method | Mass Measurement (Da.) |
|---|---|---|---|
| 29 | | A | TM = 428.1404<br>MM = 428.1396 |
| 30 | | A | TM = 428.1404<br>MM = 428.1397 |
| 31 | | A | TM = 408.1950<br>MM = 408.1956 |
| 32 | | A | TM = 408.1950<br>MM = 408.1956 |

-continued
| Example # | Structure of the Free Base | Purification Method | Mass Measurement (Da.) |
|---|---|---|---|
| 33 | 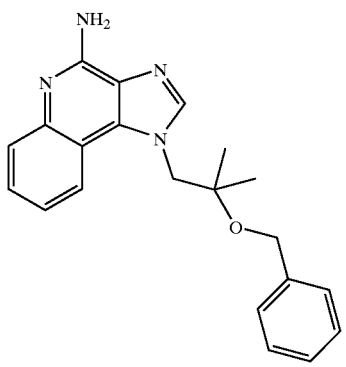 | A | TM = 346.1794<br>MM = 346.1791 |
| 34 | 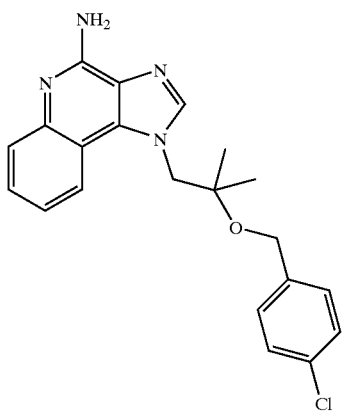 | A | TM = 380.1404<br>MM = 380.1399 |
| 35 | 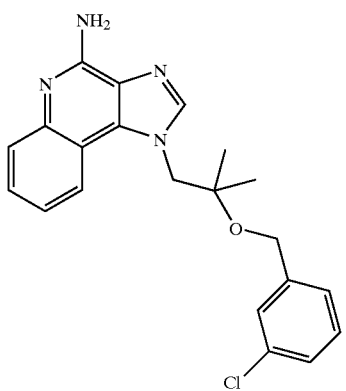 | A | TM = 380.1404<br>MM = 380.1399 |

| Example # | Structure of the Free Base | Purification Method | Mass Measurement (Da.) |
| --- | --- | --- | --- |
| 36 | | A | TM = 360.1950<br>MM = 360.1942 |
| 37 | | A | TM = 360.1950<br>MM = 360.1941 |
| 38 | | A | TM = 380.1404<br>MM = 380.1400 |
| 39 | | A | TM = 371.1746<br>MM = 371.1751 |

-continued

| Example # | Structure of the Free Base | Purification Method | Mass Measurement (Da.) |
|---|---|---|---|
| 40 | 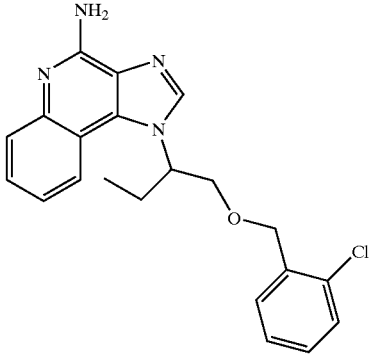 | A | TM = 380.1404<br>MM = 380.1398 |
| 41 | 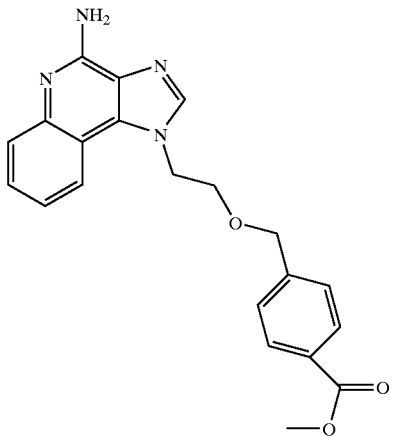 | A | TM = 376.1535<br>MM = 376.1536 |

Examples 42–88

The compounds in the table below were prepared according to the synthetic method of Reaction Scheme I above using the following general method.

The 4-amino-1H-imidazo[4,5-c]quinolin-1-yl alcohol (25 mg) was placed in a 2 dram (7.4 mL) vial. Sodium hydride (1.2 eq of 60% in mineral oil) and N,N-dimethylformamide (1 mL) were added. The vial was placed on a sonicator for about 15 to 30 minutes at ambient temperature to allow the alkoxide to form. The halide (1.2 eq) was added and the vial was placed back on the sonicator for about 15 to 120 minutes at ambient temperature. The reaction mixture was analyzed by LC/MS to confirm the formation of the desired product. The reaction mixture was purified by semi-preparative HPLC. The semi-prep HPLC fractions were analyzed by LC-APCI/MS and the appropriate fractions were combined and lyophilized to provide the trifluoroacetate salt of the desired product, which was confirmed by accurate mass and $^1$H NMR. The table below shows the structure of the free base and the theoretical mass (TM) and the measured mass (MM) or nominal mass (NM).

| Example # | Structure of the Free Base | Purification Method | Mass Measurement (Da.) |
|---|---|---|---|
| 42 | | A | TM = 318.1481<br>MM = 318.1482 |
| 43 | | A | TM = 328.1535<br>MM = 328.1534 |
| 44 | | A | TM = 377.1488<br>MM = 377.1487 |
| 45 | | A | TM = 430.1617<br>MM = 430.1614 |

-continued

| Example # | Structure of the Free Base | Purification Method | Mass Measurement (Da.) |
|---|---|---|---|
| 46 | | A | TM = 371.1746<br>MM = 371.1746 |
| 47 | | A | TM = 380.1404<br>MM = 380.1394 |
| 48 | | A | TM = 430.1617<br>MM = 430.1613 |

-continued

| Example # | Structure of the Free Base | Purification Method | Mass Measurement (Da.) |
|---|---|---|---|
| 49 | | A | TM = 360.1950<br>MM = 360.1949 |
| 50 | | A | TM = 346.1794<br>MM = 346.1781 |
| 51 | | A | TM = 363.1331<br>MM = 363.1324 |
| 52 | | A | TM = 366.1247<br>MM = 366.1243 |

| Example # | Structure of the Free Base | Purification Method | Mass Measurement (Da.) |
|---|---|---|---|
| 53 | 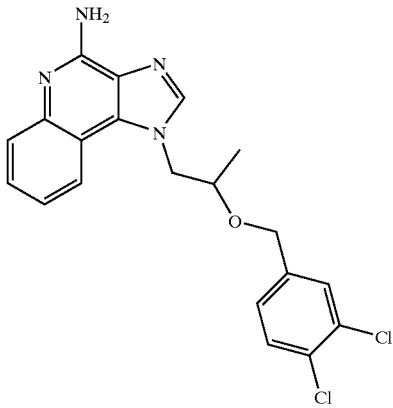 | A | TM = 400.0858<br>MM = 400.0856 |
| 54 | 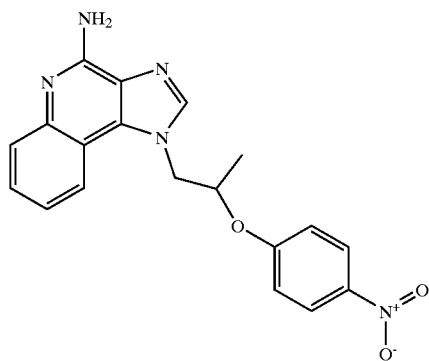 | A | TM = 364.1331<br>MM = 364.1352 |
| 55 | 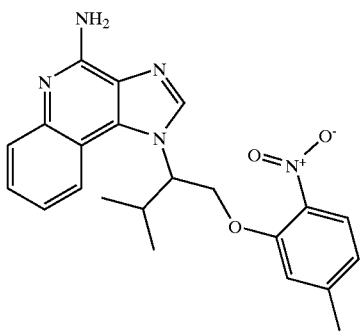 | A | TM = 405.1801<br>MM = 405.1794 |
| 56 | 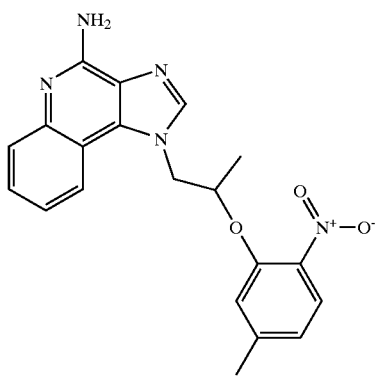 | A | TM = 377.1488<br>MM = 377.1490 |

-continued

| Example # | Structure of the Free Base | Purification Method | Mass Measurement (Da.) |
|---|---|---|---|
| 57 | | A | TM = 391.1644<br>MM = 391.1637 |
| 58 | | A | TM = 391.1644<br>MM = 391.1637 |
| 59 | | A | TM = 360.1950<br>MM = 360.1938 |
| 60 | | A | TM = 394.1560<br>MM = 394.1558 |

-continued

| Example # | Structure of the Free Base | Purification Method | Mass Measurement (Da.) |
|---|---|---|---|
| 61 | | A | TM = 394.1560<br>MM = 294.1557 |
| 62 | | A | TM = 428.1171<br>MM = 428.1159 |
| 63 | | A | TM = 428.1824<br>MM = 428.1826 |
| 64 | | A | TM = 385.1903<br>MM = 385.1904 |

-continued
| Example # | Structure of the Free Base | Purification Method | Mass Measurement (Da.) |
|---|---|---|---|
| 65 | 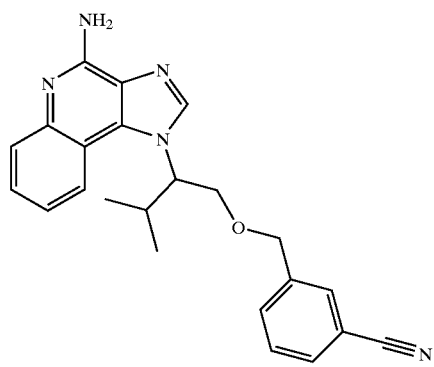 | A | TM = 385.1903<br>MM = 385.1897 |
| 66 | 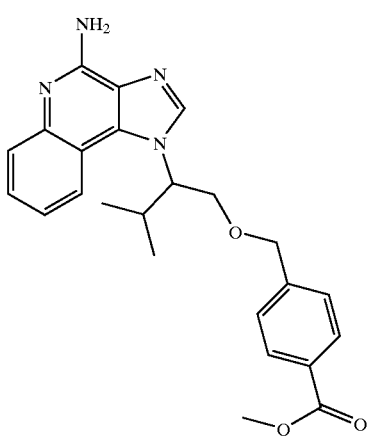 | A | TM = 418.2005<br>MM = 418.2013 |
| 67 | 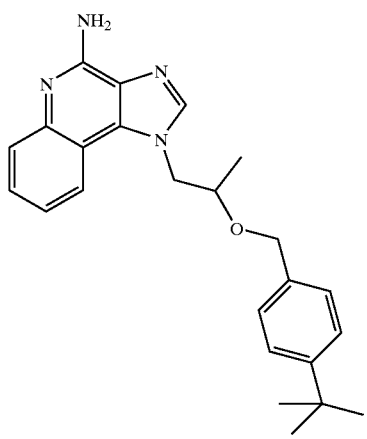 | A | TM = 388.2263<br>MM = 388.2257 |

| Example # | Structure of the Free Base | Purification Method | Mass Measurement (Da.) |
|---|---|---|---|
| 68 | 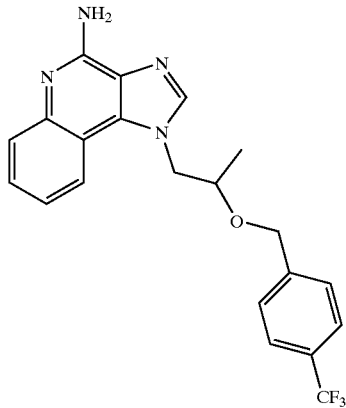 | A | TM = 400.1511<br>MM = 400.1507 |
| 69 | 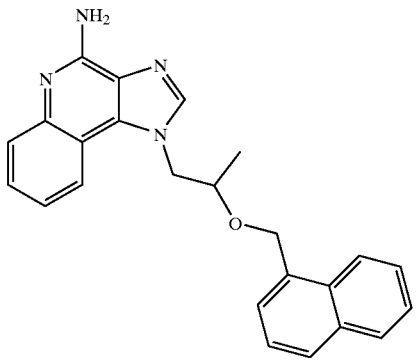 | A | TM = 382.1794<br>MM = 382.1788 |
| 70 | 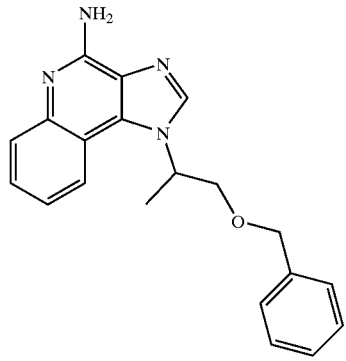 | A | TM = 332.1637<br>MM = 332.1641 |

-continued
| Example # | Structure of the Free Base | Purification Method | Mass Measurement (Da.) |
|---|---|---|---|
| 71 | 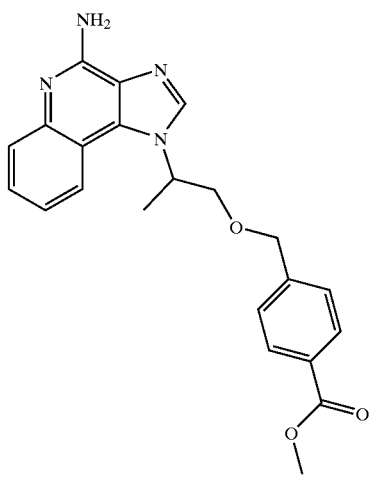 | A | TM = 390.1692<br>MM = 390.1697 |
| 72 | 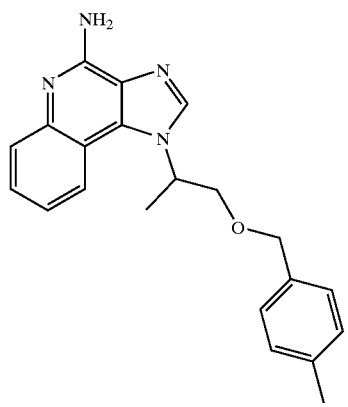 | A | TM = 346.1794<br>MM = 346.1791 |
| 73 | 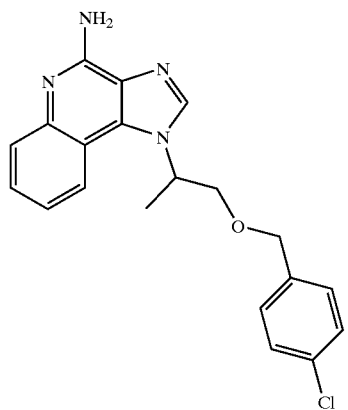 | A | TM = 366.1247<br>MM = 366.1241 |

-continued

| Example # | Structure of the Free Base | Purification Method | Mass Measurement (Da.) |
|---|---|---|---|
| 74 | | A | TM = 400.1511<br>MM = 400.1512 |
| 75 | | A | TM = 346.1794<br>MM = 346.1799 |
| 76 | | A | TM = 360.1950<br>MM = 360.1953 |

| Example # | Structure of the Free Base | Purification Method | Mass Measurement (Da.) |
|---|---|---|---|
| 77 | | A | TM = 360.1950<br>MM = 360.1941 |
| 78 | | A | TM = 414.1667<br>MM = 414.1670 |
| 79 | | A | TM = 452<br>NM [M + H]$^{+1}$ = 453 |

-continued

| Example # | Structure of the Free Base | Purification Method | Mass Measurement (Da.) |
|---|---|---|---|
| 80 | | A | TM = 360<br>NM [M + H]$^{+1}$ = 361 |
| 81 | | A | TM = 360<br>NM [M + H]$^{+1}$ = 361 |
| 82 | | A | TM = 374<br>NM [M + H]$^{+1}$ = 375.2 |
| 83 | | B | TM = 379.1281<br>MM = 379.1278 |

-continued

| Example # | Structure of the Free Base | Purification Method | Mass Measurement (Da.) |
|---|---|---|---|
| 84 | | B | TM = 348.1586<br>MM = 348.1588 |
| 85 | | B | TM = 362.1743<br>MM = 362.1736 |
| 86 | | B | TM = 362.1743<br>MM = 362.1748 |

| Example # | Structure of the Free Base | Purification Method | Mass Measurement (Da.) |
|---|---|---|---|
| 87 | | B | TM = 373.1539<br>MM = 373.1546 |
| 88 | | B | TM = 373.1539<br>MM = 373.1543 |

Examples 89–96

The compounds in the table below were prepared according to the synthetic method of Reaction Scheme V above using the following general method.

2-(4-Amino-2-butyl-6,7,8,9-tetrahydro-1H-imidazo[4,5-c]quinolin-1-yl)ethanol (25 mg) was placed in a 2 dram (7.4 mL) vial. Sodium hydride (1.2 eq of 60% in mineral oil) and N,N-dimethylformamide (1 mL) were added. The vial was placed on a sonicator for about 15 minutes at ambient temperature to allow the alkoxide to form. The halide (1.2 eq) was added and the vial was placed back on the sonicator for about 15 minutes at ambient temperature. The reaction mixture was analyzed by LC/MS to confirm the formation of the desired product. The reaction mixture was purified by semi-preparative HPLC. The semi-prep HPLC fractions were analyzed by LC-APCI/MS and the appropriate fractions were combined and lyophilized to provide the trifluoroacetate salt of the desired product, which was confirmed by accurate mass and $^1$H NMR. The table below shows the structure of the free base and the theoretical mass (TM) and the measured mass (MM).

| Example # | Structure of the Free Base | Purification Method | Mass Measurement (Da.) |
|---|---|---|---|
| 89 | 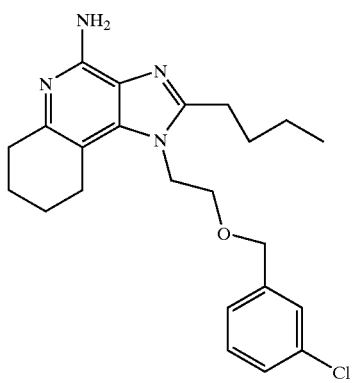 | B | TM = 412.2030<br>MM = 412.2023 |
| 90 | 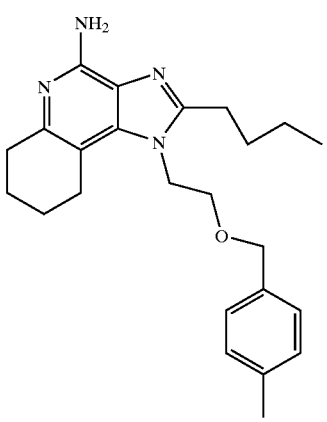 | B | TM = 392.2576<br>MM = 392.2575 |
| 91 | 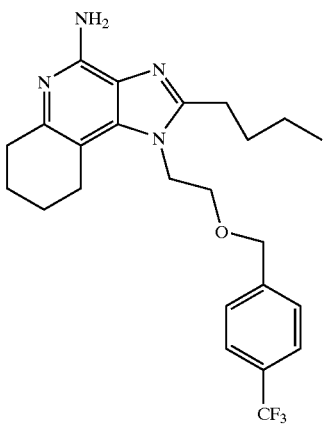 | B | TM = 446.2293<br>MM = 446.2287 |

-continued

| Example # | Structure of the Free Base | Purification Method | Mass Measurement (Da.) |
|---|---|---|---|
| 92 | | B | TM = 446.2293<br>MM = 446.2288 |
| 93 | | B | TM = 403.2372<br>MM = 403.2365 |
| 94 | | B | TM = 403.2372<br>MM = 403.2370 |

| Example # | Structure of the Free Base | Purification Method | Mass Measurement (Da.) |
|---|---|---|---|
| 95 | | B | TM = 434.3046<br>MM = 434.3047 |
| 96 | | B | TM = 409.2114<br>MM = 409.2117 |

Examples 97–100

The compounds in the table below were prepared according to the synthetic method of Reaction Scheme III above using the following general method.

A 1 mL portion of a solution prepared by dissolving 0.5 g of 1-(4-amino-1H-imidazo[4,5-c]quinolin-1-yl)propan-2-ol in N,N-dimethylformamide (20 mL) was added to a 2 dram (7.4 mL) glass vial containing the phenol (2 eq.). Triphenylphosphine (54 mg, 2 eq.) dissolved in N,N-dimethylformamide (1 mL) was added to the vial. The resulting slurry was sonicated to dissolve the phenol. Diethyl azodicarboxylate (36 mg, 2 eq.) was added neat. The reaction mixture was sonicated for about 30 minutes and then shaken overnight at ambient temperature. The reaction mixture was purified by semi-preparative HPLC using Method A. The compounds of Examples 99 and 100 were provided as the trifluoroacetate salts The products were confirmed by accurate mass and $^1$H NMR. The table below shows the structure of the free base and the theoretical mass (TM) and the

| Example # | Structure | Mass Measurement |
|---|---|---|
| 97 | 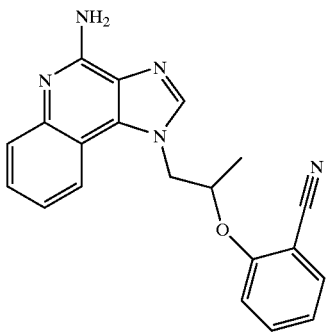 | TM = 343<br>NM[M + H]$^{+1}$ = 344 |

-continued

| Example # | Structure | Mass Measurement |
|---|---|---|
| 98 | 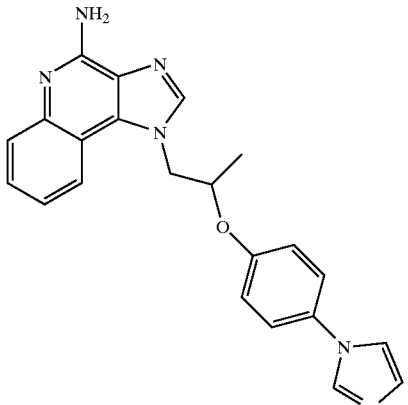 | TM = 384<br>NM[M + H]$^{+1}$ = 385 |
| 99 | 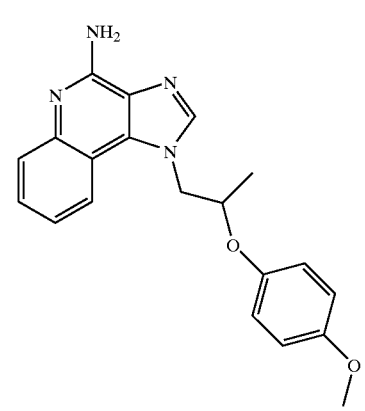 | TM = 348<br>NM[M + H]$^{+1}$ = 349 |
| 100 | 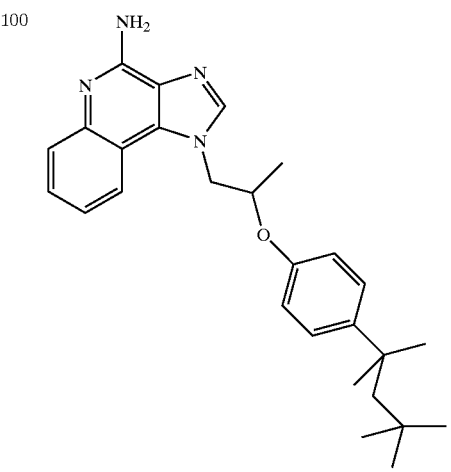 | TM = 430<br>NM[M + H]$^{+1}$ = 431 |

Examples 101–104

The compounds in the table below were prepared according to the synthetic method of Reaction Scheme III above using the following general method.

A 1 mL portion of a solution prepared by dissolving 0.5 g of 2-(4-amino-1H-imidazo[4,5-c]quinolin-1-yl)-2-ethylethanol in N,N-dimethylformamide (20 mL) was added to a 4 dram (15 mL) glass vial containing the phenol (2 eq.). Triphenylphosphine (51 mg, 2 eq.) dissolved in N,N-dimethylformamide (1 mL) was added to the vial. Diethyl azodicarboxylate (34 mg, 2 eq.) was added neat. The resulting solution was sonicated for about 2 minutes and then shaken overnight at ambient temperature. Analysis by HPLC indicated that the reaction was not complete. The solvent was removed under vacuum. The resulting oil was dissolved in 1 mL of tetrahydrofuran containing triphenylphosphine (2 eq.). Diethyl azodicarboxylate (2 eq.) was added neat. The reaction mixture was shaken at ambient temperature overnight. Analysis by HPLC indicated that the reaction was complete. The reaction mixture was purified by semi-preparative HPLC using Method B The semi-prep HPLC fractions were analyzed by LC-APCI/MS and the appropriate fractions were combined and lyophilized to provide the trifluoroacetate salt of the desired product, which was confirmed by accurate mass and $^1$H NMR. The table below shows the structure of the free base and the theoretical mass (TM) and the nominal mass (NM).

| Example # | Structure of the Free Base | Mass Measurement |
|---|---|---|
| 101 | 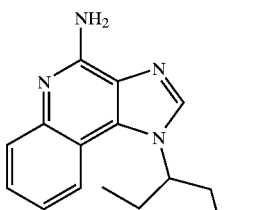 | TM = 398<br>NM[M + H]$^{+1}$ = 399 |
| 102 | 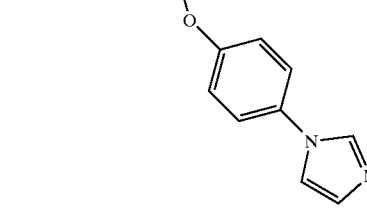 | TM = 357<br>NM[M + H]$^{+1}$ = 358 |

-continued

| Example # | Structure of the Free Base | Mass Measurement |
|---|---|---|
| 103 | 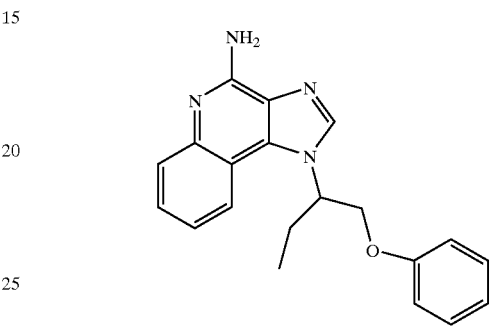 | TM = 444<br>NM[M + H]$^{+1}$ = 445 |
| 104 | 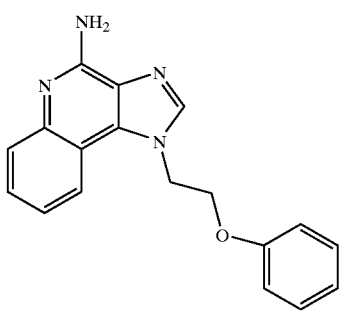 | TM = 389<br>NM[M + H]$^{+1}$ = 390 |

Example 105

1-(2-Phenoxyethyl)-1H-imidazo[4,5-c]quinolin-4-amine

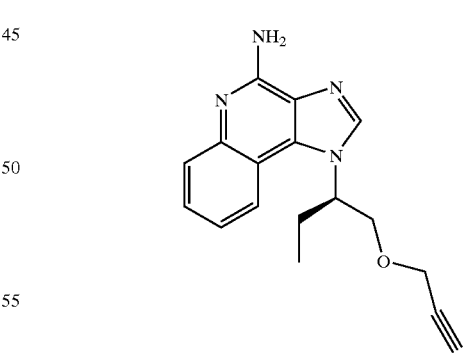

2-(4-Amino-1H-imidazo[4,5-c]quinolin-1-yl)ethanol (25 mg, 0.108 mmol) and N,N-dimethylformamide (1 mL) were combined. Phenol (12 mg, 0.130 mmol) and triphenylphosphine (34 mg, 0.130 mmol) were added and the resulting slurry was sonicated for about 1 minute. Diethyl azodicarboxylate (23 mg, 0.130 mmol) was added and the reaction mixture was shaken at ambient temperature for 24 hours. Analysis by LC-MS showed that a major amount of starting material remained. An additional equivalent each of phenol, triphenylphosphine and diethyl azodicarboxylate were added. The reaction mixture was sonicated for 30 minutes. After 1 hour analysis by LC-MS showed product. The solvent was removed and the residue was purified by semi-preparative HPLC using Method A. Mass Measurement: TM=304, NM[M+H]$^{+1}$=305.

Example 106

1-[(1-Phenoxymethyl)propyl]-1H-imidazo[4,5-c]quinolin-4-amine 2-(4-Amino-1H-imidazo[4,5-c]quinolin-1-yl)-2-ethylethanol (50 mg, 0.195 mmol) and N,N-dimethylformamide (2 mL) were combined. Phenol (37 mg, 0.390 mmol) and triphenylphosphine (102 mg) were added followed by diethyl azodicarboxylate (67 mg, 0.390 mmol). The resulting solution was sonicated for 1 hour. Analysis by LC-MS showed product and a small amount of starting material. The solvent was removed and the residue was purified by semi-preparative HPLC using Method A. Mass Measurement: TM=332, NM[M+H]$^{+1}$=333.

Example 107

1-{(1R)-1-[(Prop-2-ynyloxy)methyl]propyl}-1H-imidazo[4,5-c]quinolin-4-amine

Part A

Crude 4-chloro-3-nitroquinoline (413.8 g, 1 eq.) was dissolved in dichloromethane (1.65 L). The solution was heated to reflux and then filtered through a layer of Celite® filter agent. The filtrate was cooled to 5° C. with stirring. Triethylamine (305.4 mL, 1.1 eq.) was added in a single portion. The reaction mixture was stirred for 15 minutes. (R)-(−)-2-Amino-1-butanol (205 mL, 1.1 eq.) was added dropwise while maintaining the temperature of the reaction mixture below 40° C. The reaction mixture was allowed to stir at ambient temperature for several days. The reaction mixture was cooled to −30° C. A yellow precipitate was isolated by filtration, washed with very cold dichloromethane and then sucked dry. The solid was slurried for 1 hour with cold 80/20 water/methanol (1 L), isolated by filtration, washed with cool water, washed with very cold methanol (2×300 mL), and then sucked dry on the filter overnight to provide 475 g of (2R)-2-[(3-nitroquinolin-4-yl) amino]butan-1-ol.

Part B (2R)-2-[(3-Nitroquinolin-4-yl)amino]butan-1-ol (238 g), isopropanol (5 L) and catalyst (23.8 g of 5% platinum on carbon) were combined in a stainless steel vessel and hydrogenated at 50 psi (3.5 Kg/cm$^2$) for 16 hours. The reaction mixture was filtered through a layer of Celite® filter agent to remove the catalyst. The filtrate was concentrated under reduced pressure to provide 208.3 g of (2R)-2-[(3-aminoquinolin-4-yl)amino]butan-1-ol as an amber oil. The reaction was run a second time on the same scale.

Part C (2R)-2-[(3-Aminoquinolin-4-yl)amino]butan-1-ol (416.0 g, 1 eq.) and triethylorthoformate (1.2 L, 4 eq.) were combined and slowly heated to 145° C. Ethanol was distilled off as it formed during the reaction. After 500 mL of ethanol had been distilled off, the reaction mixture was allowed to cool to 50° C. under a nitrogen atmosphere. Excess triethyLorthoformate was removed under reduced pressure to provide crude (2R)-2-(1H-imidazo[4,5-c]quinolin-1-yl) butan-1-ol.

Part D

A mixture of (2R)-2-(1H-imidazo[4,5-c]quinolin-1-yl) butan-1-ol (434.3 g) and acetic anhydride (1.2 L) was slowly heated over a period of about 2 hours to 100° C. The reaction mixture was allowed to cool to ambient temperature overnight. Methanol (2.5 L) was added and the reaction mixture exothermed to produce a vigorous reflux. The reaction mixture was heated at reflux for an additional 2 hours, cooled to ambient temperature and then concentrated under reduced pressure. The residue was diluted with water and then made basic with sodium bicarbonate. Analysis of the resulting oil by TLC (20% methanol in ethyl acetate) showed two products and no starting material. The oil was extracted into ethyl acetate. The organic layer was washed with water, dried over magnesium sulfate, filtered and then concentrated under reduced pressure to provide 359.3 g of a residue. This material was combined with acetic anhydride (1.6 L) and then heated to reflux for 1 hour. The reaction mixture was allowed to cool to ambient temperature overnight and then concentrated under reduced pressure. Analysis of the residue by TLC showed a single product spot. The residue was diluted with water (1 L), made basic (pH 8) with saturated sodium bicarbonate solution and then stirred for 1 hour. The resulting precipitate was isolated by filtration, washed with water and then dried in a vacuum oven overnight at 60° C. to provide (2R)-2-(1H-imidazo[4,5-c] quinolin-1-yl)butyl acetate as a brown solid.

Part E

Sodium methoxide (163.0 g of 25% in methanol, 1.1 eq.) was added in a single portion to a solution of (2R)-2-(1H-imidazo[4,5-c]quinolin-1-yl)butyl acetate (194.0 g, 1 eq.) in methanol (970 mL). The reaction mixture was stirred at ambient temperature for 3 hours and then concentrated under reduced pressure. The residue was diluted with water (1 L), neutralized (pH 6–7) with acetic acid and then stirred at ambient temperature overnight. The resulting precipitate was isolated by filtration, washed with water (2×200 mL), air dried on the filter and then dried in a vacuum oven overnight at 50° C. to provide 145.5 g of (2R)-2-(1H-imidazo[4,5-c]quinolin-1-yl)butan-1-ol as a solid.

Part F (2R)-2-(1H-Imidazo[4,5-c]quinolin-1-yl)butan-1-ol (19 g, 78.8 mmol) was added to a mixture of sodium hydroxide (124 mL of 50%), dichloromethane (150 mL), benzyltrimethyl ammonium chloride (0.73 g), and propargyl bromide (11.4 mL, 102 mmol). The reaction mixture was allowed to stir at ambient temperature overnight. The reaction mixture was diluted with dichloromethane and water. The aqueous fraction was extracted multiple times with dichloromethane. The organic fractions were combined, washed with water, dried over magnesium sulfate, filtered and then concentrated under reduced pressure. The residue was purified by column chromatography eluting with ethyl acetate to provide 20.9 g of 1-{(1R)-1-[(prop-2-ynyloxy)methyl]propyl}-1H-imidazo [4,5-c]quinoline as a brown liquid.

Part G

3-Chloroperoxybenzoic acid (15.0 g of 57–86%) was added to a chilled (0°) mixture of the material from Part F and chloroform (250 mL). After 0.5 hour the reaction mixture was allowed to warm to ambient temperature. The progress of the reaction was monitored by TLC and two additional portions of 3-chloroperoxybenzoic acid (3.75 g) were added. When the reaction was complete, it was washed with sodium bicarbonate. The aqueous fraction was extracted with ethyl acetate. The organic fractions were combined, dried over magnesium sulfate, filtered and then concentrated under reduced pressure to provide 1-{(1R)-1-[(prop-2-ynyloxy)methyl]propyl}-1H-imidazo[4,5-c] quinoline-5N-oxide as a brown oil which solidified overnight.

Part H

Trichloroacetyl isocyanate (10.7 mL) was added dropwise to a mixture of the material from Part G and anhydrous dichloromethane (300 mL). After 1 hour analysis by TLC indicated that the reaction was not complete so more trichloroacetyl isocyanate (2 mL) was added. After 1 hour the reaction mixture was concentrated under reduced pressure to provide 2,2,2-trichloro-N-(1-{(1R)-1-[(2-propynyloxy) methyl]propyl}-1H-imidazo[4,5-c]quinolin-4-yl)acetamide as a yellow solid.

Part I

Sodium methoxide (57.5 mL of 25% in methanol) was added to a mixture of the material from Part H and methanol (250 mL). The reaction mixture turned homogeneous after 0.5 hour and was stirred overnight. The reaction mixture was concentrated under reduced pressure. The residue was purified by column chromatography eluting with 80/20 dichloromethane/methanol to provide a solid. The solid was washed with diethyl ether, recrystallized from toluene and then dried in an oven at 60° C. overnight to provide 9.77 g of 1-{(1R)-1-[(prop-2-ynyloxy)methyl]propyl}-1H-imidazo [4,5-c]quinolin-4-amine as a crystalline solid.

$^1$H-NMR (300 MHz, DMSO-d6) δ 8.37 (s, 1H), 8.19 (d, J=8.3 Hz, 1H), 7.65 (dd, J=8.3, 1.5 Hz, 1H), 7.44 (br t, J=7.6 Hz, 1H), 7.25 (br t, J=7.6 Hz, 1H), 6.65 (s, 2H), 5.23 (m, 1H), 4.17 (d, J=2.0 Hz, 2H), 3.90–4.10 (m, 2H), 3.46 (t, J=2.4 Hz, 1H), 2.07 (m, 2H), 0.88 (t, J=7.3 Hz, 3H).

Example 108

1-((1R)-1-{[(3-Phenylprop-2-ynyl)oxy]methyl}propyl)-1H-imidazo[4,5-c]quinolin-4-amine

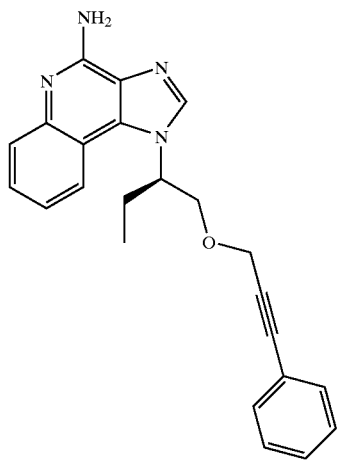

Part A

Under a nitrogen atmosphere 1-{(1R)-1-[(prop-2-ynyloxy)methyl]propyl}-1H-imidazo[4,5-c]quinolin-4-amine (0.80 g, 1.25 mmol) and anhydrous N,N-dimethylformamide (60 mL) were combined and then heated to 40° C. Dibenzyl dicarbonate (3.98 g, 13.9 mmol) was added. The reaction was monitored by TLC and HPLC. After 2 hours more dibenzyl dicarbonate (1 g) was added. After 1 hour the reaction went to completion. The reaction mixture was diluted with ethyl acetate, washed with water, washed with brine, dried over magnesium sulfate, filtered and then concentrated under reduced pressure to provide N,N-(bis benzyloxycarbonyl)-1-{(1R)-1-[(prop-2-ynyloxy)methyl]propyl}-1H-imidazo[4,5-c]quinolin-4-amine as a light brown oil. The oil was washed with hexane to remove excess dibenzyl dicarbonate.

Part B

N,N-(Bis benzyloxycarbonyl)-1-{(1R)-1-[(prop-2-ynyloxy)methyl]propyl}-1H-imidazo[4,5-c]quinolin-4-amine (1.91 g, 3.4 mmol), anhydrous acetonitrile (30 mL) and triethylamine (0.71 mL, 5.1 mmol) were combined and then heated to 70° C. Copper (I) iodide (0.026 g), dichlorobis(triphenylphosphine)palladium(II) (0.048 g) and iodobenzene (0.40 mL, 3.7 mmol) were added. The reaction was complete in 0.5 hour. The reaction mixture was diluted with ethyl acetate, washed with water, washed with brine, dried over magnesium sulfate, filtered and then concentrated under reduced pressure to provide a brown liquid. This material was purified by column chromatography eluting with 39.5/59.5/1 ethyl acetate/hexane/triethylamine to provide 2.1 g of an oil. The oil was a mixture of mono and di benzyloxycarbonyl protected 1-((1R)-1-{[(3-phenylprop-2-ynyl)oxy]methyl}propyl)-1H-imidazo[4,5-c]quinolin-4-amine.

Part C

A portion of the material from Part B (0.8 g), methanol, and sodium methoxide (1.0 mL of 25% in methanol) were combined. After 16 hours analysis by TLC indicated that the reaction was complete. The reaction mixture was concentrated under reduced pressure. The resulting oil was purified by column chromatography eluting with 5% methanol in dichloromethane to provide a glassy solid. This material was dried under high vacuum at ambient temperature overnight to provide 0.3 g of 1-((1R)-1-{[(3-phenylprop-2-ynyl)oxy]methyl}propyl)-1H-imidazo[4,5-c]quinolin-4-amine, m.p. 63–67° C.

Analysis:. Calculated for $C_{23}H_{22}N_4O$: % C, 74.57; % H, 5.99; % N, 15.12; Found: % C, 74.18; % H, 6.10; % N, 15.00.

$^1$H-NMR (300 MHz, DMSO-d6) δ 8.40 (s, 1H), 8.21 (d, J=8.3 Hz, 1H), 7.64 (dd, J=8.5, 1.2 Hz, 1H), 7.43 (br t, J=7.6 Hz, 1H), 7.25–7.40 (m, 5H), 7.22 (br t, J=7.6 Hz, 1H), 6.61 (s, 2H), 5.26 (m, 1H), 4.41 (s, 2H), 3.95–4.20 (m, 2H), 2.10 (m, 2H), 0.90 (t, J=7.3 Hz, 3H)

IR (KBr) 3306, 3171, 1634, 1526, 1100, 755 cm$^{-1}$

HRMS (EI) Calculated for $C_{23}H_{22}N_4O$ (M$^+$) 370.1794, found 370.1798.

Example 109

1-{(1R)-1-[(3-Phenylpropoxy)methyl]propyl}-1H-imidazo[4,5-c]quinolin-4-amine

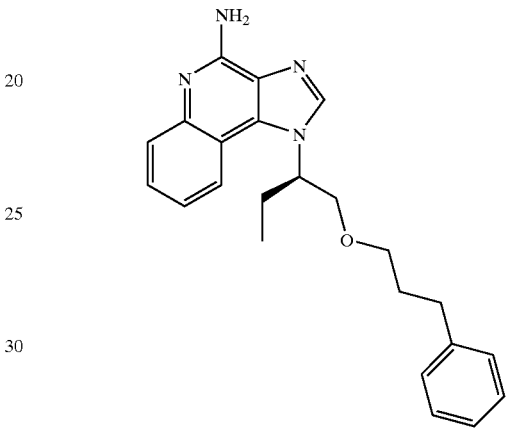

Under a nitrogen atmosphere palladium hydroxide (0.72 g of 20% on carbon) was added to a solution of material from Example 108 Part B (1.3 g) in methanol (~20 mL). The mixture was hydrogenated at 50 psi (3.5 Kg/cm$^2$) for 3.5 hours. The reaction mixture was filtered to remove the catalyst. The filtrate was concentrated under reduced pressure. The residue was purified by column chromatography eluting with 2.5% methanol in dichloromethane to provide an oil. The oil was triturated with diethyl ether to provide a solid which was isolated and dried to provide 0.4 g of 1-{(1R)-1-[(3-phenylpropoxy)methyl]propyl}-1H-imidazo[4,5-c]quinolin-4-amine as a white crystalline solid, m.p. 118–120° C.

Analysis: Calculated for $C_{23}H_{26}N_4O$: % C, 73.77; % H, 7.00; % N, 14.96. Found: % C, 73.68; % H, 7.17; % N, 14.72.

$^1$H-NMR (300 MHz, DMSO-d6) δ 8.39 (s, 1H), 8.22 (d, J=7.8 Hz, 1H), 7.65 (dd, J=8.3, 1.0 Hz, 1H), 7.44 (br t, J=7.7 Hz, 1H), 7.05–7.30 (m, 4H), 6.95 (br d, J=6.8 Hz, 2H), 6.62 (s, 2H), 5.20 (m, 1H), 3.88 (m, 2H), 3.36 (m, 2H), 2.37 (br t, J=7.6 Hz, 2H), 2.08 (m, 2H), 1.63 (m, 2H), 0.89 (t, J=7.3 Hz, 3H)

IR (KBr) 3458, 3109 1639, 1528, 1392, 1250, 760 cm$^{-1}$

HRMS (EI) Calculated for $C_{23}H_{26}N_4O$ (M$^+$) 374.2107, found 374.2104.

Examples 110–112

Part A

Triethylamine (15 mL) and R-3-amino-2-methylpropan-1-ol (about 0.1 mole of crude) were added to a solution of 2,4-dichloro-3-nitroquinoline (24.3 g, 0.1 mole) in dichloromethane (250 mL). The reaction mixture was refluxed until analysis by TLC showed no change. The reaction mixture was evaporated to dryness. The solid yellow-brown residue was crushed and then extracted repeatedly with hexane containing a small amount of dichloromethane in order to remove the starting quinoline. The residue was then recrystallized from isopropanol to provide 19.0 g of R-3-[(2-chloro-3-nitroquinolin-4-yl)amino]-2-methylpropan-1-ol as a yellow solid. A sample (500 mg) was recrystallized from isopropanol to provide a yellow crystalline solid, m.p. 174–176° C.

Part B

R-3-[(2-Chloro-3-nitroquinolin-4-yl)amino]-2-methylpropan-1-ol (10 g, 33.8 mmol), isopropanol (350 mL) and catalyst (~1 g of 5% platinum on carbon) were combined and then hydrogenated on a Parr apparatus at 50 psi (3.5 Kg/cm$^2$) initial hydrogen pressure. When hydrogen uptake had ceased, the reaction mixture was filtered to remove the catalyst. The filtrate was evaporated under reduced pressure to provide crude R-3-[(3-amino-2-chloroquinolin-4-yl)amino]-2-methylpropan-1-ol. Diethoxymethyl acetate (10.0 mL, 61.5 mmol) was added to the crude intermediate and a strong heat of reaction was observed. The resulting solution was heated on a steam bath for 20 minutes and then diluted with water and ammonium hydroxide. The resulting oil was extracted into ethyl acetate. The extracts were combined, dried over magnesium sulfate and then concentrated under reduced pressure. The resulting solid was slurried with ethyl acetate/hexane, isolated by filtration, washed with ethyl acetate/hexane and then dried to provide 6.0 g of R 3-(4-chloro-1H-imidazo[4,5-c]quinolin-1-yl)-2-methylpropan-1-ol as a yellow/tan solid.

Part C

R 3-(4-Chloro-1H-imidazo[4,5-c]quinolin-1-yl)-2-methylpropan-1-ol (1.0 g, 3.6 mmol) and methanolic ammonia (30 mL of ~15%) were combined and then heated in a steel bomb at 150° C. The container was allowed to cool to ambient temperature. Excess methanolic potassium hydroxide was added to the reaction mixture which was then concentrated under reduced pressure to decrease the volume. Water was added and then concentration was continued until a solid formed. The solid was isolated by filtration, washed with water and then dried to provide a near white solid. This material was recrystallized from methanol/dichloromethane to provide R 3-(4-amino-1H-imidazo[4,5-c]quinolin-1-yl)-2-methylpropan-1-ol as colorless solid, m.p. 258–261° C.

Analysis:

Calculated for $C_{14}H_{16}N_4O$: % C, 65.61, % H, 6.29; % N, 21.86; Found: % C, 65.50, % H, 6.3, % N, 21.7.

Part D

The compounds in the table below were prepared according to the synthetic method of Reaction Scheme I above using the following general method.

R 3-(4-Amino-1H-imidazo[4,5-c]quinolin-1-yl)-2-methylpropan-1-ol (25 mg) was placed in a 2 dram (7.4 mL) vial. Sodium hydride (1.2 equivalents of 60% in mineral oil) and N,N-dimethylformamide (1 mL) were added. The vial was placed on a sonicator for about 15 minutes at 50° C. to allow the alkoxide to form. The halide (1.2 equivalents) was added and the vial was placed back on the sonicator for about 2 hours at 50° C. The reaction mixture was analyzed by LC/MS to confirm the formation of the desired product. The reaction mixture was purified by semi-preparative HPLC. The semi-prep HPLC fractions were analyzed by LC-APCI/MS and the appropriate fractions were combined and lyophilized to provide the trifluoroacetate salt of the desired product, which was confirmed by accurate mass and $^1$H NMR. The table below shows the structure of the free base and the theoretical mass (TM) and the measured mass (MM).

| Example # | Structure of the Free Base | Purification Method | Mass Measurement (Da.) |
|---|---|---|---|
| 110 | 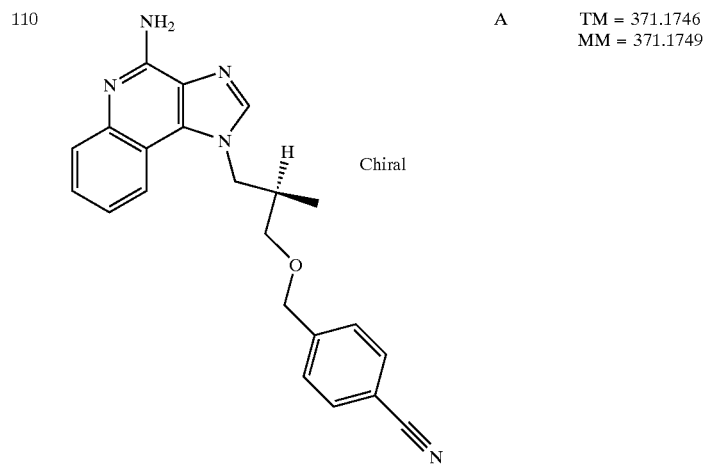 | A | TM = 371.1746<br>MM = 371.1749 |

| Example # | Structure of the Free Base | Purification Method | Mass Measurement (Da.) |
|---|---|---|---|
| 111 | Chiral | A | TM = 402.2420<br>MM = 402.2413 |
| 112 | Chiral | A | TM = 380.1404<br>MM = 380.1402 |

Example 113
1-[(Benzyloxy)methyl]-1H-imidazo[4,5-c]quinolin-4-amine

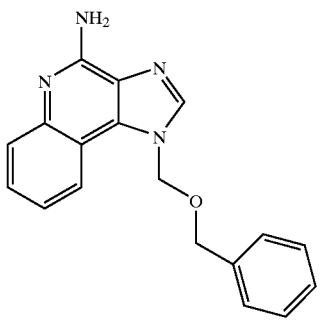

Sodium hydride (0.48 g of 60%, 11.9 mmol) was added to a suspension of 1H-imidazo[4,5-c]quinolin-4-amine (2.0 g, 10.9 mmol) in N,N-dimethylformamide. The reaction mixture was stirred at ambient temperature for 3 hours and then chilled in an ice bath. Benzyl chloromethyl ether (1.5 mL, 10.9 mmol) was added. The reaction mixture was stirred at ambient temperature for 2 hours and then heated on a steam bath for 1 hour. A precipitate was isolated by filtration. The filtrate was diluted with water and an oil separated. The oil was seeded with the precipitated solid and 2.1 g of a gummy solid was obtained. This material was slurried with refluxing ethyl acetate (~5 mL). The mixture was cooled and a precipitate was isolated by filtration. The filtrate was concentrated under reduced pressure. The resulting residue was slurried twice with ethyl acetate and then combined with the precipitate to provide 0.8 g of solid. This solid was recrystallized from ethanol (~5 mL) to provide 0.6 g of 1-[(benzyloxy)methyl]-1H-imidazo[4,5-c]quinolin-4-amine, m.p. 168–172° C.

Analysis: Calculated for $C_{18}H_{16}N_4O$: % C, 71.0; % H, 5.3; % N, 18.4; Found: % C, 70.9; % H, 5,3; % N, 18.4.

Example 114
1-(2-{3-[4-(Dimethylamino)phenyl]propoxy}ethyl)-1H-imidazo[4,5-c]quinolin-4-amine

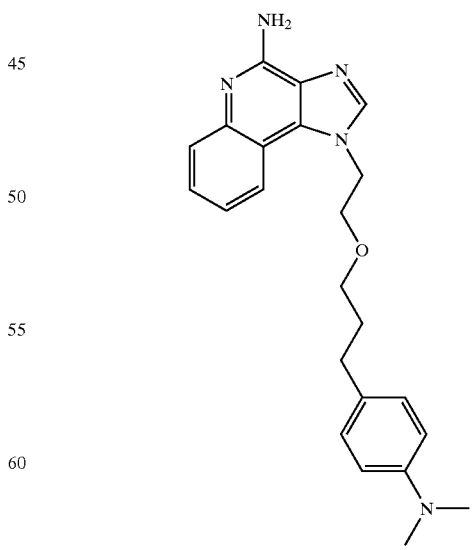

Part A

Using the general method of Example 12 Part A, N,N-(bis tert-butoxycarbonyl)-1-[2-(2-propynyloxy)ethyl]-1H- imidazo[4,5-c]quinolin-4-amine (2.5 g, 5.36 mmol) was reacted with 4-iodo-N,N-dimethylaniline (1.46 g, 5.89 mmol) at 70° C. The reaction was judged complete at 30 minutes. The solution was diluted with ethyl acetate, washed with water (3×), saturated aqueous sodium bicarbonate (3×), brine (3×), dried with anhydrous magnesium sulfate, filtered and concentrated under reduced pressure. The resulting solid was purified by chromatography over silica gel (98/2 dichloromethane/methanol) to provide 0.883 g of tert-butyl 1-[2-({3-[4-(dimethylamino)phenyl]prop-2-ynyl}oxy)ethyl]-1H-imidazo[4,5-c]quinolin-4-ylcarbamate as a brown solid.

MS (CI) for $C_{33}H_{39}N_5O_5$ m/z 586 (MH$^+$), 486, 386, 229

Part B

Using the general method of Example 12 Part B, tert-butyl 1-[2-({3-[4-(dimethylamino)phenyl]prop-2-ynyl}oxy)ethyl]-1H-imidazo[4,5-c]quinolin-4-ylcarbamate (0.883 g, 1.507 mmol) was hydrogenated to provide 0.783 g of tert-butyl 1-(2-{3-[4-(dimethylamino)phenyl]propoxy}ethyl)-1H-imidazo[4,5-c]quinolin-4-ylcarbamate as a brown solid.

MS (CI) for $C_{33}H_{43}N_5O_5$ m/z 590 (MH$^+$), 490, 390, 229

Part C

Using the general method of Example 12 Part C, tert-butyl 1-(2-{3-[4-(dimethylamino)phenyl]propoxy}ethyl)-1H-imidazo[4,5-c]quinolin-4-ylcarbamate (0.783 g, 1.327 mmol) was reacted with trifluoroacetic acid (10 mL). The resulting material was triturated twice with ethyl ether to provide 0.634 g of 1-(2-{3-[4-(dimethylamino)phenyl]propoxy}ethyl)-1H-imidazo[4,5-c]quinolin-4-amine (trifluoroacetate)$_{1.5}$ as a white solid, m.p. 137–140° C.

Analysis. Calculated for $C_{23}H_{27}N_5O$ $(C_2HF_3O_2)_{1.5}$: % C, 54.83; % H, 5.22; % N, 12.30. Found: % C, 54.67; % H, 4.91; % N, 12.27

$^1$H NMR (300 MHz, DMSO-d6) δ 9.04–9.11 (bs, 2H), 8.49 (s, 1H), 8.36 (d, J=7.3 Hz, 1H), 7.83 (d, J=8.3, 1H), 7.74 (t, J=8.3 Hz, 1H), 7.56 (t, J=6.8 Hz, 1H), 6.71 (d, J=7.8 Hz, 2H), 6.60 (m, 2H), 4.90 (t, J=4.9, 2H), 3.83 (t, J=4.9, 2H), 3.27 (t, J=5.9, 2H), 2.28 (s, 6H), 2.25 (t, J=7.8, 2H), 1.54 (p, J=6.4, 6.8, 2H)

MS (CI) for $C_{23}H_{27}N_5O$ m/z 390 (MH$^+$), 229

Example 115

1-(2-{[(2E)-3-Phenylprop-2-enyl]oxy}ethyl)-1H-imidazo[4,5-c]quinolin-4-amine

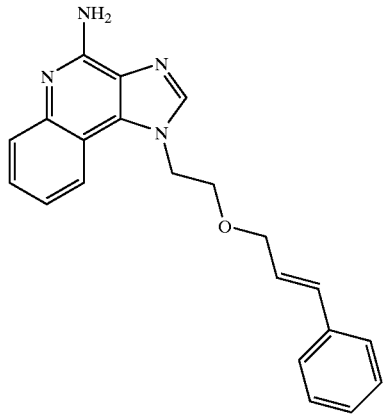

Part A

A dried round bottom flask was charged with a stir bar, sodium hydride (60% in mineral oil, 0.19 g, 4.65 mmol) and hexane (2 mL) under nitrogen. By syringe a solution of anhydrous dimethylformamide (10 mL) and 2-(1H-imidazo[4,5-c]quinolin-1-yl)ethanol (0.902 g, 4.23 mmol) was added to the flask and heated to 60° C. for 20 minutes. By syringe cinnamyl chloride (0.65 mL, 4.65 mmol) was added to solution. The reaction was judged complete at 50 minutes with ~80% conversion to desired product. The volatiles were removed under reduced pressure and the resulting oil partitioned between dichloromethane and water. The aqueous layer was extracted with dichloromethane; the organic fractions were combined, dried with anhydrous sodium sulfate, filtered and concentrated under reduced pressure. The resulting glassy solid was purified by chromatography over silica gel (95/5 dichloromethane/methanol) and dried in vacuum oven at 60° C. for 15 hours to provide 0.652 g of 1-(2-{[(2E)-3-phenylprop-2-enyl]oxy}ethyl)-1H-imidazo[4,5-c]quinoline as a glassy solid.

MS (CI) for $C_{21}H_{19}N_3O$ m/z 330 (MH$^+$), 214

Part B

Using the general method of Example 1 Part B, 1-(2-{[(2E)-3-phenylprop-2-enyl]oxy}ethyl)-1H-imidazo[4,5-c]quinoline (0.652 g, 1.98 mmol) was oxidized to provide 0.67 g of 1-(2-{[(2E)-3-phenylprop-2-enyl]oxy}ethyl)-1H-imidazo[4,5-c]quinoline-5N-oxide. The resulting brown solid was used without further purification.

Part C

A round bottom flask was charged with a stir bar, 1-(2-{[(2E)-3-phenylprop-2-enyl]oxy}ethyl)-1H-imidazo[4,5-c]quinoline-5N-oxide (0.67 g, 1.98 mmol), dichloromethane (15 mL) and aqueous ammonium hydroxide (27%, 7 mL) at ambient temperature. p-Toluenesulfonyl chloride (0.415 g, 2.18 mmol) was added in several portions as a solid and the resulting solution stirred. After 20 minutes the reaction was judged complete; the solution was partitioned between aqueous and organic and extracted with dichloromethane (3×). The organic layers were combined, extracted with 5% aqueous sodium bicarbonate (3×), washed with brine, dried over anhydrous sodium sulfate, filtered and concentrated under reduced pressure. The resulting white solid was purified by five successive recrystalizations from methanol/water to provide 0.086 g of 1-(2-{[(2E)-3-phenylprop-2-enyl]oxy}ethyl)-1H-imidazo[4,5-c]quinolin-4-amine as a white fluffy solid, m.p. 183.7–184.3° C.

Analysis. Calculated for $C_{21}H_{20}N_4O$: % C, 73.23; % H, 5.85; % N, 16.27. Found: % C, 73.11; % H, 5.81; % N, 16.10

$^1$H NMR (300 MHz, DMSO-d6) δ 8.19 (s, 1H), 8.12 (d, J=7.3 Hz, 1H), 7.62 (d, J=8.3 Hz, 1H), 7.43 (t, J=8.3 Hz, 1H), 7.19–7.31 (m, 6H), 6.61 (s, 2H), 6.33 (d, J=15.6 Hz, 1H), 6.17 (dt, J=16.0, 5.2 Hz, 1H), 4.84 (t, J=4.9, 2H), 4.07 (d, J=3.9, 2H), 3.91 (t, J=5.4, 2H)

MS (CI) for $C_{21}H_{20}N_4O$ m/z 345 (MH$^+$), 270, 229

Example 116

2-Octyl-1-{2-[(3-phenylprop-2-ynyl)oxy]ethyl}-1H-imidazo[4,5-c]quinolin-4-amine

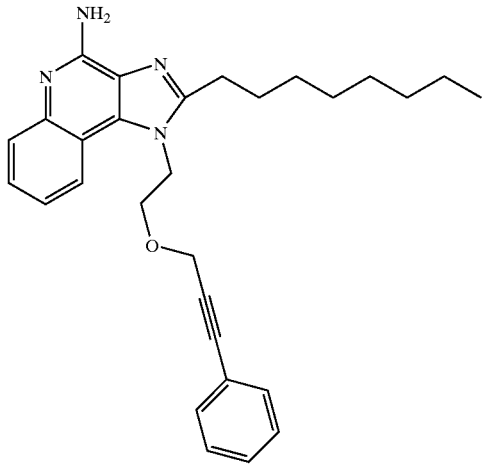

Part A

Using the general method of Example 1 Part A, 2-(2-octyl-1H-imidazo[4,5-c]quinolin-1-yl)ethanol (4.8 g, 14.75 mmol) was reacted with propargyl bromide (80% in toluene, 4.93 mL, 44.25 mmol) to provide 4.84 g of 2-octyl-1-[2-(prop-2-ynyloxy)ethyl]-1H-imidazo[4,5-c]quinoline as a brown solid.

Part B

Using the general method of Example 12 Part A, 2-octyl-1-[2-(prop-2-ynyloxy)ethyl]-1H-imidazo[4,5-c]quinoline (4.84 g, 13.32 mmol) was reacted with iodobenzene (1.7 mL, 14.65 mmol) at 40° C. After 45 minutes the reaction was judged complete. The volatiles were removed under reduced pressure and the resulting oil purified by chromatography over silica gel (98/2 (dichloromethane/methanol) to provide 4.2 g of 2-octyl-1-{2-[(3-phenylprop-2-ynyl)oxy]ethyl}-1H-imidazo[4,5-c]quinoline pale yellow solid.

MS (CI) for $C_{29}H_{33}N_3O$ m/z 440 (MH$^+$), 291

Part C

Using the general method of Example 1 Part B, 2-octyl-1-{2-[(3-phenylprop-2-ynyl)oxy]ethyl}-1H-imidazo[4,5-c]quinoline (2.2 g, 5.004 mmol) was oxidized to provide 2.28 g of 2-octyl-1-{2-[(3-phenylprop-2-ynyl)oxy]ethyl}-1H-imidazo[4,5-c]quinolin as an oil.

Part D

Using the general method of Example 115 Part C, 2-octyl-1-{2-[(3-phenylprop-2-ynyl)oxy]ethyl}-1H-imidazo[4,5-c]quinoline-5N-oxide (2.2 g, 4.83 mmol) was aminated. The resulting brown solid was purified by trituration with ethyl ether and recrystallization from 2-propanol to provide 1.23 g of 2-octyl-1-{2-[(3-phenylprop-2-ynyl)oxy]ethyl}-1H-imidazo[4,5-c]quinolin-4-amine as a white crystalline solid, m.p. 138–138.7° C.

Analysis. Calculated for $C_{29}H_{34}N_4O$: % C, 76.62; % H, 7.54; % N, 12.32. Found: % C, 76.6; % H, 7.49; % N, 12.19

$^1$H NMR (300 MHz, DMSO-d6) δ 8.07 (d, J=8.3 Hz, 1H), 7.62 (d, J=8.3 Hz, 1H), 7.41 (t, J=6.8 Hz, 1H), 7.27–7.36 (m, 3H), 7.18–7.24 (m, 3H), 6.45 (s, 2H), 4.78 (t, J=4.9 Hz, 2H), 4.34 (s, 2H), 4.00 (t, J=4.9 Hz, 2H), 2.94 (t, J=7.8 Hz, 2H), 1.83 (p, J=7.3, 7.3 Hz, 2H), 1.22–1.43 (m, 10H), 0.85 (t, J=6.8 Hz, 3H)

MS (CI) for $C_{29}H_{34}N_4O$ m/z 455 (MH$^+$), 283

Example 117

2-Octyl-1-[2-(3-phenylpropoxy)ethyl]-1H-imidazo[4,5-c]quinolin-4-amine

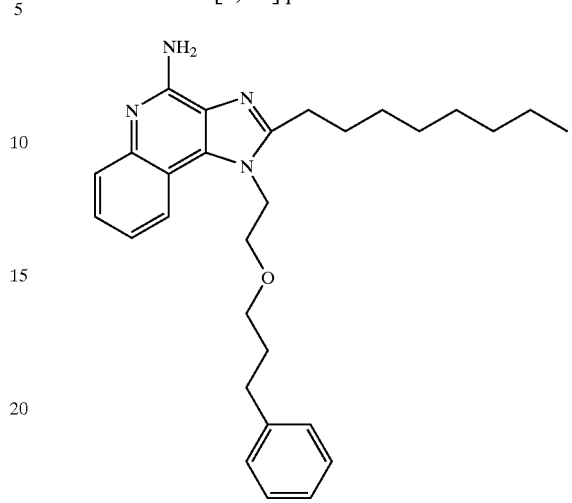

Part A

Using the general method of Example 12 Part B, 2-octyl-1-{2-[(3-phenylprop-2-ynyl)oxy]ethyl}-1H-imidazo[4,5-c]quinoline (2.0 g, 4.55 mmol) was hydrogenated to provide 1.78 g of 2-octyl-1-[2-(3-phenylpropoxy)ethyl]-1H-imidazo[4,5-c]quinoline as a white solid.

$^1$H NMR (300 MHz, DMSO-d6) δ 9.15 (s, 1H), 8.41 (d, J=9.78 Hz, 1H), 8.16 (d, J=9.8 Hz, 1H), 7.63–7.71 (m, 2H), 7.06–7.09 (m, 3H), 6.81–6.84 (m, 2H), 4.85 (t, J=4.9 Hz, 2H), 3.84 (t, J=4.9, 2H), 3.25 (t, J=5.9 Hz, 2H), 3.04 (t, J=7.8 Hz, 2H), 2.31 (t, J=8.3 Hz, 2H), 1.91 (p, J=7.3, 7.3 Hz, 2H), 1.59 (p, J=8.8, 5.8 Hz, 2H), 1.25–1.49 (m, 10H), 0.85 (t, J=7.3 Hz, 3H)

Part B

Using the general method of Example 1 Part B, 2-octyl-1-[2-(3-phenylpropoxy)ethyl]-1H-imidazo[4,5-c]quinoline (1.78 g, 4.03 mmol) was oxidized to provide 1.8 g of 2-octyl-1-[2-(3-phenylpropoxy)ethyl]-1H-imidazo[4,5-c]quinoline-5N-oxide as an oil.

Part C

Using the general method of Example 115 Part C, 2-octyl-1-[2-(3-phenylpropoxy)ethyl]-1H-imidazo[4,5-c]quinoline-5N-oxide (1.85 g 4.03 mmol) was aminated. The resulting brown solid was purified by trituration with ethyl ether and recrystallization from acetonitrile to provide 0.31 g of 2-octyl-1-[2-(3-phenylpropoxy)ethyl]-1H-imidazo[4,5-c]quinolin-4-amine as a white crystalline solid, m.p. 103.8–104.5° C.

Analysis. Calculated for $C_{29}H_{38}N_4O$: % C, 75.94; % H, 8.35; % N, 12.22. Found: % C, 75.71; % H, 8.46; % N, 12.22

$^1$H NMR (300 MHz, DMSO-d6) δ 8.06 (d, J=7.8 Hz, 1H), 7.62 (d, J=8.3 Hz, 1H), 7.41 (t, J=7.8 Hz, 1H), 7.21 (t, J=7.8 Hz, 1H), 7.05–7.15 (m, 3H), 6.90 (dd, J=5.4, 1.9, 2H), 6.45 (s, 2H), 4.73 (t, J=4.4 Hz, 2H), 3.80 (t, J=4.9 Hz, 2H), 3.24 (t, J=5.9 Hz, 2H), 2.97 (t, J=7.8 Hz, 2H), 2.39 (t, J=7.8 Hz, 2H), 1.85 (p, J=7.3, 7.8 Hz, 2H), 1.62 (p, J=6.8, 6.3 Hz, 2H), 1.24–1.44 (m, 10H), 0.84 (t, J=6.8 Hz, 3H)

MS (CI) for $C_{29}H_{38}N_4O$ m/z 459 (MH$^+$), 373, 285

Example 118

2-Methyl-1-{2-[(3-phenylprop-2-ynyl)oxy]ethyl}-1H-imidazo[4,5-c]quinolin-4-amine

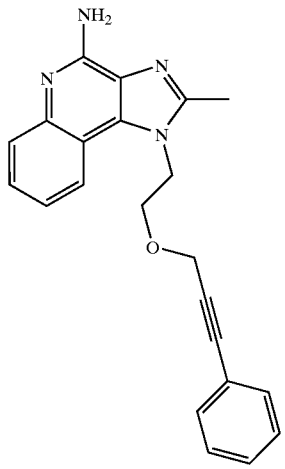

Part A

Using the general method of Example 1 Part A, 2-(2-methyl-1H-imidazo[4,5-c]quinolin-1-yl)ethanol (4.0 g, 17.6 mmol) was reacted with propargyl bromide (80% in toluene, 5.9 mL, 52.8 mmol) to provide 3.6 g of 2-methyl-1-[2-(prop-2-ynyloxy)ethyl]-1H-imidazo[4,5-c]quinoline as a dark brown oil.

MS (CI) for $C_{16}H_{15}N_3O$ m/z 266 (MH$^+$), 184

Part B

Using the general method of Example 12 Part A, 2-methyl-1-[2-(prop-2-ynyloxy)ethyl]-1H-imidazo[4,5-c]quinoline (3.6 g, 13.57 mmol) was reacted with iodobenzene (1.7 mL, 14.92 mmol) at ambient temperature. After 20 hours the reaction was judged complete. The solution was basified with 5% aqueous sodium bicarbonate and then extracted with dichloromethane (3×). The organics were combined, washed with water (3×), washed with brine, dried with anhydrous sodium sulfate, filtered and then concentrated under reduced pressure. Purification was completed by chromatography over silica gel (95/5 dichloromethane/methanol) and recrystallization from acetonitrile to provide 1.94 g of 2-methyl-1-{2-[(3-phenylprop-2-ynyl)oxy]ethyl}-1H-imidazo[4,5-c]quinoline as a light yellow solid.

MS (CI) for $C_{22}H_{19}N_3O$ m/z 342 (MH$^+$), 228

Part C

Using the general method of Example 1 Part B, 2-methyl-1-{2-[(3-phenylprop-2-ynyl)oxy]ethyl}-1H-imidazo[4,5-c]quinoline (1.0 g, 2.93 mmol) was oxidized to provide 1.3 g of 2-methyl-1-{2-[(3-phenylprop-2-ynyl)oxy]ethyl}-1H-imidazo[4,5-c]quinolin as a tan solid.

$^1$H NMR (300 MHz, DMSO-d6) δ 8.94 (s, 1H), 8.78 (d, J=8.3 Hz, 1H), 8.48 (d, J=7.8 Hz, 1H), 7.79 (m, 2H), 7.26–7.35 (m, 3H), 7.09–7.18 (m, 2H), 4.86 (t, J=5.4 Hz, 2H), 4.34 (s, 2H), 4.04 (t, J=4.9 Hz, 2H), 2.66 (s, 3H)

Part D

Using the general method of Example 115 Part C, 2-methyl-1-{2-[(3-phenylprop-2-ynyl)oxy]ethyl}-1H-imidazo[4,5-c]quinoline-5N-oxide (1.05 g, 2.93 mmol) was aminated. The resulting tan solid was purified by trituration with ethyl ether, recrystalization from toluene, chromatography over silica gel (98/2 dichloromethane/methanol) to provide 0.261 g of 2-methyl-1-{2-[(3-phenylprop-2-ynyl)oxy]ethyl}-1H-imidazo[4,5-c]quinolin-4-amine as a white powder, m.p. 142.7–143.3° C.

Analysis. Calculated for $C_{22}H_{20}N_4O$: % C, 74.14; % H, 5.66; % N, 15.72. Found: % C, 73.97; % H, 5.77; % N, 15.77

$^1$H NMR (300 MHz, DMSO-d6) δ 8.08 (d, J=8.3 Hz, 1H), 7.61 (d, J=8.3 Hz, 1H), 7.41 (t, J=8.3 Hz, 1H), 7.28–7.35 (m, 3H), 7.12–7.24 (m, 3H), 6.52 (s, 2H), 4.77 (t, J=4.9 Hz, 2H), 4.36 (s, 2H), 4.02 (t, J=4.9, 2H), 2.62 (s, 3H)

MS (CI) for $C_{22}H_{20}N_4O$ m/z 357 (MH$^+$), 243, 199

Example 119

2-Methyl-1-[2-(3-phenylpropoxy)ethyl]-1H-imidazo[4,5-c]quinolin-4-amine

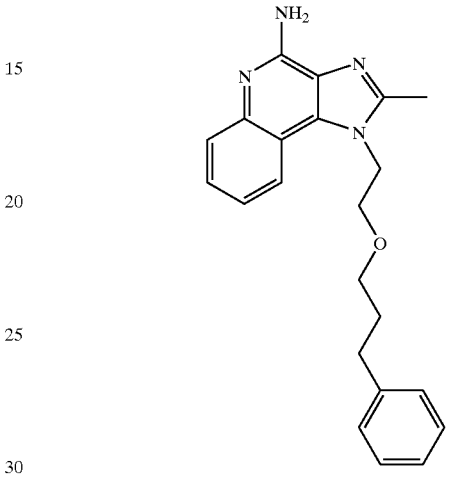

Part A

Using the general method of Example 12 Part B, 2-methyl-1-{2-[(3-phenylprop-2-ynyl)oxy]ethyl}-1H-imidazo[4,5-c]quinoline (0.9 g, 2.636 mmol) was hydrogenated to provide 0.845 g of 2-methyl-1-[2-(3-phenylpropoxy)ethyl]-1H-imidazo[4,5-c]quinoline as a white solid.

$^1$H NMR (300 MHz, DMSO-d6) δ 9.12 (s, 1H), 8.44 (d, J=7.3 Hz, 1H), 8.16 (d, J=7.8 Hz, 1H), 7.65–7.70 (m, 2H), 7.04–7.08 (m, 3H), 6.79–6.83 (m, 2H), 4.85 (t, J=4.9 Hz, 2H), 3.85 (t, J=5.4 Hz, 2H), 3.23 (t, J=6.4, 2H), 2.70 (s, 3H), 2.3 (t, J=7.8 Hz, 2H), 1.58 (p, J=6.36, 6.36 Hz, 2H)

Part B

Using the general method of Example 1 Part B, 2-methyl-1-[2-(3-phenylpropoxy)ethyl]-1H-imidazo[4,5-c]quinoline (0.845 g, 2.45 mmol) was oxidized to provide 0.88 g of 2-methyl-1-[2-(3-phenylpropoxy)ethyl]-1H-imidazo[4,5-c]quinoline-5N-oxide as a glassy solid. Material was used without further purification.

Part C

Using the general method of Example 115 Part C, 2-methyl-1-[2-(3-phenylpropoxy)ethyl]-1H-imidazo[4,5-c]quinoline-5N-oxide (0.88 g, 2.45 mmol) was aminated. The resulting brown solid was purified by trituration with ethyl ether and recrystallized from toluene to provide 0.596 g of 2-methyl-1-[2-(3-phenylpropoxy)ethyl]-1H-imidazo[4,5-c]quinolin-4-amine as a white powder, m.p. 129.7–130.7° C.

Analysis. Calculated for $C_{22}H_{24}N_4O$: % C, 73.31; % H, 6.71; % N, 15.54. Found: % C, 73.21; % H, 6.66; % N, 15.58

$^1$H NMR (300 MHz, DMSO-d6) δ 8.07 (d, J=8.3 Hz, 1H), 7.62 (d, J=7.3 Hz, 1H), 7.41 (t, J=7.3 Hz, 1H), 7.22 (t, J=8.3 Hz, 1H), 7.05–7.14 (m, 3H), 6.88 (dd, J=6.8, 2.4 Hz, 2H), 6.52 (s, 2H), 4.73 (t, J=4.9 Hz, 2H), 3.80 (t, J=4.9 Hz, 2H), 3.24 (t, J=6.4 Hz, 2H), 2.64 (s, 3H), 2.38 (t, J=8.3 Hz, 2H), 1.62 (p, J=6.8, 6.4 Hz, 2H)

MS (CI) for $C_{22}H_{24}N_4O$ m/z 361 (MH$^+$), 347, 199

Example 120

2-(Methoxyethyl)-1-{2-[(3-phenylprop-2-ynyl)oxy]ethyl}-1H-imidazo[4,5-c]quinolin-4-amine

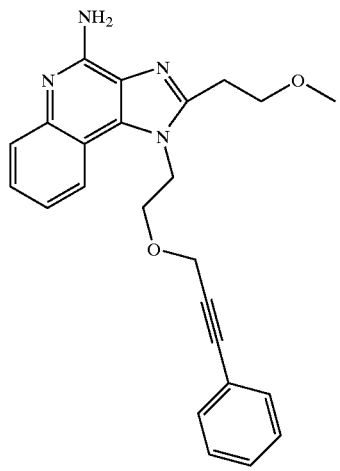

Part A

Using the general method of Example 1 Part 2-[2-(methoxyethyl)-1H-imidazo[4,5-c]quinolin-1-yl]ethanol (2.53 g, 9.33 mmol) was reacted with propargyl bromide (80% in toluene, 3.11 mL, 27.9 mmol) to provide 2.72 g of 2-(methoxyethyl)-1-[2-(prop-2-ynyloxy)ethyl]-1H-imidazo[4,5-c]quinoline as an oil.

MS (CI) for $C_{18}H_{19}N_3O_2$ m/z 310 (MH$^+$), 278, 196

Part B

Using the general method of Example 12 Part A, 2-(methoxyethyl)-1-[2-(prop-2-ynyloxy)ethyl]-1H-imidazo[4,5-c]quinoline (2.72 g, 1.79 mmol) was reacted with iodobenzene (1.1 mL, 9.67 mmol) at ambient temperature. After 45 minutes the reaction was judged complete. The volatiles were removed under reduced pressure and the resulting oil partitioned between dichloromethane and 5% aqueous sodium bicarbonate. The aqueous layer was extracted with dichloromethane. The organic fractions were combined, washed with brine, dried with anhydrous sodium sulfate, and then concentrated under reduced pressure to leave a brown solid. The solid was purified by chromatography over silica gel (95/5 (dichloromethane/methanol) and trituration with hexane to provide 2.39 g of 2-(methoxyethyl)-1-{2-[(3-phenylprop-2-ynyl)oxy]ethyl}-1H-imidazo[4,5-c]quinoline as a yellow solid.

MS (CI) for $C_{24}H_{23}N_3O_2$ m/z 386 (MH$^+$), 354, 270

Part C

Using the general method of Example 1 Part B, 2-(methoxyethyl)-1-{2-[(3-phenylprop-2-ynyl)oxy]ethyl}-1H-imidazo[4,5-c]quinoline (1.19 g, 3.097 mmol) was oxidized to provide 1.24 g of 2-(methoxyethyl)-1-{2-[(3-phenylprop-2-ynyl)oxy]ethyl}-1H-imidazo[4,5-c]quinoline-5N-oxide as an glassy solid.

Part D

Using the general method of Example 115 Part C, 2-(methoxyethyl)-1-{2-[(3-phenylprop-2-ynyl)oxy]ethyl}-1H-imidazo[4,5-c]quinoline-5N-oxide (1.243 g, 3.097 mmol) was aminated. The resulting brown oil was purified by chromatography over silica gel (98/2 dichloromethane/methanol), recrystallization from ethyl acetate and acetonitrile to provide 0.379 g of 2-(methoxyethyl)-1-{2-[(3-phenylprop-2-ynyl)oxy]ethyl}-1H-imidazo[4,5-c]quinolin-4-amine as a white solid, m.p. 134.5–135.5° C.

Analysis. Calculated for $C_{24}H_{24}N_4O_2$: % C, 71.98; % H, 6.04; % N, 13.99. Found: % C, 72.21; % H, 5.98; % N, 14.29

$^1$H NMR (300 MHz, DMSO-d6) δ 8.09 (d, J=8.3 Hz, 1H), 7.62 (d, J=8.3 Hz, 1H), 7.41 (t, J=8.3 Hz, 1H), 7.28–7.36 (m, 3H), 7.18–7.24 (m, 3H), 6.50 (s, 2H), 4.82 (t, J=4.9 Hz, 2H), 4.36 (s, 2H), 4.01 (t, J=4.9, 2H), 3.84 (t, J=6.8 Hz, 2H), 3.29 (s, 3H), 3.23 (t, J=6.8 Hz, 2H)

MS (CI) for $C_{24}H_{24}N_4O_2$ m/z 401 (MH$^+$), 255, 183

Example 121

2-(2-Methoxyethyl)-1-[2-(3-phenylpropoxy)ethyl]-1H-imidazo[4,5-c]quinolin-4-amine

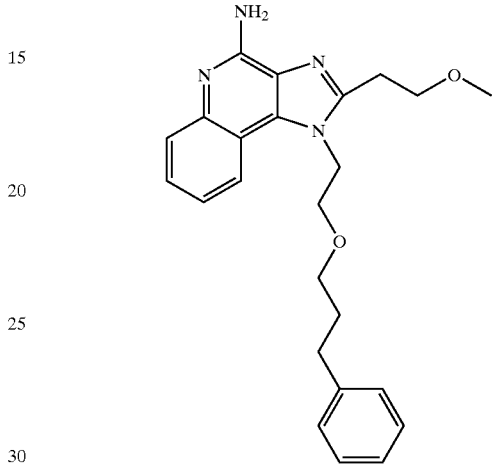

Part A

Using the general method of Example 12 Part B, 2-(2-methoxyethyl)-1-{2-[(3-phenylprop-2-ynyl)oxy]ethyl}-1H-imidazo[4,5-c]quinoline (1.2 g, 3.11 mmol), was hydrogenated to provide 1.01 g of 2-(2-methoxyethyl)-1-[2-(3-phenylpropoxy)ethyl]-1H-imidazo[4,5-c]quinoline as an oil.

MS (CI) for $C_{24}H_{27}N_3O_2$ m/z 390 (MH$^+$), 235

Part B

Using the general method of Example 1 Part B, 2-(2-methoxyethyl)-1-[2-(3-phenylpropoxy)ethyl]-1H-imidazo[4,5-c]quinoline (1.01 g, 2.60 mmol) was oxidized to provide 1.05 g of 2-(2-methoxyethyl)-1-[2-(3-phenylpropoxy)ethyl]-1H-imidazo[4,5-c]quinoline-5N-oxide as an brown oil.

Part C

Using the general method of Example 115 Part C, 2-(2-methoxyethyl)-1-[2-(3-phenylpropoxy)ethyl]-1H-imidazo[4,5-c]quinoline-5N-oxide (1.05 g, 2.601 mmol) was aminated. The resulting brown solid was purified by chromatography over silica gel (98/2 dichloromethane/methanol), recrystallization from ethyl acetate/hexane to provide 0.111 g of 2-(2-methoxyethyl)-1-[2-(3-phenylpropoxy)ethyl]-1H-imidazo[4,5-c]quinolin-4-amine as a white solid, m.p. 103.8–104.5° C.

Analysis. Calculated for $C_{24}H_{28}N_4O_2$ $(H_2O)_{0.2}$: % C, 70.63; % H, 7.01; % N, 13.73. Found: % C, 70.38; % H, 6.80; % N, 13.57

$^1$H NMR (300 MHz, DMSO-d6) δ 8.09 (d, J=7.3 Hz, 1H), 7.63 (d, J=8.3 Hz, 1H), 7.42 (t, J=6.8 Hz, 1H), 7.22 (t, J=7.8 Hz, 1H), 7.08–7.15 (m, 3H), 6.89 (d, J=5.4 Hz, 2H), 6.49 (s, 2H), 4.78 (t, J=4.9 Hz, 2H), 3.86 (t, J=6.8, 2H), 3.80 (t, J=5.4 Hz, 2H), 3.30 (s, 3H), 3.22–3.28 (m, 4H), 2.39 (t, J=8.3 Hz, 2H), 1.62 (p, J=8.3, 6.4 Hz, 2H)

MS (CI) for $C_{24}H_{28}N_4O_2$ m/z 405 (MH$^+$), 373, 235

Example 122

2-(Ethoxymethyl)-1-{2-[(3-phenylprop-2-ynyl)oxy]ethyl}-1H-imidazo[4,5-c]quinolin-4-amine

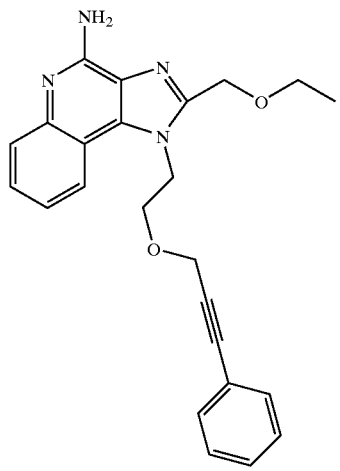

Part A

Using the general method of Example 1 Part A 2-[2-(ethoxymethyl)-1H-imidazo[4,5-c]quinolin-1-yl]ethanol (1.39 g, 5.123 mmol) was reacted with propargyl bromide (80% in toluene, 1.7 mL, 15.37 mmol) to provide 1.6 g of 2-(ethoxymethyl)-1-[2-(prop-2-ynyloxy)ethyl]-1H-imidazo[4,5-c]quinoline as an oil.

MS (CI) for $C_{18}H_{19}N_3O_2$ m/z 310 (MH$^+$), 371, 270

Part B

Using the general method of Example 12 Part A, 2-(ethoxymethyl)-1-[2-(prop-2-ynyloxy)ethyl]-1H-imidazo[4,5-c]quinoline (1.5 g, 4.13 mmol) was reacted with iodobenzene (0.51 mL, 4.54 mmol) at 40° C. After 50 minutes the reaction was judged complete. The volatiles were removed under reduced pressure and the resulting oil was partitioned between dichloromethane and 5% aqueous sodium bicarbonate. The aqueous layer was extracted with dichloromethane. The organic fractions were combined, washed with brine, dried with anhydrous sodium sulfate, and then concentrated under reduced pressure to leave a brown oil. The oil was purified by chromatography over silica gel (98/2 dichloromethane/methanol) to provide 1.25 g of 2-(ethoxymethyl)-1-{2-[(3-phenylprop-2-ynyl)oxy]ethyl}-1H-imidazo[4,5-c]quinoline as a brown glassy solid.

MS (CI) for $C_{24}H_{23}N_3O_2$ m/z 386 (MH$^+$), 342, 272

Part C

Using the general method of Example 1 Part B, 2-(ethoxymethyl)-1-{2-[(3-phenylprop-2-ynyl)oxy]ethyl}-1H-imidazo[4,5-c]quinoline (0.655 g, 1.70 mmol) was oxidized to provide 0.68 g of 2-(ethoxymethyl)-1-{2-[(3-phenylprop-2-ynyl)oxy]ethyl}-1H-imidazo[4,5-c]quinoline-5N-oxide as an oil.

Part D

Using the general method of Example 115 Part C 2-(ethoxymethyl)-1-{2-[(3-phenylprop-2-ynyl)oxy]ethyl}-1H-imidazo[4,5-c]quinoline-5N-oxide (0.682 g, 1.700 mmol) was aminated. The resulting brown solid was purified by chromatography over silica gel (98/2 dichloromethane/methanol) to provide 0.297 g of 2-(ethoxymethyl)-1-{2-[(3-phenylprop-2-ynyl)oxy]ethyl}-1H-imidazo[4,5-c]quinolin-4-amine as a white granular solid, m.p. 110.8–111.7° C.

Analysis. Calculated for $C_{24}H_{24}N_4O_2$ $(H_2O)_{0.1}$: % C, 71.66; % H, 6.06; % N, 13.93. Found: % C, 71.56; % H, 5.96; % N, 13.74

$^1$H NMR (300 MHz, DMSO-d6) δ 8.13 (d, J=7.8 Hz, 1H), 7.63 (d, J=8.3 Hz, 1H), 7.44 (t, J=6.8 Hz, 1H), 7.28–7.36 (m, 3H), 7.19–7.26 (m, 3H), 6.67 (s, 2H), 4.88 (t, J=5.4 Hz, 2H), 4.81 (s, 2H), 4.38 (s, 2H), 4.03 (t, J=5.9 Hz, 2H), 3.55 (q, J=6.8, 7.3 Hz, 2H), 1.15 (t, J=6.8 Hz, 3H)

MS (CI) for $C_{24}H_{24}N_4O_2$ m/z 401 (MH$^+$), 371, 285

Example 123

2-Butyl-1-{2-[(3-phenylprop-2-ynyl)oxy]ethyl}-1H-imidazo[4,5-c]quinolin-4-amine

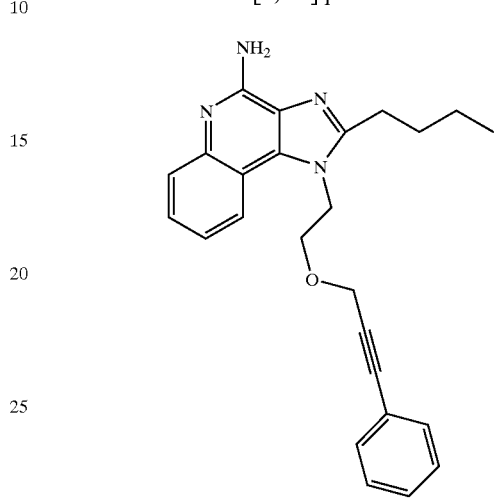

Part A

Using the general method of Example 1 Part A, 2-(2-butyl-1H-imidazo[4,5-c]quinolin-1-yl)ethanol (5.0 g, 18.56 mmol) was reacted with propargyl bromide (80% in toluene, 6.3 mL, 55.62 mmol) to provide 4.02 g of 2-butyl-1-[2-(prop-2-ynyloxy)ethyl]-1H-imidazo[4,5-c]quinoline as a tan solid.

MS (CI) for $C_{19}H_{21}N_3O$ m/z 308 (MH$^+$), 268, 220

Part B

Using the general method of Example 12 Part A, 2-butyl-1-[2-(prop-2-ynyloxy)ethyl]-1H-imidazo[4,5-c]quinoline (4.0 g, 13.08 mmol) was reacted with iodobenzene (1.6 mL, 14.38 mmol) at 90° C. After 15 minutes the reaction was judged complete. The volatiles were removed under reduced pressure and the resulting oil was purified by chromatography over silica gel (98/2 dichloromethane/methanol) and recrystallization from mixture of ethyl acetate/hexane to provide 3.1 g of 2-butyl-1-{2-[(3-phenylprop-2-ynyl)oxy]ethyl}-1H-imidazo[4,5-c]quinoline as a tan solid.

Part C

Using the general method of Example 1 Part B, 2-butyl-1-{2-[(3-phenylprop-2-ynyl)oxy]ethyl}-1H-imidazo[4,5-c]quinoline (1.0 g, 2.61 mmol) was oxidized to provide 1.0 g of 2-butyl-1-{2-[(3-phenylprop-2-ynyl)oxy]ethyl}-1H-imidazo[4,5-c]quinoline-5N-oxide as an oil.

Part D

Using the general method of Example 115 Part C, 2-butyl-1-{2-[(3-phenylprop-2-ynyl)oxy]ethyl}-1H-imidazo[4,5-c]quinoline-5N-oxide (1.04 g, 2.60 mmol) was aminated. The resulting brown solid was purified by trituration with ethyl ether, two times with chromatography over silica gel (8/2 dichloromethane/ethyl acetate, 98/2 dichloromethane/methanol) to provide 0.450 g of 2-butyl-1-{2-[(3-phenylprop-2-ynyl)oxy]ethyl}-1H-imidazo[4,5-c]quinolin-4-amine as a white powder, m.p. 133–140° C.

Analysis. Calculated for $C_{25}H_{26}N_4O$ $(H_2O)_{0.2}$: % C, 74.67; % H, 6.62; % N, 13.93. Found: % C, 74.65; % H, 6.60; % N, 14.00

¹H NMR (300 MHz, DMSO-d6) δ 8.08 (d, J=7.8 Hz, 1H), 7.61 (d, J=7.3 Hz, 1H), 7.41 (t, J=7.3 Hz, 1H), 7.29–7.36 (m, 3H), 7.17–7.24 (m, 3H), 6.45 (s, 2H), 4.78 (t, J=4.9 Hz, 2H), 4.34 (s, 2H), 4.01 (t, J=4.9, 2H), 2.95 (t, J=8.3 Hz, 2H), 1.81 (p, J=7.3, 8.3 Hz, 2H), 1.44 (sextet, J=7.3, 7.3, 7.8 Hz, 2H), 0.93 (t, J=7.3 Hz, 3H)

MS (CI) for $C_{25}H_{26}N_4O$ m/z 399 (MH⁺), 283, 267

Example 124

2-Butyl-1-[2-(3-phenylpropoxy)ethyl]-1H-imidazo[4,5-c]quinolin-4-amine

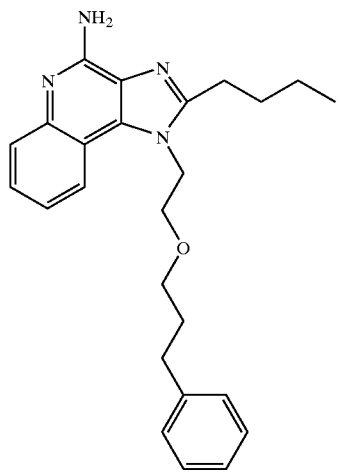

Part A

Using the general method of Example 12 Part B, 2-butyl-1-{2-[(3-phenylprop-2-ynyl)oxy]ethyl}-1H-imidazo[4,5-c]quinoline (2.4 g, 6.26 mmol) was hydrogenated to provide 1.67 g of 2-butyl-1-[2-(3-phenylpropoxy)ethyl]-1H-imidazo[4,5-c]quinoline as a white solid.

MS (CI) for $C_{25}H_{29}N_3O$ m/z 388 (MH⁺), 279

Part B

Using the general method of Example 1 Part B, 2-butyl-1-[2-(3-phenylpropoxy)ethyl]-1H-imidazo[4,5-c]quinoline (1.68 g, 4.34 mmol) was oxidized to provide 1.75 g of 2-butyl-1-[2-(3-phenylpropoxy)ethyl]-1H-imidazo[4,5-c]quinoline-5N-oxide as glassy solid.

MS (CI) for $C_{25}H_{29}N_3O_2$ m/z 404 (MH⁺), 388

Part C

Using the general method of Example 115 Part C, 2-butyl-1-[2-(3-phenylpropoxy)ethyl]-1H-imidazo[4,5-c]quinoline-5N-oxide (1.75 g, 4.34 mmol) was aminated. The resulting tan solid was purified by recrystallization from acetonitrile to provide 0.572 g of 2-butyl-1-[2-(3-phenylpropoxy)ethyl]-1H-imidazo[4,5-c]quinolin-4-amine as tan crystalline solid, m.p. 80.8–81.3° C.

Analysis. Calculated for $C_{25}H_{30}N_4O$ $(H_2O)_{0.3}$: % C, 73.61; % H, 7.56; % N, 13.73. Found: % C, 73.3; % H, 7.65; % N, 13.67

¹H NMR (300 MHz, DMSO-d6) δ 8.07 (d, J=8.3 Hz, 1H), 7.62 (d, J=8.3 Hz, 1H), 7.41 (t, J=7.3 Hz, 1H), 7.21 (t, J=7.3 Hz, 1H), 7.05–7.14 (m, 3H), 6.89 (d, J=7.3 Hz, 2H), 6.45 (s, 2H), 4.74 (t, J=4.4 Hz, 2H), 3.80 (t, J=4.9 Hz, 2H), 3.24 (t, J=5.9 Hz, 2H), 2.98 (t, J=7.8 Hz, 2H), 2.39 (t, J=7.8 Hz, 2H), 1.84 (p, J=7.3, 8.3 Hz, 2H), 1.62 (p, J=7.8, 5.9 Hz, 2H), 1.48 (sextet, J=7.3, 7.3, 7.8 Hz, 2H), 0.95 (t, J=7.3 Hz, 3H)

MS (CI) for $C_{25}H_{30}N_4O$ m/z 403 (MH⁺), 213

Example 125

1-[2-(Benzyloxy)ethyl]-2-(ethoxymethyl)-1H-imidazo[4,5-c]quinolin-4-amine

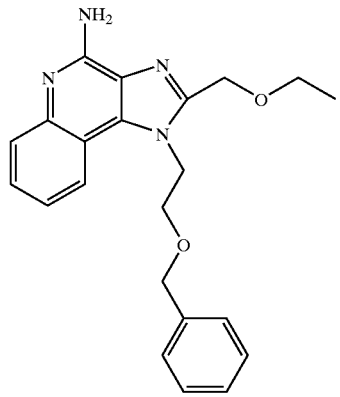

Part A

Using the general method of Example 1 Part B, 1-[2-(benzyloxy)ethyl]-2-(ethoxymethyl)-1H-imidazo[4,5-c]quinoline (0.324 g, 0.897 mmol) was oxidized to provide 0.338 g of 1-[2-(benzyloxy)ethyl]-2-(ethoxymethyl)-1H-imidazo[4,5-c]quinoline-5N-oxide as a brown oil.

Part B

Using the general method of example 115 Part C, 1-[2-(benzyloxy)ethyl]-2-(ethoxymethyl)-1H-imidazo[4,5-c]quinoline-5N-oxide (0.339 g, 0.897 mmol) was aminated. The resulting tan solid was purified by recrystallized from acetonitrile to provide 0.187 g of 1-[2-(benzyloxy)ethyl]-2-(ethoxymethyl)-1H-imidazo[4,5-c]quinolin-4-amine as a white powder, m.p. 144.5–146.0° C.

Analysis. Calculated for $C_{22}H_{24}N_4O_2$: % C, 70.19; % H, 6.43; % N, 14.88. Found: % C, 69.96; % H, 6.29; % N, 15.09

¹H NMR (300 MHz, DMSO-d6) δ 8.08 (d, J=7.8 Hz, 1H), 7.61 (d, J=8.3 Hz, 1H), 7.43 (t, J=6.8 Hz, 1H), 7.19–7.24 (m, 4H), 7.11–7.14 (m, 2H), 6.6 (s, 2H), 4.87 (t, J=5.4, 2H), 4.79 (s, 2H), 4.44 (s, 2H), 3.90 (t, J=5.4, 2H), 3.52 (q, J=6.8, 6.8 Hz, 2H), 1.13 (t, J=6.8 Hz, 3H)

MS (CI) for $C_{22}H_{24}N_4O_2$ m/z 377 (MH⁺), 331, 241

Example 126

1-[2-(Benzyloxy)ethyl]-2-butyl-1H-imidazo[4,5-c]quinolin-4-amine

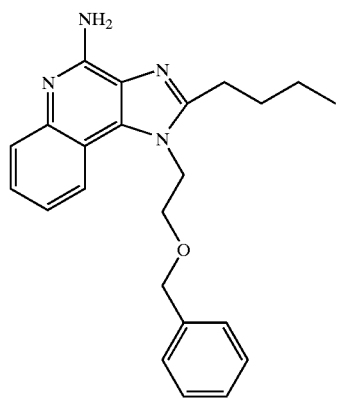

Part A

Using the general method of Example 1 Part B, 1-[2-(benzyloxy)ethyl]-2-butyl-1H-imidazo[4,5-c]quinoline (2.3 g, 6.39 mmol) was oxidized to provide 2.4 g of 1-[2-(benzyloxy)ethyl]-2-butyl-1H-imidazo[4,5-c]quinoline-5N-oxide as a brown oil.

MS (CI) for $C_{23}H_{25}N_3O_2$ m/z 376 (MH$^+$), 360, 270

Part B

Using the general method of example 1 Part C, 1-[2-(benzyloxy)ethyl]-2-butyl-1H-imidazo[4,5-c]quinoline-5N-oxide (2.4 g, 6.39 mmol) was reacted with trichloroacetyl isocyanate (1.45 g, 7.678 mmol) to provide 3.3 g of N-{1-[2-(benzyloxy)ethyl]-2-butyl-1H-imidazo[4,5-c]quinolin-4-yl}-2,2,2-trichloroacetamide as a brown oil.

Part C

Using the general method of example 1 Part D, N-{1-[2-(benzyloxy)ethyl]-2-butyl-1H-imidazo[4,5-c]quinolin-4-yl}-2,2,2-trichloroacetamide (3.3 g, 6.39 mmol) was hydrolyzed with sodium methoxide (5 mL of 25% in methanol). The resulting tan solid was purified by chromatography over silica gel (98/2 dichloromethane/methanol), recrystallized from methanol and dried under vacuum at 60° C. for 18 hours to provide 0.174 g of 1-[2-(benzyloxy)ethyl]-2-butyl-1H-imidazo[4,5-c]quinolin-4-amine as a white solid, m.p. 133–135° C.

Analysis. Calculated for $C_{23}H_{26}N_4O$: % C, 73.77; % H, 7.00; % N, 14.96. Found: % C, 73.51; % H, 7.06; % N, 14.92

$^1$H NMR (300 MHz, DMSO-d6) δ 8.03 (d, J=7.3 Hz, 1H), 7.60 (d, J=8.3 Hz, 1H), 7.39 (t, J=6.8 Hz, 1H), 7.17–7.24 (m, 4H), 7.10–7.12 (m, 2H), 6.45 (s, 2H), 4.76 (t, J=5.4 , 2H), 4.41 (s, 2H), 3.89 (t, J=4.9, 2H), 2.94 (t, J=8.3 Hz, 2H), 1.77 (p, J=7.8, 7.8 Hz, 2H), 1.40 (sextet, J=7.8, 7.3, 6.8 Hz, 2H), 0.91 (t, J=7.3 Hz, 3H)

MS (CI) for $C_{23}H_{26}N_4O$ m/z 375 (MH$^+$), 242, 183

Example 127

1-[2-(Benzyloxy)ethyl]-2-methyl-1H-imidazo[4,5-c]quinolin-4-amine

Part A

Using the general method of Example 1 Part B, 1-[2-(benzyloxy)ethyl]-2-methyl-1H-imidazo[4,5-c]quinoline (6 g, 18.9 mmol) was oxidized to provide 6.3 g of 1-[2-(benzyloxy)ethyl]-2-methyl-1H-imidazo[4,5-c]quinoline-5N-oxide as a brown solid.

Part B

Using the general method of example 1 Part C, 1-[2-(benzyloxy)ethyl]-2-methyl-1H-imidazo[4,5-c]quinoline-5N-oxide (6.3 g, 18.9 mmol) was reacted with trichloroacetyl isocyanate (4.95 g, 26.27 mmol) to provide 10.4 g of N-{1-[2-(benzyloxy)ethyl]-2-methyl-1H-imidazo[4,5-c]quinolin-4-yl}-2,2,2-trichloroacetamide as a brown solid.

Part C

Using the general method of example 1 Part D, N-{1-[2-(benzyloxy)ethyl]-2-methyl-1H-imidazo[4,5-c]quinolin-4-yl}-2,2,2-trichloroacetamide (10.46 g, 21.89 mmol) was hydrolyzed with sodium methoxide (20 mL of 25% in methanol). The resulting brown solid was purified by chromatography over silica gel (98/2 dichloromethane/methanol) and dried under vacuum at 60° C. for 18 hours to provide 1.036 g of 1-[2-(benzyloxy)ethyl]-2-methyl-1H-imidazo[4,5-c]quinolin-4-amine as a white solid, m.p. 159–160° C.

Analysis. Calculated for $C_{20}H_{20}N_4O$: % C, 72.27; % H, 6.06; % N, 16.85. Found: % C, 72.17; % H, 5.96; % N, 16.81

$^1$H NMR (300 MHz, DMSO-d6) δ 8.04 (d, J=7.3 Hz, 1H), 7.59 (d, J=8.3 Hz, 1H), 7.39 (t, J=8.3 Hz, 1H), 7.15–7.27 (m, 4H), 7.08–7.13 (m, 2H), 6.49 (s, 2H), 4.75 (t, J=5.4, 2H), 4.43 (s, 2H), 3.90 (t, J=5.4, 2H), 2.61 (s, 3H)

MS (CI) for $C_{20}H_{20}N_4O$ m/z 333 (MH$^+$), 243, 199

Example 128

1-[2-(Benzyloxy)ethyl]-2-octyl-1H-imidazo[4,5-c]quinolin-4-amine

Part A

Using the general method of Example 1 Part B, 1-[2-(benzyloxy)ethyl]-2-octyl-1H-imidazo[4,5-c]quinoline (2.4 g, 5.8 mmol) was oxidized to provide 2.5 g of 1-[2-(benzyloxy)ethyl]-2-octyl-1H-imidazo[4,5-c]quinoline-5N-oxide as a brown oil.

Part B

Using the general method of example 115 Part C, 1-[2-(benzyloxy)ethyl]-2-octyl-1H-imidazo[4,5-c]quinoline-5N-oxide (2.50 g, 5.80 mmol) was aminated. The resulting oil was purified by chromatography over silica gel (98/2 dichloromethane/methanol) and recrystallized from acetonitrile to provide 0.75 g 1-[2-(benzyloxy)ethyl]-2-octyl-1H-imidazo[4,5-c]quinolin-4-amine as a white powder, m.p. 110–111° C.

Analysis. Calculated for $C_{27}H_{34}N_4O$: % C, 75.31; % H, 7.96; % N, 13.01. Found: % C, 75.20; % H, 7.88; % N, 13.00

$^1$H NMR (300 MHz, DMSO-d6) δ 8.03 (d, J=7.8 Hz, 1H), 7.60 (d, J=8.3 Hz, 1H), 7.40 (t, J=7.3 Hz, 1H), 7.17–7.26 (m, 4H), 7.10–7.13 (m, 2H), 6.45 (s, 2H), 4.76 (t, J=4.9, 2H), 4.41 (s, 2H), 3.88 (t, J=4.9, 2H), 2.93 (t, J=7.8 Hz, 2H), 1.79 (p, J=7.3, 7.3 Hz, 2H), 1.20–1.38 (m, 10H), 0.85 (t, J=6.3 Hz, 3H)

MS (CI) for $C_{27}H_{34}N_4O$ m/z 431 (MH$^+$), 291, 214

Example 129

2-(2-Methoxyethyl)-1-(2-phenoxyethyl)-1H-imidazo[4,5-c]quinolin-4-amine

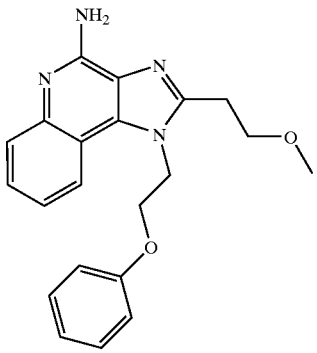

Part A

Under a nitrogen atmosphere, 2-phenoxyethylamine (17.6 ml, 0.13 mol) was added dropwise to a chilled (ice bath) solution of 4-chloro-3-nitroquinoline (21.5 g, 0.1 mol), triethylamine (21.5 ml, 0.16 mol) in dichloromethane (500 ml). The reaction was maintained at ambient temperature overnight. Water was added and the phases were separated. The organic phase was dried (MgSO$_4$), filtered, and the bulk of the solvent was removed under vacuum. Hexane was added and the solution was chilled in a refrigerator. The resulting precipitate was recovered by vacuum filtration to provide 19.1 g of 3-nitro-N-(2-phenoxyethyl)quinolin-4-amine as a yellow solid.

Part B

3-Nitro-N-(2-phenoxyethyl)quinolin-4-amine (6.0 g, 19 mmol), 5% platinum on carbon (1.5 g) and ethyl acetate (300 ml) were placed in a hydrogenation flask. The mixture was shaken overnight under a hydrogen pressure of 40 psi (2.8 Kg/cm$^2$). The reaction mixture was filtered and the catalyst was washed with ethyl acetate. The filtrate was dried (MgSO$_4$), filtered, and concentrated under vacuum to near dryness. Hexane was added and the resulting precipitate was collected by vacuum filtration to provide 4.9 g of N$^4$-(2-phenoxyethyl)quinoline-3,4-diamine as a pale yellow solid.

Part C 3-methoxypropanoyl chloride (0.86 ml, 7.9 mmol) was added dropwise over a 30 minute period to a chilled (ice bath) solution of N$^4$-(2-phenoxyethyl)quinoline-3,4-diamine (2.0 g, 7.2 mmol) in dichloromethane (100 ml). After a few hours, a precipitate formed. The solvent volume was reduced under vacuum to near dryness and hexane (100 ml) was added. Vacuum filtration provided 2.9 g of 3-methoxy-N-{4-[(2-phenoxyethyl)amino]quinolin-3-yl}propanamide as a hydrochloride salt.

Part D

The product from Part C (2.9 g) and a 7.5% solution of ammonia in methanol (200 ml) were placed in a pressure vessel. The vessel was sealed and then heated at 160° C. for 6 hours. After the mixture was cooled to ambient temperature, it was concentrated under vacuum. The residue was partitioned between dichloromethane (150 ml) and water (150 ml). The fractions were separated and the aqueous fraction was extracted with dichloromethane (100 ml). The organic fractions were combined, dried (MgSO$_4$), and filtered. The bulk of the solvent was removed under vacuum and hexane was added to yield a white precipitate. Vacuum filtration provided 1.8 g of 2-(2-methoxyethyl)-1-(2-phenoxyethyl)-1H-imidazo[4,5-c]quinoline as a white solid.

Part E

3-Chloroperoxybenzoic acid (1.5 g, 8.7 mmol, 60% by weight) was added in three portions over a period of 20 minutes to 2-(2-methoxyethyl)-1-(2-phenoxyethyl)-1H-imidazo[4,5-c]quinoline (1.8 g, 5.2 mmol) in chloroform (100 ml). The reaction mixture was maintained at ambient temperature overnight and then washed with saturated sodium bicarbonate followed by water. The organic fraction was dried (MgSO$_4$) and concentrated under vacuum to near dryness. Hexane was added and the resulting precipitate was recovered by vacuum filtration to yield 1.6 g of 2-(2-methoxyethyl)-1-(2-phenoxyethyl)-1H-imidazo[4,5-c]quinoline-5N-oxide as a light yellow powder.

Part F

Under a nitrogen atmosphere, trichloroacetyl isocyanate (0.8 ml, 6.6 mmol) was added dropwise to a solution of 2-(2-methoxyethyl)-1-(2-phenoxyethyl)-1H-imidazo[4,5-c]quinoline-5N-oxide (1.6 g, 4.4 mmol) in dichloromethane (100 ml) and the reaction was maintained at ambient temperature for 2 hours. Ammonium hydroxide (5 drops, 7% by weight in methanol) was added and the reaction was maintained at ambient temperature for an additional 2.5 days. Sodium hydroxide (10%) was added and the two phases were separated. The organic phase was concentrated and purified by flash column chromatography (silica gel, 9:1 dichloromethane/methanol). Fractions containing product were combined, concentrated in vacuo, dissolved in boiling toluene, and treated with activated charcoal. The mixture was filtered to remove the charcoal and the filtrate was cooled. The resulting precipitate was recovered by filtration and dried in a vacuum oven (80° C.) to provide 0.68 g of 2-(2-methoxyethyl)-1-(2-phenoxyethyl)-1H-imidazo[4,5-c]quinolin-4-amine as a tan powder, m.p. 171.0–174.0° C.

$^1$H NMR (300 MHz, DMSO-d6) δ 8.19 (d, J=8.1 Hz, 1H), 7.64 (d, J=8.3 Hz, 1H), 7.44 (t, J=7.5 Hz, 1H), 7.29–7.20 (m, 3H), 6.90 (t, J=7.4 Hz, 1H), 6.82 (d, J=8.2 Hz, 2H), 6.58 (s, 2H), 5.01 (t, J=5.0 Hz, 2H), 4.43 (t, J=5.0 Hz, 2H), 3.87 (t, J=6.9 Hz, 2H), 3.34 (s, 3H), 3.30 (t, J=6.9 Hz, 2H);

MS (CI) m/e 363.1820 (363.1821 calcd for C$_{21}$H$_{23}$N$_4$O$_2$, M+H);

Anal calcd for C$_{21}$H$_{22}$N$_4$O$_2$: C, 69.59; H, 6.12; N, 15.46. Found: C, 69.32; H, 6.17; N, 15.48.

Example 130

2-Isobutyl-1-(2-phenoxyethyl)-1H-imidazo[4,5-c]quinolin-4-amine

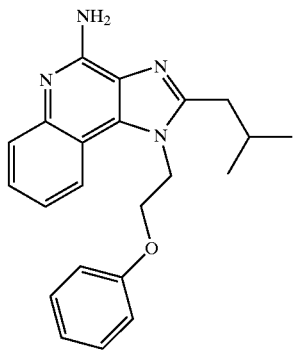

N$^4$-(2-Phenoxyethyl)quinoline-3,4-diamine (1.5 g, 5.4 mmol) and isovaleryl chloride (0.8 ml, 6.4 mmol) were combined and treated according to the general procedures of Parts C–E of Example 129. The resulting product, 2-isobutyl-1-(2-phenoxyethyl)-1H-imidazo[4,5-c]quinoline-5N-oxide (1.6 g, 4.5 mmol) was dissolved in dichloromethane (200 ml) and ammonium hydroxide (50 ml) was added. The reaction was chilled (ice bath) and p-toluenesulfonyl chloride (0.85 g, 4.5 mmol) was slowly added over a period of 20 minutes. The cooling bath was removed and the reaction was maintained at ambient temperature overnight. The phases were separated and the organic phase was sequentially washed with 1% aqueous sodium carbonate (3×), water, brine; dried ($Na_2SO_4$); and concentrated to near dryness in vacuo. Hexane was added to provide a precipitate. The solid was collected and purified by recrystallization from acetonitrile to yield 0.96 g of 2-isobutyl-1-(2-phenoxyethyl)-1H-imidazo[4,5-c]quinolin-4-amine as a tan powder, m.p. 176.6–177.8° C.

$^1$H NMR (300 MHz, DMSO-d6) δ 8.16 (d, J=8.2 Hz, 1H), 7.63 (d, J=8.3 Hz, 1H), 7.43 (t, J=7.6 Hz, 1H), 7.28–7.20 (m, 3H), 6.89 (t, J=7.3 Hz, 1H), 6.81 (d, J=8.6 Hz, 2H), 6.49 (s, 2H), 4.98 (t, J=4.8 Hz, 2H), 4.42 (t, J=4.8 Hz, 2H), 2.89 (d, J=7.2 Hz, 2H), 2.40–2.22 (m, 1H), 1.02 (d, J=6.6 Hz, 6H);

$^{13}$C NMR (75 MHz, DMSO-d6) 158.6, 153.9, 152.4, 145.5, 132.9, 130.1, 127.1, 126.9, 121.5, 120.8, 115.3, 114.7, 66.6, 44.4, 35.3, 27.1, 22.4;

MS (CI) m/e 361.2017 (361.2028 calcd for $C_{22}H_{25}N_4O$, M+H);

Anal calcd for $C_{22}H_{24}N_4O$: C, 73.31; H, 6.71; N, 15.54. Found: C, 73.33; H, 6.56; N, 15.79.

Example 131

2-Isopropyl-1-(2-phenoxyethyl)-1H-imidazo[4,5-c]quinolin-4-amine

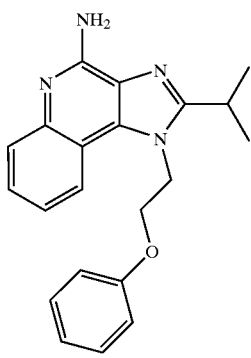

$N^4$-(2-Phenoxyethyl)quinoline-3,4-diamine (2.0 g, 7.2 mmol) and isobutyryl chloride (0.9 ml, 8.6 mmol) were combined and treated according to the general procedure described in Example 130. Recrystallization from acetonitrile provided 0.82 g of 2-isopropyl-1-(2-phenoxyethyl)-1H-imidazo[4,5-c]quinolin-4-amine as a tan solid, m.p. 229–231° C.

$^1$H NMR (300 MHz, DMSO-d6) δ 8.17 (d, J=7.5 Hz, 1H), 7.65–7.62 (dd, J=8.3, 1.1 Hz, 1H), 7.46–4.40 (dt, J=8.2, 1.1 Hz, 1H), 7.29–7.20 (m, 3H), 6.90 (t, J=7.3 Hz, 1H), 6.81 (d, J=7.8 Hz, 2H), 6.46 (s, 2H), 5.01 (t, J=4.9 Hz, 2H), 4.42 (t, J=4.9 Hz, 2H), 3.54 (septet, J=6.8 Hz, 1H), 1.41 (d, J=6.8 Hz, 6H);

$^{13}$C NMR (75 MHz, DMSO-d6) 159.3, 158.5, 152.3, 145.4, 132.6, 130.1, 126.84, 126.78, 121.5, 120.7, 115.3, 114.6, 66.5, 44.1, 25.2, 21.8;

MS (CI) m/e 347.1872 (347.1872 calcd for $C_{21}H_{23}N_4O$, M+H);

Anal calcd for $C_{21}H_{22}N_4O$: C, 72.81; H, 6.40; N, 16.17. Found: C, 72.48; H, 6.59; N, 16.50.

Example 132

2-Butyl-1-(2-phenoxyethyl)-1H-imidazo[4,5-c]quinolin-4-amine

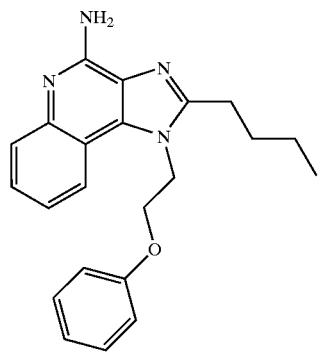

$N^4$-(2-Phenoxyethyl)quinoline-3,4-diamine (2.0 g, 7.2 mmol), xylenes (150 ml), and trimethylorthovalerate (2.5 ml, 14.3 mmol) were combined under an atmosphere of nitrogen and heated at reflux temperature for 4 days. The external heat was increased and approximately 35 ml of xylenes was removed by distillation. The reaction was slowly cooled to room temperature and a precipitate formed. The solid was recovered by vacuum filtration to yield 2.4 g of 2-butyl-1-(2-phenoxyethyl)-1H-imidazo[4,5-c]quinoline as a light tan crystalline solid.

2-Butyl-1-(2-phenoxyethyl)-1H-imidazo[4,5-c]quinoline was treated according to the general procedures described in Parts E and F of Example 129. A final recrystallization from acetonitrile provided 0.93 g of 2-butyl-1-(2-phenoxyethyl)-1H-imidazo[4,5-c]quinolin-4-amine as white needles, m.p. 168.3–169.5° C.

$^1$H NMR (300 MHz, DMSO-d6) δ 8.16 (d, J=8.1 Hz, 1H), 7.63 (d, J=8.3 Hz, 1H), 7.43 (t, J=7.6 Hz, 1H), 7.28–7.20 (m, 3H), 6.90 (t, J=7.4 Hz, 1H), 6.82 (d, J=8.5 Hz, 2H), 6.47 (s, 2H), 4.97 (t, J=4.8 Hz, 2H), 4.43 (t, J=4.8 Hz, 2H), 3.00 (t, J=7.7 Hz, 2H), 1.86 (m, 2H), 1.47 (m, 2H), 0.96 (t, J=7.3 Hz, 3H);

$^{13}$C NMR (75 MHz, DMSO-d6) 158.5, 154.6, 152.3, 145.6, 132.9, 130.1, 126.8, 121.5, 120.7, 115.2, 114.6, 66.7, 44.4, 29.3, 26.2, 21.9, 13.6;

MS (CI) m/e 361.2032 (361.2028 calcd for $C_{22}H_{25}N_4O$, M+H);

Anal calcd for $C_{22}H_{24}N_4O$: C, 73.31; H, 6.71; N, 15.54. Found: C, 73.15; H, 6.69; N, 15.57.

Example 133

1-(2-Phenoxyethyl)-2-(phenoxymethyl)-1H-imidazo[4,5-c]quinolin-4-amine

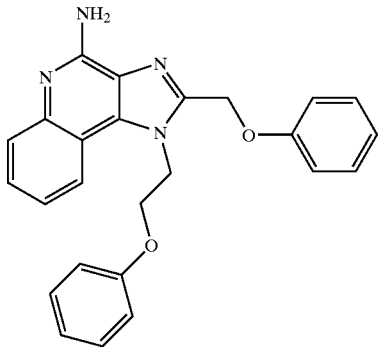

According to the general procedure described in Part C of Example 129, phenoxyacetyl chloride (1.2 ml, 8.6 mmol) was reacted with $N^4$-(2-phenoxyethyl)quinoline-3,4-diamine (2.0 g, 7.2 mmol). The product of this reaction was treated according to the general procedures described in Parts D–F of Example 129. Recrystallization from acetonitrile provided 0.65 g of the final product, 1-(2-phenoxyethyl)-2-(phenoxymethyl)-1H-imidazo[4,5-c]quinolin-4-amine, as a tan powder, m.p. 168.5–170.0° C.

$^1$H NMR (300 MHz, DMSO-d6) δ 8.25 (d, J=7.9 Hz, 1H), 7.64 (dd, J=8.3, 1.0 Hz, 1H), 7.47 (m, 1H), 7.38–7.14 (m, 7H), 7.01 (t, J=7.3 Hz, 1H), 6.89 (t, J=7.3 Hz, 1H), 6.81 (d, J=7.8 Hz, 2H), 6.69 (s, 2H), 5.53 (s, 2H), 5.29 (t, J=5.0 Hz, 2H), 4.48 (t, J=5.0 Hz, 2H);

$^{13}$C NMR (75 MHz, DMSO-d6) 158.5, 152.7, 149.2, 146.1, 134.1, 130.2, 130.1, 127.6, 127.0, 126.9, 122.0, 121.6, 121.5, 121.4, 115.3, 115.1, 114.7, 66.6, 62.7, 45.0;

MS (CI) m/e 411.1813 (411.1821calcd for $C_{25}H_{23}N_4O_2$, M+H);

Anal calcd for $C_{25}H_{22}N_4O_2$: C, 73.15; H, 5.40; N, 13.65. Found: C, 73.36; H, 5.30; N, 13.66.

Example 134

2-(4-Methoxybenzyl)-1-(2-phenoxyethyl)-1H-imidazo[4,5-c]quinolin-4-amine

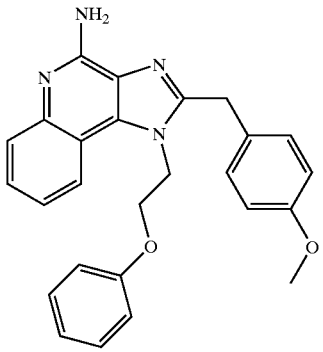

According to the general procedure described in Part C of Example 129, 4-methoxyphenylacetyl chloride (1.2 ml, 7.9 mmol) was reacted with $N^4$-(2-phenoxyethyl)quinoline-3,4-diamine (2.0 g, 7.2 mmol). The product of this reaction was treated according to the general procedures described in Parts D-F of Example 129. Recrystallization from acetonitrile provided 1.1 g of the final product, 2-(4-methoxybenzyl)-1-(2-phenoxyethyl)-1H-imidazo[4,5-c]quinolin-4-amine, as a tan solid, m.p. 201.0–203.6° C.

$^1$H NMR (300 MHz, DMSO-d6) δ 8.15 (d, J=8.1 Hz, 1H), 7.63 (d, J=8.3 Hz, 1H), 7.43 (t, J=7.6 Hz, 1H), 7.26–7.18 (m, 5H), 6.93–6.87 (m, 3H), 6.74 (d, J=8.2 Hz, 2H), 6.58 (s, 2H), 4.89 (t, J=5.1 Hz, 2H), 4.40 (s, 2H), 4.24 (t, J=5.1 Hz, 2H), 3.70 (s, 3H);

MS (CI) m/e 425.1948 (425.1978 calcd for $C_{26}H_{25}N_4O_2$, M+H);

Anal calcd for $C_{26}H_{24}N_4O_2$: C, 73.57; H, 5.70; N, 13.20. Found: C, 73.25; H, 5.93; N, 13.06.

Example 135

2-Cyclopentyl-1-(2-phenoxyethyl)-1H-imidazo[4,5-c]quinolin-4-amine

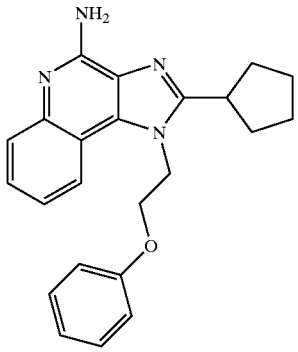

$N^4$-(2-phenoxyethyl)quinoline-3,4-diamine (2.0 g, 7.2 mmol) and cyclopentanecarbonyl chloride (1.1 ml, 8.6 mmol) were combined and treated according to the general procedure described in Example 130. Recrystallization from acetonitrile provided 1.4 g of 2-cyclopentyl-1-(2-phenoxyethyl)-1H-imidazo[4,5-c]quinolin-4-amine as a tan solid, m.p. 216.0–217.9° C.

$^1$H NMR (300 MHz, DMSO-d6) δ 8.17 (d, J=8.1 Hz, 1H), 7.63 (d, J=8.2 Hz, 1H), 7.43 (t, J=7.6 Hz, 1H), 7.28–7.20 (m, 3H), 6.90 (t, J=7.3 Hz, 1H), 6.81 (d, J=8.5 Hz, 2H), 6.46 (s, 2H), 5.02 (t, J=4.9 Hz, 2H), 4.42 (t, J=4.9 Hz, 2H), 3.60 (pentet, J=8.2 Hz, 1H), 2.18–1.67 (m, 8H);

$^{13}$C NMR (75 MHz, DMSO-d6) 158.5, 158.3, 152.9, 144.6, 133.0, 130.1, 126.8, 121.5, 120.8, 115.3, 114.7, 66.5, 44.2, 36.1, 32.3, 25.3;

MS (CI) m/e 373.2030 (373.2028 calcd for $C_{23}H_{25}N_4O$, M+H);

Anal calcd for $C_{23}H_{24}N_4O$: C, 74.17; H, 6.49; N, 15.04. Found: C, 74.18; H, 6.59; N, 15.08.

Example 136

2-[(2-Methoxyethoxy)methyl]-1-(2-phenoxyethyl)-1H-imidazo[4,5-c]quinolin-4-amine

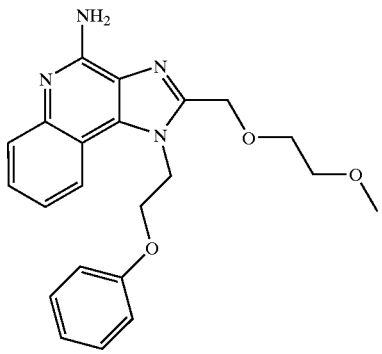

$N^4$-(2-phenoxyethyl)quinoline-3,4-diamine (2.0 g, 7.2 mmol) and 2-(2-methoxyethoxy)acetyl chloride (1.3 g, 8.6 mmol) were combined and treated according to the general procedure described in Example 130. Recrystallization from methanol provided 1.6 g of 2-[(2-methoxyethoxy)methyl]-1-(2-phenoxyethyl)-1H-imidazo[4,5-c]quinolin-4-amine as white needles, m.p. 170.0–171.5° C.

$^1$H NMR (300 MHz, CDCl$_3$) δ 8.06 (dd, J=8.3, 1.0 Hz, 1H), 7.82 (dd, J=8.4, 1.0 Hz, 1H), 7.55–7.50 (m, 1H), 7.35–7.29 (m, 1H), 7.26–7.18 (m, 2H), 6.92 (t, J=7.4 Hz, 1H), 6.79 (dd, J=8.7, 0.9 Hz, 2H), 5.57 (s, 2H), 5.07 (t, J=5.9 Hz, 2H), 5.00 (s, 2H), 4.47 (t, J=5.9 Hz, 2H), 3.71 (m, 2H), 3.55 (m, 2H), 3.31 (s, 3H);

$^{13}$C NMR (75 MHz, CDCl$_3$) 158.9, 152.3, 150.3, 146.2, 135.2, 130.3, 128.3, 128.2, 127.6, 123.1, 122.2, 120.6, 116.1, 115.1, 72.1, 70.2, 66.6, 66.3, 59.3, 45.6;

MS (CI) m/e 393.1912 (393.1927 calcd for $C_{22}H_{25}N_4O_3$, M+H);

Anal calcd for $C_{22}H_{24}N_4O_3$: C, 67.33; H, 6.16; N, 14.27. Found: C, 67.62; H, 6.24; N, 14.37.

Example 137

2-(Cyclopropylmethyl)-1-(2-phenoxyethyl)-1H-imidazo[4,5-c]quinolin-4-amine

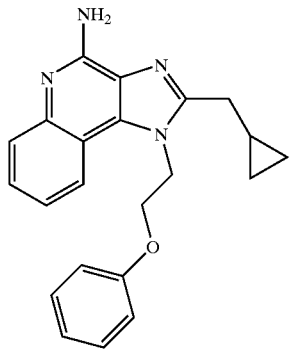

$N^4$-(2-phenoxyethyl)quinoline-3,4-diamine (1.7 g, 6.1 mmol) and cyclopropylacetyl chloride (0.86 ml, 7.3 mmol) were combined and treated according to the general procedure described in Example 130. Recrystallization from methanol provided 0.86 g of 2-(cyclopropylmethyl)-1-(2-phenoxyethyl)-1H-imidazo[4,5-c]quinolin-4-amine as a white solid, m.p. 191.7–192.6° C.

$^1$H NMR (300 MHz, DMSO-d6) δ 8.17 (d, J=7.5 Hz, 1H), 7.63 (dd, J=8.3, 1.1 Hz, 1H), 7.46–7.41 (m, 1H), 7.28–7.19 (m, 3H), 6.89 (t, J=7.3 Hz, 1H), 6.79 (d, J=7.8 Hz, 2H), 6.49 (s, 2H), 4.98 (t, J=5.0 Hz, 2H), 4.42 (t, J=5.0 Hz, 2H), 2.99 (d, J=6.7 Hz, 2H), 1.40–1.26 (m, 1H), 0.55 (m, 2H), 0.32 (m, 2H);

$^{13}$C NMR(75 MHz, DMSO-d6) 158.6, 154.1, 152.4, 145.5, 133.1, 130.1, 127.0, 126.9, 121.5, 120.8, 115.2, 114.7, 72.1, 66.6, 44.5, 31.1, 9.0, 4.6;

Anal calcd for $C_{22}H_{22}N_4O*0.1H_2O$: C, 73.35; H, 6.21; N, 15.55. Found: C, 73.23; H, 6.31; N, 15.57.

Example 138

2-(2-Cyclopentylethyl)-1-(2-phenoxyethyl)-1H-imidazo[4,5-c]quinolin-4-amine

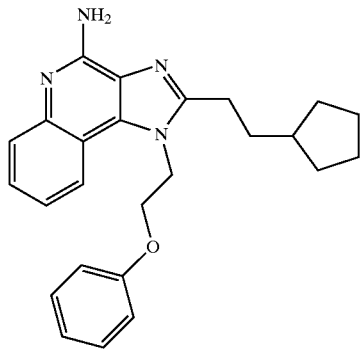

According to the general procedure described in Part C of Example 129, 3-cyclopentylpropionyl chloride (1.3 ml, 8.6 mmol) was reacted with $N^4$-(2-phenoxyethyl)quinoline-3,4-diamine (2.0 g, 7.2 mmol). The product of this reaction was treated according to the general procedures described in Parts D-F of Example 129. Recrystallization from acetonitrile provided 0.44 g of the final product, 2-(2-cyclopentylethyl)-1-(2-phenoxyethyl)-1H-imidazo[4,5-c]quinolin-4-amine, as a white powder, m.p. 165.0° C.

$^1$H NMR (300 MHz, DMSO-d6) δ 8.17 (d, J=8.0 Hz, 1H), 7.64 (dd, J=8.3, 0.80 Hz, 1H), 7.44 (t, J=7.3 Hz, 1H), 7.29–7.20 (m, 3H), 6.90 (t, J=7.3 Hz, 1H), 6.81 (d, J=7.9 Hz, 2H), 6.60 (s, 2H), 4.97 (t, J=4.6 Hz, 2H), 4.44 (t, J=4.6 Hz, 2H), 3.00 (t, J=7.6 Hz, 2H), 1.91–1.77 (m, 5H), 1.64–1.48 (m, 4H), 1.20–1.14 (m, 2H);

$^{13}$C NMR (75 MHz, CDCl$_3$) 158.2, 155.0, 151.5, 144.7, 133.6, 129.9, 127.5, 127.4, 127.0, 122.6, 121.9, 119.5, 115.5, 114.5, 66.0, 45.7, 39.8, 33.9, 32.3, 26.4, 24.9;

MS (CI) m/e 401.2336 (401.2341 calcd for $C_{25}H_{29}N_4O$, M+H);

Anal calcd for $C_{25}H_{28}N_4O$: C, 74.97; H, 7.05; N, 13.99. Found: C, 74.67; H, 7.11; N, 13.97.

Example 139

1-(2-Phenoxyethyl)-2-tetrahydrofuran-3-yl-1H-imidazo[4,5-c]quinolin-4-amine

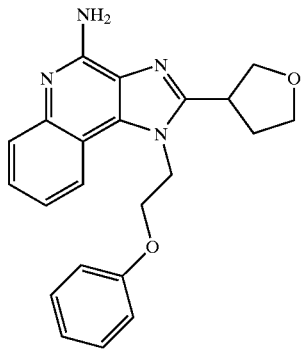

$N^4$-(2-phenoxyethyl)quinoline-3,4-diamine (1.6 g, 5.7 mmol) and tetrahydrofuran-3-carbonyl chloride (0.98 ml, 7.3 mmol) were combined and treated according to the general procedure described in Example 130. Recrystallization from acetonitrile provided 0.3 g of 1-(2-phenoxyethyl)-2-tetrahydrofuran-3-yl-1H-imidazo[4,5-c]quinolin-4-amine as a tan solid, m.p. 235.9–236.3° C.

$^1$H NMR (300 MHz, DMSO-d6) δ 8.18 (d, J=7.8 Hz, 1H), 7.63 (dd, J=8.3, 1.0 Hz, 1H), 7.44 (dd, J=7.6, 1.0 Hz, 1H), 7.29–7.20 (m, 3H), 6.90 (t, J=7.3 Hz, 1H), 6.81 (d, J=7.9 Hz, 2H), 6.49 (s, 2H), 5.05 (t, J=4.9 Hz, 2H), 4.42 (t, J=4.9 Hz, 2H), 4.24 (m, 1H), 4.04–3.98 (m, 3H), 3.92–3.87 (m, 1H), 2.50–2.30 (m, 2H);

$^{13}$C NMR(75 MHz, DMSO-d6) 158.6, 155.2, 152.4, 145.5, 133.2, 130.1, 127.0, 126.9, 121.6, 120.3, 115.2, 114.7, 72.1, 68.0, 66.5, 44.4, 36.0, 32.4;

MS (CI) m/e 375.1808 (375.1821 calcd for $C_{22}H_{23}N_4O_2$, M+H);

Anal calcd for $C_{22}H_{22}N_4O_2$*0.25$H_2O$: C, 69.73; H, 5.98; N, 14.78. Found: C, 69.90; H, 5.91; N, 14.90.

Example 140

1-(2-Phenoxyethyl)-2-phenyl-1H-imidazo[4,5-c]quinolin-4-amine

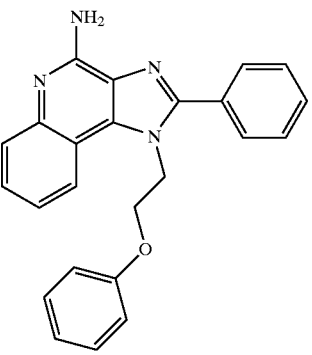

According to the general procedure described in Part C of Example 129, benzoyl chloride (1.0 ml, 8.5 mmol) was reacted with $N^4$-(2-phenoxyethyl)quinoline-3,4-diamine (2.0 g, 7.2 mmol). The product of this reaction was treated according to the general procedures described in Parts D-F of Example 129. Recrystallization from methanol provided 0.74 g of the final product, 1-(2-phenoxyethyl)-2-phenyl-1H-imidazo[4,5-c]quinolin-4-amine, as a tan solid, m.p. 182.5–184.6° C.

$^1$H NMR (300 MHz, DMSO-d6) δ 8.21 (d, J=7.9 Hz, 1H), 7.83–7.79 (m, 2H), 7.68–7.58 (m, 4H), 7.48 (t, J=7.3 Hz, 1H), 7.29 (t, J=7.3 Hz, 1H), 7.16 (m, 2H), 6.85 (t, J=7.3 Hz, 1H), 6.68 (m, 4H), 5.02 (t, J=5.1 Hz, 2H), 4.33 (t J=5.1 Hz, 2H);

$^{13}$C NMR (75 MHz, DMSO-d6) 158.2, 153.6, 152.9, 146.0, 133.6, 131.1, 130.8, 130.3, 130.1, 129.3, 127.9, 127.5, 127.1, 121.9, 121.6, 121.2, 115.4, 114.7, 66.1, 45.6;

MS (CI) m/e 381.1703 (381.1715 calcd for $C_{24}H_{21}N_4O$, M+H);

Anal calcd for $C_{24}H_{20}N_4O$*0.25$H_2O$: C, 74.88; H, 5.37; N, 14.55. Found: C, 74.42; H, 5.10; N, 14.48.

Example 141

4-{[2-(4-Amino-1H-imidazo[4,5-c]quinolin-1-yl)butoxy]methyl}benzonitrile

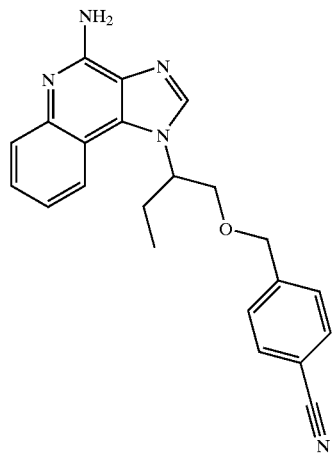

Part A 2-(1H-imidazo[4,5-c]quinolin-1-yl)-1-butanol (3.0 g, 12.4 mmol) was added to a stirring mixture of α-bromo-p-tolunitrile (3.0 g, 15.3 mmol), sodium hydroxide (40 ml, 50%), dichloromethane (40 ml), and benzyltrimethylammonium chloride (0.02 g, 0.11 mmol). The reaction was maintained for 72 hours and then diluted with dichloromethane (100 ml) and water (100 ml). The phases were separated and the aqueous phase was extracted with additional dichloromethane (100 ml). The organic fractions were combined, washed with water, dried (MgSO$_4$), filtered, and concentrated in vacuo. The residue was purified by flash column chromatography (silica gel, 9/1 dichloromethane/methanol, R$_f$0.48) to provide 2.66 g of 4-{[2-(1H-imidazo[4,5-c]quinolin-1-yl)butoxy]methyl}benzonitrile.

Part B

3-Chloroperoxybenzoic acid (2.2 g, 7.5 mmol, 60% by weight) was slowly added to a solution of 4-{[2-(1H-imidazo[4,5-c]quinolin-1-yl)butoxy]methyl}benzonitrile (2.6 g, 7.3 mmol) in chloroform (70 ml). The reaction was maintained for 2 hours and then sequentially washed with saturated sodium bicarbonate (200 ml), water (2×100 ml); dried (MgSO$_4$); filtered; and concentrated to provide 2.7 g of the 5N-oxide product.

Part C p-Toluenesulfonyl chloride (1.43 g, 7.5 mmol) was slowly added over a 20 minute period to a chilled (0° C.) mixture of the product from Part B (2.7 g, 7.3 mmol), concentrated ammonium hydroxide (10 ml) and dichloromethane (20 ml). Monitoring by thin layer chromatography (9:1 dichloromethane/methanol) indicated that the reaction was complete within minutes. The reaction was warmed to ambient temperature and the phases were separated. The organic phase was sequentially washed with sodium carbonate (3×), water, and brine; dried ($Na_2SO_4$); and concentrated in vacuo. Purification of the resulting brown oil by flash column chromatography (silica gel, 92/8 dichloromethane/methanol) followed by multiple recrystallizations from ethyl acetate/hexane yielded 0.45 g of 4-{[2-(4-amino-1H-imidazo[4,5-c]quinolin-1-yl)butoxy]methyl}benzonitrile as a tan powder, m.p. 160.0–161.0° C.

$^1$H NMR (300 MHz, DMSO-d6) δ 8.41 (s, 1H), 8.20 (d, J=7.3 Hz, 1H), 7.67 (m, 3H), 7.44 (t, J=7.3 Hz, 1H), 7.31–7.21 (m, 3H), 6.72 (s, 2H), 5.26 (broad s, 1H), 4.54 (s, 2H), 4.02–3.91 (m, 2H), 2.07 (m, 2H), 0.87 (t, J=7.3 Hz, 3H);
$^{13}$C NMR (125 MHz, DMSO-d6) 152.2, 145.2, 143.8, 140.1, 132.4, 132.0, 127.5, 126.6, 126.4, 121.0, 120.5, 118.7, 115.0, 110.0;
MS (EI) m/e 371.1754 (371.1746 calcd for $C_{22}H_{21}N_5O$);
Anal calcd for $C_{22}H_{21}N_5O$: C, 71.14; H, 5.70; N, 18.85. Found: C, 70.78; H, 5.65; N, 18.51.

Example 142

4-({[(2R)-2-(4-Amino-1H-imidazo[4,5-c]quinolin-1-yl)butyl]oxy}methyl)benzonitrile

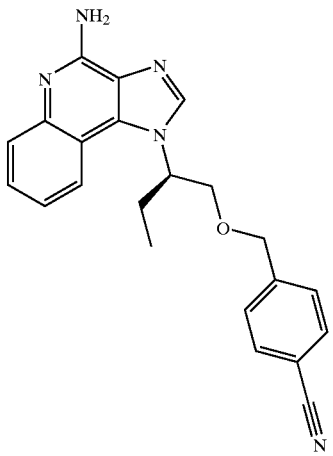

(2R)-2-(1H-imidazo[4,5-c]quinolin-1-yl)butan-1-ol (1.36 g, 5.3 mmol) was reacted according to the general procedures described in Parts A and B of Example 141 to provide 1.60 g of the 5N-oxide product.

Trichloroacetyl isocyanate (0.77 ml, 6.5 mmol) was added dropwise to a solution of the 5N-oxide (1.60 g) and dichloromethane (25 ml). The reaction was maintained overnight and then concentrated in vacuo. The resulting red oil was dissolved in methanol (25 ml) and sodium methoxide (4.0 ml, 21% in methanol) was added dropwise. The reaction was maintained for 2.5 days. The solvent was removed in vacuo and the crude product was purified by flash column chromatography (silica gel, 92/8 dichloromethane/methanol) followed by recrystallization from methyl acetate to yield 4-({[(2R)-2-(4-amino-1H-imidazo[4,5-c]quinolin-1-yl)butyl]oxy}methyl)benzonitrile as a white solid. The enantiomeric excess (ee) of the final product was determined to be greater than 99% based on liquid chromatography (column: CHIRALCEL® OD-RH; eluent: 90/10/0.2 pentane/methanol/triethylamine; flow rate 2 ml/min, $R_t$ 7.8 minutes).

$^1$H NMR (500 MHz, DMSO-d6) δ 8.39 (s, 1H), 8.20 (d, J=7.8 Hz, 1H), 7.69 (d, J=8.1 Hz, 2H), 7.63 (dd, J=8.3, 1.1 Hz, 1H), 7.45–7.42 (m, 1H), 7.31 (d, J=8.1 Hz, 2H), 7.23 (m, 1H), 6.58 (s, 2H), 5.27 (broad s, 1H), 4.57 (s, 2H), 4.03 (dd, J=10.3, 6.8 Hz, 1H), 3.93 (dd, J=10.3, 3.9 Hz, 1H), 2.09 (m, 2H), 0.89 (t, J=7.3 Hz, 3H);

Anal calcd for $C_{22}H_{21}N_5O$: C, 71.14; H, 5.70; N, 18.85. Found: C, 71.00; H, 5.66; N, 18.64.

Example 143

4-({[(2S)-2-(4-Amino-1H-imidazo[4,5-c]quinolin-1-yl)butyl]oxy}methyl)benzonitrile

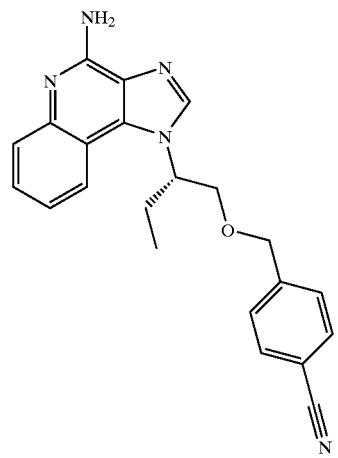

(2S)-2-(1H-imidazo[4,5-c]quinolin-1-yl)butan-1-ol (1.3 g) was reacted according to the general procedure described in Example 142. Recrystallization of the final product from ethyl acetate/hexanes provided 0.2 g of 4-({[(2S)-2-(4-amino-1H-imidazo[4,5-c]quinolin-1-yl)butyl]oxy}methyl) benzonitrile as a white solid. The enantiomeric excess (ee) of the final product was determined to be greater than 99% based on liquid chromatography (column: CHIRALCEL® OD-RH; eluent: 90/10/0.2 pentane/methanol/triethylamine; flow rate 2 m/min, $R_t$ 8.7 minutes).

$^1$H NMR (500 MHz, DMSO-d6) δ 8.40 (s, 1H), 8.20 (d, J=8.0 Hz, 1H), 7.70 (d, J=8.2 Hz, 2H), 7.63 (dd, J=8.3, 1.1 Hz, 1H), 7.46–7.41 (m, 1H), 7.31 (d, J=8.2 Hz, 2H), 7.23 (m, 1H), 6.62 (s, 2H), 5.27 (broad s, 1H), 4.57 (s, 2H), 4.04 (dd, J=10.3, 6.7 Hz, 1H), 3.93 (dd, J=10.3, 3.9 Hz, 1H), 2.10 (m, 2H), 0.88 (t, J=7.3 Hz, 3H);

Anal calcd for $C_{22}H_{21}N_5O$: C, 71.14; H, 5.70; N, 18.85. Found: C, 71.10; H, 5.98; N, 18.96.

Example 144

2-(2-Methoxyethyl)-1-[2-(prop-2-ynyloxy)ethyl]-1H-imidazo[4,5-c]quinolin-4-amine

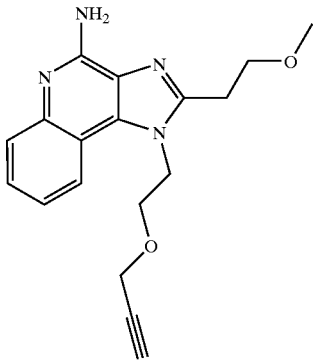

Part A

Propargyl bromide (10.0 ml, 89.8 mmol, 80% in toluene) and benzyltrimethylammonium chloride (0.60 g, 3.2 mmol) were dissolved in dichloromethane (130 ml). The solution was treated with sodium hydroxide (130 ml, 50% w/w in water). 2-[2-(2-Methoxyethyl)-1H-imidazo[4,5-c]quinolin-1-yl]ethanol (20.0 g, 73.7 mmol) was added and the mixture was vigorously stirred for 18 hours. Thin layer chromatography (9/1 chloroform/methanol) indicated complete conversion. The mixture was diluted with water (200 ml) and the phases were separated. The aqueous fraction was extracted with additional dichloromethane (3×150 ml). The combined organic fractions were washed with brine (100 ml), dried ($Na_2SO_4$), filtered and concentrated to yield 22.7 g of 2-(2-methoxyethyl)-1-[2-(prop-2-ynyloxy)ethyl]-1H-imidazo[4,5-c]quinoline as an orange solid.

$^1$H NMR (300 MHz, DMSO-d6) δ 9.15 (s, 1H), 8.40 (m, 1H), 8.15 (m, 1H), 7.73–7.64 (m, 2H), 4.89 (t, J=5.3 Hz, 2H), 4.10 (d, J=2.4 Hz, 2H), 3.95 (t, J=5.1 Hz, 2H), 3.98 (t, J=6.9 Hz, 2H), 3.36 (t, J=2.4 Hz, 1H), 3.32 (s, 3H), 3.27 (t, J=6.9 Hz, 2H).

Part B 2-(2-Methoxyethyl)-1-[2-(prop-2-ynyloxy)ethyl]-1H-imidazo[4,5-c]quinoline (22.7 g, 73.4 mmol) was dissolved in chloroform (300 ml) and chilled in an ice water bath. 3-Chloroperoxybenzoic acid (17.0 g, 127.9 mmol, 77% max) was added in small portions over 30 minutes. Analysis by thin layer chromatography (9/1 chloroform/methanol) at 30 minutes indicated that there was still starting material present. Additional 3-chloroperoxybenzoic acid (7.00 g, 52.7 mmol, 77% max) was added. After 2 hours, the reaction was warmed to ambient temperature and quenched by the addition of saturated sodium bicarbonate (100 ml). The aqueous and organic fractions were separated and the aqueous fraction was extracted with additional chloroform (2×50 ml). The combined organic fractions were washed with water (100 ml), brine (100 ml); dried ($Na_2SO_4$); filtered; and concentrated in vacuo to provide a dark orange solid. $^1$H NMR indicated less than 5% 3-chlorobenzoic acid in the crude product. The material was used without further purification.

$^1$H NMR (300 MHz, DMSO-d6) δ 8.56 (s, 1H), 8.33 (d, J=7.7 Hz, 1H), 7.99 (d, J=7.3 Hz, 1H), 7.38–7.30 (m, 2H), 4.40 (t, J=4.8 Hz, 2H), 3.63 (d, J=2.1 Hz, 2H), 3.47 (t, J=4.9 Hz, 2H), 3.40 (t, J=6.9 Hz, 2H), 2.88 (t, J=2.0 Hz, 1H), 2.84 (s, 3H), 2.78 (t, J=6.3 Hz, 2H).

Part C

Under an atmosphere of nitrogen, 2-(2-methoxyethyl)-1-[2-(prop-2-ynyloxy)ethyl]-1H-imidazo[4,5-c]quinoline-5N-oxide (1.57 g, 4.83 mmol) was dissolved in dichloromethane (25 ml). Trichloroacetyl isocyanate (0.80 ml, 6.71 mmol) was added dropwise via syringe. The reaction was stirred for 1 hour and then the volatiles were removed in vacuo. The resulting residue was treated with methanol (15 ml) forming an orange suspension. A solution of sodium methoxide (25% in methanol) was added slowly via syringe. The reaction became a dark orange solution. After 1.5 hours the reaction was quenched by the slow addition of saturated ammonium chloride solution (10 ml). The methanol was removed in vacuo. The aqueous residue was extracted with dichloromethane (3×10 ml) and the organic fractions were combined and washed with water (10 ml) and brine (10 ml). The solution was dried ($Na_2SO_4$), filtered and concentrated in vacuo to yield the crude product as an orange solid. Recrystallization from propyl acetate provided 0.78 g of 2-(2-methoxyethyl)-1-[2-(prop-2-ynyloxy)ethyl]-1H-imidazo[4,5-c]quinolin-4-amine as off-white crystals.

$^1$H NMR (300 MHz, DMSO-d6) δ 8.05 (d, J=7.3 Hz, 1H), 7.61 (d, J=7.2 Hz, 1H), 7.42 (t, J=7.8 Hz, 1H), 7.23 (t, J=7.3 Hz, 1H), 6.44 (bs, 2H), 4.78 (t, J=5.2 Hz, 2H), 4.11 (d, J=2.5 Hz, 2H), 3.91 (t, J=5.5 Hz, 2H), 3.83 (t, J=6.7 Hz, 2H), 3.37 (t, J=2.6 Hz, 1H), 3.30 (s, 3H), 3.20 (t, J=6.8 Hz, 2H);

MS (CI) m/e 325 (M+H);

Anal calcd for $C_{18}H_{20}N_4O_2$: C, 66.65; H, 6.21; N, 17.27. Found: C, 66.34; H, 6.05; N, 16.96.

Example 145

2-methyl-1-(2-{[(2E)-3-phenylprop-2-enyl]oxy}ethyl)-1H-imidazo[4,5-c]quinolin-4-amine

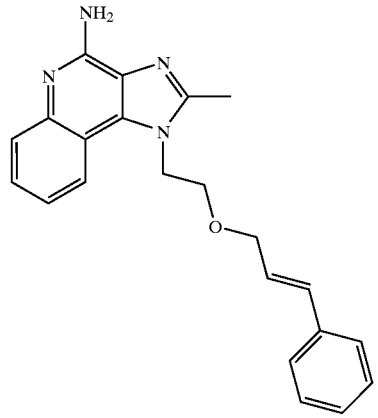

Part A

Using the general method of Example 1 Part B, 2-(2-methyl-1H-imidazo[4,5-c]quinolin-1-yl)ethyl acetate (12.0 g, 44.56 mmol) was oxidized to provide 8.7 g of 2-(2-methyl-5-oxido-1H-imidazo[4,5-c]quinolin-1-yl)ethyl acetate as a brown solid. Material was used without further purification.

Part B

A dried round bottom flask was charged with a stir bar, 2-(2-methyl-5-oxido-1H-imidazo[4,5-c]quinolin-1-yl)ethyl acetate (8.7 g, 30.49 mmol), anhydrous dimethylformamide (80 mL), and anhydrous toluene (100 mL) under nitrogen. To this brown mixture was added phosphorus oxychloride (3.1 mL) by syringe at ambient temperature. The reaction solution cleared in a couple of minutes and a slight exotherm was observed. The reaction was judged to be complete after 30 minutes. The volatiles were removed under reduced pressure. The resulting brown solid was partitioned between dichloromethane and 4% aqueous sodium bicarbonate to a pH of 8. The aqueous layer was extracted with dichloromethane (5×). The organic fractions were combined, dried with anhydrous sodium sulfate, concentrated under reduced pressure and dried overnight at ambient temperature under reduced pressure to provide 9.2 g of 2-(4-chloro-2-methyl-1H-imidazo[4,5-c]quinolin-1-yl)ethyl acetate as a brown oil.

MS (CI) for $C_{15}H_{14}ClN_3O_2$ m/z 304 (MH$^+$), 262, 218

Part C

A round bottom flask was charge with a stir bar, 2-(4-chloro-2-methyl-1H-imidazo[4,5-c]quinolin-1-yl)ethyl acetate (9.2 g, 30.5 mmol), methanol (200 mL) and potassium carbonate (0.4 g, 3.0 mmol). The reaction was judged complete after stirring for 5 hours at 26° C. The solution was partitioned between chloroform and brine. The organic layer was removed and the aqueous fraction extracted with chloroform (6×). The organic fractions were combined, dried with anhydrous sodium sulfate and concentrated under reduced pressure to approximately 200 mL when crystallization was observed. The solution was stoppered and maintained at ambient temperature for 24 hours. The resulting fine white crystals were collected by filtration to provide 4.49 g of 2-(4-chloro-2-methyl-1H-imidazo[4,5-c]quinolin-1-yl)ethanol.

MS (CI) for $C_{13}H_{12}ClN_3O$ m/z 262 (MH$^+$), 218

Part D

A round bottom flask was charge with a stir bar, 2-(4-chloro-2-methyl-1H-imidazo[4,5-c]quinolin-1-yl)ethanol (3.9 g, 14.9 mmol), dichloromethane (125 mL), aqueous sodium hydroxide (50%, 125 mL), benzyltrimethylammonium chloride (0.55 g, 0.003 mmol) and stirred vigorously at ambient temperature. To this mixture was added cinnamyl bromide (8.8 g, 44.71 mmol) as a solid. After 45 minutes the solution was clear and the reaction was judged complete. The solution was poured into ice water (200 mL), the organic layer separated and was drawn off. The aqueous solution was extracted with dichloromethane (4×). The organic layers were combined, washed with brine, dried with anhydrous sodium sulfate, and concentrated under reduced pressure. The resulting orange oil was purified by chromatography over silica gel (dichloromethane, followed by 98/2 dichloromethane/methanol). The resulting oil was triturated with ethyl ether and the resulting solid was collected by filtration and dried to provide 4.22 g of 4-chloro-2-methyl-1-(2-{[(2E)-3-phenylprop-2-enyl]oxy}ethyl)-1H-imidazo[4,5-c]quinoline as a white solid.

MS (CI) for $C_{22}H_{20}ClN_3O$ m/z 378 (MH$^+$), 262, 228

Part E

4-Chloro-2-methyl-1-(2-{[(2E)-3-phenylprop-2-enyl]oxy}ethyl)-1H-imidazo[4,5-c]quinoline (2.12 g, 5.61 mmol), was combined with an ammonia/methanol solution (7%, 70 mL) in a bomb and heated to 150° C. for 16.5 hours and cooled to ambient temperature. Analysis indicated that the reaction was incomplete. The solution was concentrated under reduced pressure to ~10 mL, diluted with ammonia/methanol (7%, 50 mL) and reacted in a bomb at 150° C. for 8.5 hours to complete the reaction. The solution was partitioned between dichloromethane and saturated aqueous sodium bicarbonate and the organic layer removed. The aqueous layer was saturated with sodium chloride and extracted with dichloromethane (3×). The organic fractions were combined, dried with anhydrous sodium sulfate and concentrated under reduced pressure. The resulting brown solid was recrystalized from methanol to provide 0.963 g of 2-methyl-1-(2-{[(2E)-3-phenylprop-2-enyl]oxy}ethyl)-1H-imidazo[4,5-c]quinolin-4-amine as a white solid, m.p. 111.8–112.5° C.

Analysis. Calculated for $C_{22}H_{22}N_4O$: % C, 73.72; % H, 6.19; % N, 15.63. Found: % C, 73.48; % H, 6.25; % N, 15.57

$^1$H NMR (300 MHz, DMSO-d6) δ 8.08 (d, J=7.5 Hz, 1H), 7.61 (d, J=8.1 Hz, 1H), 7.40 (t, J=5.6 Hz, 1H), 7.18–7.30 (m, 6H), 6.51 (s, 2H), 6.31 (d, J=16.2 Hz, 1H), 617 (dt, J=15.6, 5.3 Hz, 1H), 4.76 (t, J=5.0 Hz, 2H), 4.05 (d, J=3.9 Hz, 2H), 3.91 (t, J=5.6, 2H), 2.64 (s, 3H)

MS (CI) for $C_{22}H_{22}N_4O$ m/z 259 (MH$^+$), 243, 199

Example 146

2-methyl-1-{2-[(3-phenylprop-2-ynyl)oxy]ethyl}-6,7,8,9-tetrahydro-1H-imidazo[4,5-c]quinolin-4-amine

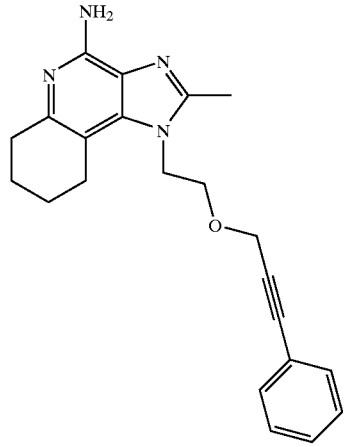

Part A

Using the general method of Example 115 Part C, the 4-amino group was introduced to 2-(2-methyl-5-oxido-1H-imidazo[4,5-c]quinolin-1-yl)ethyl acetate (8.47 g, 29.71 mmol). The resulting brown oil was purified by trituration with acetonitrile and dried to yield 3.583 g of 2-(4-amino-2-methyl-1H-imidazo[4,5-c]quinolin-1-yl)ethyl acetate as a tan solid.

MS (CI) for $C_{15}H_{16}ClN_4O_2$ m/z 285 (MH$^+$), 270, 199

Part B

A Parr flask was charged with 2-(4-amino-2-methyl-1H-imidazo[4,5-c]quinolin-1-yl)ethyl acetate (3.61 g, 12.64 mmol), trifluoroacetic acid (50 mL) and purged with nitrogen. To this solution was added platinum(IV) oxide (0.5 g). The reaction was judged to be complete after 13 days of hydrogenation at ambient temperature. The solution was filtered and the volatiles removed under reduced pressure. The resulting brown oil was partitioned between dichloromethane and saturated aqueous sodium bicarbonate to a pH of ~8. The layers were separated. The aqueous layer was extracted with dichloromethane (4×). The organic fractions were combined, dried with anhydrous sodium sulfate and concentrated under reduced pressure. The resulting white solid was purified by recrystallization from ethyl acetate/methanol (9/1) and dried to provide 0.98 g of 2-(4-amino-2-methyl-6,7,8,9-tetrahydro-1H-imidazo[4,5-c]quinolin-1-yl)ethanol as a white solid.

MS (CI) for $C_{13}H_{18}N_4O$ m/z 247 (MH$^+$), 203

Part C

Using the general method of Example 1 Part A, 2-(4-amino-2-methyl-6,7,8,9-tetrahydro-1H-imidazo[4,5-c]quinolin-1-yl)ethanol (0.763 g, 3.098 mmol) was reacted with propargyl bromide (80% in toluene, 1.1 mL, 9.29 mmol) to provide 0.42 g of 2-methyl-1-[2-(prop-2-ynyloxy)ethyl]-6,7,8,9-tetrahydro-1H-imidazo[4,5-c]quinolin-4-amine as a brown oil.

MS (CI) for $C_{16}H_{20}N_4O$ m/z 285 (MH$^+$), 247, 183

Part D

Using the general method of Example 12 Part A, 2-methyl-1-[2-(prop-2-ynyloxy)ethyl]-6,7,8,9-tetrahydro-1H-imidazo[4,5-c]quinolin-4-amine (0.396 g, 1.392 mmol) was reacted with iodobenzene (0.17 mL, 1.532 mmol) at ambient temperature. After 18 hours the reaction was incomplete. The solution was heated to 50° C. for 3 hours to complete the reaction. The volatiles were removed under reduced pressure. The resulting oil was partitioned between dichloromethane and 4% aqueous sodium carbonate and the organic layer removed. The aqueous layer was extracted with dichloromethane (3×). The organic fractions were combined, dried with anhydrous sodium sulfate and the volatiles were removed under reduced pressure. The resulting oil was purified by chromatography over silica gel (95/5 dichloromethane/methanol). The resulting white solid was dissolved in dichloromethane (2 mL) and reacted with 1M HCl in ether (2 mL). The volatiles were removed under reduced pressure and the resulting solids recrystallized from methanol to provide 0.1089 g of 2-methyl-1-{2-[(3-phenylprop-2-ynyl)oxy]ethyl}-6,7,8,9-tetrahydro-1H-imidazo[4,5-c]quinolin-4-amine(hydrochloride)$_{1.9}$ as a tan solid.

Analysis. Calculated for $C_{22}H_{24}N_4O$ (HCl)$_{1.9}$ (H$_2$O)$_{0.7}$: % C, 59.74; % H, 6.22; % N, 12.67; % Cl, 15.23. Found: % C, 59.72; % H, 6.04; % N, 12.65; % Cl, 14.99

$^1$H NMR (300 MHz, DMSO-d6) δ 7.93 (s, 2H), 7.36–7.40 (m, 3H), 7.28–7.30 (m, 2H), 4.56 (t, J=5.0 Hz, 2H), 4.35 (s, 2H), 3.88 (t, J=5.3 Hz, 2H), 2.92 (s, 2H), 2.69 (s, 2H), 2.60 (s, 3H), 1.73 (s, 4H)

MS (CI) for $C_{22}H_{24}N_4O$ m/z 361 (MH$^+$), 247, 199

Example 147

2-Methyl-1-{3-[(3-phenylprop-2-ynyl)oxy]propyl}-H-imidazo[4,5-c]quinolin-4-amine

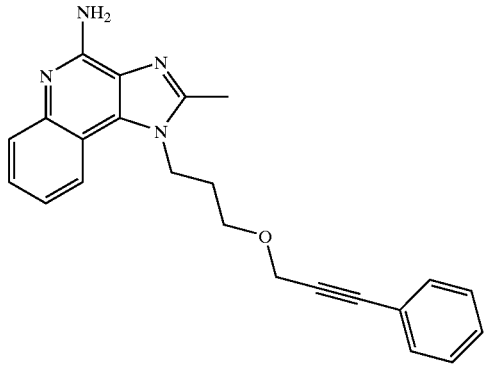

Part A 3-(2-Methyl-1H-imidazo[4,5-c]quinolin-1-yl)propyl (Prop-2-ynyl) Ether

To 3-(2-methyl-1H-imidazo[4,5-c]quinolin-1-yl)-1-propanol (12.2 g, 50.56 mmol) dissolved in dichloromethane (180 mL) was added sodium hydroxide (180 mL of 50%) with mechanical stirring. Benzyltrimethylammonium chloride (1.88 g, 10.11 mmol) was added to the resulting suspension, and after stirring for 5 minutes, propargyl bromide (17 mL of 80% in toluene, 141.8 mmol) was added. The resulting reaction mixture was allowed to stir at ambient temperature. After 2 hours, TLC monitoring indicated 50% completion, and after 4.5 hours HPLC monitoring indicated 20% starting material remaining. More propargyl bromide (5 mL of 80% in toluene, 40.51 mmol) was added, and the resulting reaction mixture was allowed to stir at ambient temperature for 64.5 hours. The layers were separated, and the organic layer was washed with water (3×) and brine, dried over sodium sulfate, filtered, and concentrated under reduced pressure. The resulting dark oil was dissolved in dichloromethane and again extracted with water, dried over sodium sulfate, and concentrated under reduced pressure. The resulting dark oil was purified by silica gel column chromatography using 98/2 dichloromethane/methanol as the eluant. After removing the solvent from the collected fractions, 5.880 g of pure (by HNMR analysis) product was obtained. This material was recrystallized from ethyl acetate/hexane to provide 4.658 g of brown crystals.

Part B 3-(2-Methyl-1H-imidazo[4,5-c]quinolin-1-yl)propyl (3-Phenylprop-2-ynyl) Ether Under a nitrogen atmosphere, a mixture of 3-(2-methyl-1H-Imidazo[4,5-c]quinolin-1-yl)propyl(prop-2-ynyl) ether (4.6585 g, 16.68 mmol) from Part A, anhydrous acetonitrile (60 mL), anhydrous triethylamine (6 mL, 43.37 mmol), and iodobenzene (2.1 mL, 18.34 mmol) was heated to 80° C. with stirring. Dichlorobis(triphenylphosphine)palladium(II) (0.23 g, 0.334 mmol), and copper(I) iodide (0.13 g, 0.667 mmol) were added and the mixture was allowed to stir for 0.5 hour. Analysis by HPLC indicated that the reaction was complete. The reaction mixture was concentrated under reduced pressure, and the concentrate was purified by column chromatography over silica gel, employing dichloromethane (1 L) and 98/2 dichloromethane/methanol as the eluants. The resulting green oil (5.1 g) was triturated with ether, but no solids formed. The oil was placed under high vacuum (4 torr) at room temperature. HNMR analysis of the resulting oil showed the presence of ether. The oil was further dried under high vacuum to provide 4.7 g of dark oil.

Part C

2-Methyl-1-[3-(3-phenylprop-2-ynyloxy)propyl-1H-imidazo[4,5-c]quinoline-5N-oxide 3-(2-Methyl-1H-imidazo[4,5-c]quinolin-1-yl)propyl(3-phenylprop-2-ynyl) ether (4.7 g, 13.22 mmol) and dichloromethane were combined, and 3-chloroperoxybenzoic acid (4.87 g of dry material) was added in a single portion. After the mixture was stirred for 40 minutes, TLC analysis using 9/1 dichloromethane/methanol indicated that the reaction was complete. This was confirmed by HPLC and HNMR analyses. The product, 2-methyl-1-[3-(3-phenylprop-2-ynyloxy)propyl]-1H-imidazo[4,5-c]quinoline-5N-oxide, was confirmed by HPLC and LC-MS. The resulting solution was used as is in the next step.

Part D

2-Methyl-1-{3-[(3-phenylprop-2-ynyl)oxy]propyl}-1H-imidazo[4,5-c]quinolin-4-amine To the solution from Part C was added ammonium hydroxide (50 mL) with vigorous stirring. p-Toluenesulfonyl chloride (2.77 g, 14.54 mmol) was added as a dry solid to the resulting solution over a 2 minute period to prevent excessive foaming. After 40 minutes, the reaction was judged to be complete by TLC analysis using 9/1 dichloromethane/methanol. The resulting reaction mixture was diluted with water and extracted with dichloromethane. The combined organic layers were washed with brine, dried over sodium sulfate, and filtered. The resulting filtrate was concentrated under reduced pressure to provide 4.9 g of brown solid, which was purified by column chromatography over silica gel using dichloromethane (1 L) and 95/5 dichloromethane/methanol as the eluants. A brown oil (3.8 g) was isolated and triturated with acetonitrile, causing a solid to form after 30 minutes. The solid was collected by filtration, and washed with ether. HNMR analysis of the resulting solid was consistent with the desired product that contained residual acetonitrile and ether. The solid was dried to provide 2.308 g of 2-methyl-1-{3-[(3-phenylprop-2-ynyl)oxy]propyl}-1H-imidazo[4,5-c]quinolin-4-amine, m.p. 160.0–161.6° C.

Analysis: Calculated for $C_{23}H_{22}N_4O$: % C, 74.57; % H, 5.99; % N, 15.12. Found: % C, 74.27; % H, 5.94; % N, 15.10

$^1$H NMR (300 MHz, DMSO-d6) δ 8.12 (d, J=8.1 Hz, 1H), 7.61 (d, J=7.5 Hz, 1H), 7.38–7.47 (m, 6H), 7.24 (t, J=6.9 Hz, 1H), 6.53 (s, 2H), 4.60 (t, J=7.2 Hz, 2H), 4.45 (s, 2H), 3.60 (t, J=5.6 Hz, 2H), 2.63 (s, 3H), 2.14 (p, J=6.5 Hz, 2H).

Example 148

2-Methyl-1-[3-(3-phenylpropoxy)propyl]-1H-imidazo[4,5-c]quinolin-4-amine

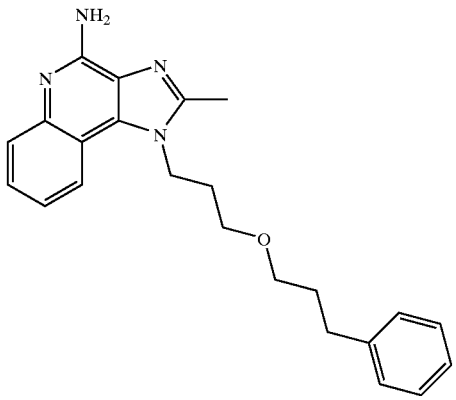

2-Methyl-1-{3-[(3-phenylprop-2-ynyl)oxy]propyl}-1H-imidazo[4,5-c]quinolin-4-amine (1.4 g, 3.779 mmol) was combined with toluene (15 mL) in a Parr flask and heated to reflux. The resulting solution was cooled to room temperature and purged with nitrogen. Palladium (0.6 g 10% palladium on carbon) was added to the solution under nitrogen, and the flask was pressurized with hydrogen at 310 kPa for 2.75 hours. Monitoring by HNMR indicated incomplete reaction. More 10% palladium on carbon (0.16 g) was added, and after an additional 2.5 hours at 310 kPA of hydrogen, the reaction was determined to be complete. The catalyst was filtered off, and the volatiles were removed under reduced pressure. The resulting white solid was recrystallized from acetonitrile and dried for 5 days to provide 1.0723 g of 2-methyl-1-[3-(3-phenylpropoxy)propyl]-1H-imidazo[4,5-c]quinolin-4-amine, m.p. 145.0–146.1° C.

Analysis: Calculated for $C_{23}H_{26}N_4O$: % C, 73.77; % H, 7.00; % N, 14.96. Found: % C, 73.50; % H, 6.92; % N, 14.86

$^1$H NMR (300 MHz, DMSO-d6) δ 8.16 (d, J=8.1 Hz, 1H), 7.60 (d, J=10.0 Hz, 1H), 7.40 (t, J=7.4 Hz, 1H), 7.15–7.31 (m, 6H), 6.49 (s, 2H), 4.58 (t, J=7.5 Hz, 2H), 3.39–3.47 (m, 4H), 2.67 (t, J=7.8 Hz, 2H), 2.60 (s, 3H), 2.08 (p, J=6.2 Hz, 2H), 1.86 (p, J=7.0 Hz, 2H).

Example 149

2-Methyl-1-{4-[(3-phenylprop-2-ynyl)oxy]butyl}-1H-imidazo[4,5-c]quinolin-4-amine

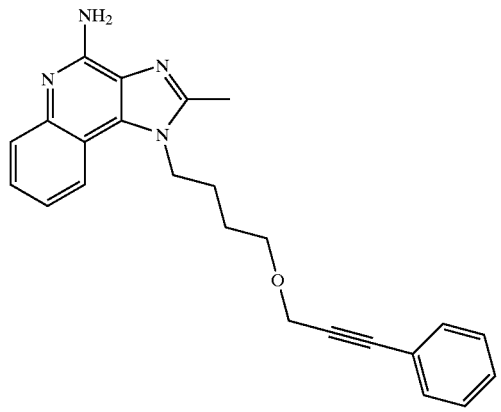

Part A 4-(2-methyl-1H-imidazo[4,5-c]quinolin-1-yl)butyl (Prop-2-ynyl) Ether

To 4-(2-methyl-1H-imidazo[4,5-c]quinolin-1-yl)-1-butanol (1 g, 3.917 mmol), dichloromethane (14 mL), sodium hydroxide (14 mL of 50%), and benzyltrimethylammonium chloride (0.15 g, 0.783 mmol) were combined with stirring. Propargyl bromide (1.3 mL of 80% in toluene, 11.75 mmol) was added to the resulting mixture at ambient temperature. After the resulting reaction mixture was allowed to stir at ambient temperature for 1 hour, TLC analysis using 9/1 dichloromethane/methanol indicated incomplete reaction. After 18 hours HPLC monitoring indicated complete reaction. The two reaction layers were separated. The organic layer was washed with water (3×100 mL). All aqueous layers were combined and extracted with dichloromethane (3×100 mL). All organic layers were combined and washed with brine (3×100 mL). The brine layers were combined and extracted with dichloromethane (3×100 mL). All resulting organic layers were combined, dried with sodium sulfate, filtered, and concentrated under reduced pressure. HNMR analysis of the resulting dark oil was consistent with the desired product and some residual solvent. HPLC and LC/MS were consistent with the desired product (1.1 g) that was of sufficient purity for use in the next step.

Part B 4-(2-Methyl-1H-imidazo[4,5-c]quinolin-1-yl)butyl (3-Phenylprop-2-ynyl) Ether 4-(2-Methyl-1H-Imidazo[4,5-c]quinolin-1-yl)butyl(prop-2-ynyl) ether (1.1 g, 3.75 mmol) from Part A, anhydrous acetonitrile (10 mL), anhydrous triethylamine (1.4 mL, 9.75 mmol), and iodobenzene (0.5 mL, 4.12 mmol) were combined and heated to 80° C. Dichlorobis(triphenylphosphine)palladium(II) (0.05 g, 0.07 mmol), and copper(I) iodide (0.03 g, 0.15 mmol) were added to the resulting solution, and the mixture was allowed to stir for 0.5 hour. Analysis by HPLC indicated that the reaction was complete. The resulting reaction mixture was allowed to cool to ambient temperature, and filtered. The filtrate, which still contained a fine precipitate, was plug filtered through a silica gel column using dichloromethane and 98/2 dichloromethane/methanol as the eluants. Two fractions were collected, and, after removing the volatiles under reduced pressure, an oil was isolated from each. The oils were dried separately under high vacuum to provide 0.4525 g of a first oil and 0.2506 g of a second oil. HNMR analysis of the first oil indicated residual methanol and of the second oil showed residual iodobenzene and ethyl acetate. The two oils were carried on separately to the next step.

Part C

2-Methyl-1-[4-(3-phenylprop-2-ynyloxy)butyl]-1H-imidazo[4,5-c]quinoline-5N-oxide The first oil from Part B, 4-(2-Methyl-1H-imidazo[4,5-c]quinolin-1-yl)butyl(3-phenylprop-2-ynyl) ether (0.4525 g, 1.225 mmol) and dichloromethane (5 mL) were combined, and then 3-chloroperoxybenzoic acid (0.45 g of 75%, 1.959 mmol) was added. After the resulting mixture was stirred for 1 hour, HNMR analysis indicated that the reaction was complete. The reaction mixture was extracted with saturated aqueous potassium carbonate. The resulting aqueous layer was extracted with dichloromethane. All organic layers were combined, washed with brine, dried over sodium sulfate, filtered, and concentrated under reduced pressure to provide 0.6068 g of undried product, 2-methyl-1-[4-(3-phenylprop-2-ynyloxy)butyl]-1H-imidazo[4,5-c]quinoline-5N-oxide. This was confirmed by HNMR. The resulting solution was used in the next step without further purification.

The above procedure was repeated using the second oil (0.2506 g) from Part B, and 0.25 g of the 3-chloroperoxybenzoic acid to provide 0.3749 g of undried product.

Part D

2-Methyl-1-{4-[(3-phenylprop-2-ynyl)oxy]butyl}-1H-Imidazo[4,5-c]quinolin-4-amine To 2-methyl-1-[4-(3-phenylprop-2-ynyloxy)butyl]-1H-imidazo[4,5-c]quinoline-5N-oxide (9.2 g, 23.87 mmol) dissolved in dichloromethane (50 mL) was added ammonium hydroxide (25 mL of 27%) with vigorous stirring in a 1 L flask (for sufficient head room for foaming). p-Toluenesulfonyl chloride (5.00 g, 26.25 mmol) was added in a single portion to the resulting solution, and foaming occured. After stirring at ambient temperature for 20 minutes, the reaction was judged to be complete by TLC, HPLC, and LC/MS. The resulting reaction mixture was mixed with 1N potassium hydroxide. Brine was added to the resulting emulsion, and the organic layer separated from the aqueous layer. The aqueous layer was washed with dichloromethane (5x). All organic layers were combined, washed with brine, dried with sodium sulfate, filtered, and concentrated under reduced pressure. The resulting dark brown residue was triturated with dichloromethane/ether, and the resulting tan solid was collected by vacuum filtration and dried in a vacuum desicator for 2 days. HNMR analysis of the resulting tan solid (5.1733 g) was consistent with the desired product. A portion of this tan solid (2 g) was used in Example 150 and the remainder was recrystallized from toluene. The recrystallized material was dissolved in dichloromethane, and the resulting solution was washed with 0.1 N potassium hydroxide, water, and brine, dried with sodium sulfate, and concentrated under reduced pressure to dryness. The resulting solid was recrystallized from toluene and dried at 60° C. for 4 days under high vacuum to provide 2.0028 g of 2-methyl-1-{4-[(3-phenylprop-2-ynyl)oxy]butyl}-1H-imidazo[4,5-c]quinolin-4-amine, m.p. 109.2–110.0° C.

Analysis: Calculated for $C_{24}H_{24}N_4O$: % C, 74.97; % H, 6.29; % N, 14.57. Found: % C, 74.75; % H, 6.28; % N, 14.49

$^1$H NMR (300 MHz, DMSO-d6) δ 8.75 (d, J=8.1 Hz, 1H), 7.60 (d, J=8.1 Hz, 1H), 7.34–7.43 (m, 6H), 7.26 (t, J=7.8 Hz, 1H), 6.49 (s, 2H), 4.54 (t, J=7.5 Hz, 2H), 4.39 (s, 2H), 3.59 (t, J=6.2 Hz, 2H), 2.6 (s, 3H), 1.91 (p, J=7.5 Hz, 2H), 1.72 (p, J=6.7 Hz, 2H).

Example 150

2-Methyl-1 [4-(3-phenylpropoxy)butyl]-1H-imidazo [4,5-c]quinolin-4-amine

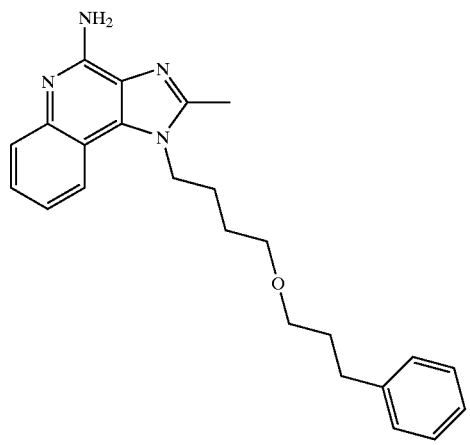

2-Methyl-1-{4-[(3-phenylprop-2-ynyl)oxy]butyl}-1H-imidazo[4,5-c]quinolin-4-amine (2.00 g, 5.202 mmol) from Example 149 was combined with toluene (15 mL) in a Parr flask and heated to reflux. The resulting solution was purged with nitrogen. Palladium (1 g 10% palladium on carbon) was added to the solution under nitrogen, and the flask was pressurized with hydrogen at 310 kPa for 3 hours. Monitoring by HNMR indicated complete reaction. The catalyst was filtered off, and the filtrate was concentrated under reduced pressure. The concentrate was dissolved in dichloromethane and basified with 1 N potassium hydroxide to a pH of about 14. The layers were separated and the aqueous layer was extracted with dichloromethane (3x). The organic layers were combined, washed with 0.5 N potassium hydroxide (2x), water (3x), and brine (3x), dried with sodium sulfate, filtered, and concentrated under reduced pressure. The resulting solid was recrystallized from acetonitrile, and the resulting shinny tan crystals were dried for 2 days, triturated with ether, collected by vacuum filtration, and dried to provide 0.5744 g of 2-methyl-1 [4-(3-phenylpropoxy)butyl]-1H-imidazo[4,5-c]quinolin-4-amine, m.p. 105.1–106.0° C.

Analysis: Calculated for $C_{24}H_{28}N_4O$: % C, 74.20; % H, 7.26; % N, 14.42. Found: % C, 73.88; % H, 7.33; % N, 14.06

$^1$H NMR (300 MHz, DMSO-d6) δ 8.05 (d, J=8.1 Hz, 1H), 7.60 (d, J=6.9 Hz, 1H), 7.40 (t, J=7.2 Hz, 1H), 7.12–7.26 (m, 6H), 6.50 (s, 2H), 4.52 (t, J=7.5 Hz, 2H), 3.41 (t, J=5.9 Hz, 2H), 3.35 (t, J=6.2 Hz, 2H), 2.54–2.60 (m, 5H), 1.89 (p, J=7.4 Hz, 2H), 1.76 (p, J=7.0 Hz, 2H), 1.65 (p, J=6.6 Hz, 2H).

Cytokine Induction in Human Cells

An in vitro human blood cell system is used to assess cytokine induction. Activity is based on the measurement of interferon and tumor necrosis factor (α) (IFN and TNF, respectively) secreted into culture media as described by Testerman et. al. In "Cytokine Induction by the Immunomodulators Imiquimod and S-27609", Journal of Leukocyte Biology, 58, 365–372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using Histopaque®-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at 4×10⁶ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30–0.014 $\mu$M.

Incubation

The solution of test compound is added at 60 $\mu$M to the first well containing RPMI complete and serial 3 fold dilutions are made in the wells. The PBMC suspension is then added to the wells in an equal volume, bringing the test compound concentrations to the desired range (30–0.014 $\mu$M). The final concentration of PBMC suspension is 2×10⁶ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (~200×g) at 4° C. The cell-free culture supernatant is removed with a sterile polypropylene pipet and transferred to sterile polypropylene tubes. Samples are maintained at −30 to −70° C. until analysis. The samples are analyzed for interferon ($\alpha$) by ELISA and for tumor necrosis factor ($\alpha$) by ELISA or IGEN Assay.

Interferon ($\alpha$) and Tumor Necrosis Factor ($\alpha$) Analysis by ELISA

Interferon ($\alpha$) concentration is determined by ELISA using a Human Multi-Species kit from PBL Biomedical Laboratories, New Brunswick, N.J. Results are expressed in pg/mL.

Tumor necrosis factor ($\alpha$) (TNF) concentration is determined using ELISA kits available from Biosource International, Camarillo, Calif. Alternately, the TNF concentration can be determined by Origen® M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

The table below lists the lowest concentration found to induce interferon and the lowest concentration found to induce tumor necrosis factor for each compound. A "*" indicates that no induction was seen at any of the tested concentrations; generally the highest concentration tested was 10 or 30 $\mu$M.

| | Cytokine Induction in Human Cells | |
|---|---|---|
| Example | Lowest Effective Concentration ($\mu$M) | |
| Number | Interferon | Tumor Necrosis Factor |
| 1 | 0.12 | 1.11 |
| 2 | 1.11 | * |
| 3 | 0.12 | 3.33 |
| 4 | 0.12 | * |
| 5 | 0.12 | 1.11 |
| 6 | 0.12 | * |
| 7 | 1.11 | 0.37 |
| 8 | 1.11 | 10 |
| 9 | * | * |
| 10 | 1.11 | 10 |
| 11 | 1.11 | * |
| 12 | 10 | * |
| 13 | 10 | 10 |
| 14 | 10 | 10 |
| 15 | 0.12 | * |
| 16 | 0.01 | 0.37 |
| 17 | 0.12 | 0.37 |
| 18 | 0.12 | 1.11 |
| 19 | 0.37 | * |
| 20 | * | * |
| 21 | 0.12 | * |
| 22 | 0.12 | 0.37 |
| 23 | 1.11 | * |
| 24 | 0.12 | * |
| 25 | 0.12 | * |
| 26 | 0.12 | * |
| 27 | 0.12 | * |
| 28 | 10 | * |
| 29 | * | * |
| 30 | 3.33 | * |
| 31 | * | * |
| 32 | 10 | * |
| 33 | * | * |
| 34 | * | * |
| 35 | * | * |
| 36 | * | * |
| 37 | * | * |
| 38 | 10 | * |
| 39 | 1.11 | * |
| 40 | 0.12 | * |
| 41 | 1.11 | 3.33 |
| 42 | 0.37 | * |
| 43 | 0.37 | * |
| 45 | 0.37 | * |
| 46 | 0.01 | 3.33 |
| 47 | 0.12 | * |
| 48 | 0.12 | * |
| 49 | 0.04 | * |
| 50 | 3.33 | * |
| 51 | 0.37 | * |
| 52 | 1.11 | * |
| 53 | 1.11 | * |
| 54 | 0.12 | * |
| 55 | * | * |
| 56 | 1.11 | 10 |
| 57 | * | 30 |
| 58 | 3.33 | * |
| 59 | 1.11 | * |
| 60 | 1.11 | * |
| 61 | 3.33 | * |
| 62 | * | 3.33 |
| 63 | * | * |
| 64 | 3.33 | * |
| 65 | 1.11 | * |
| 66 | * | * |
| 67 | * | 30 |
| 68 | 3.33 | * |
| 69 | 1.11 | * |
| 70 | 0.37 | * |
| 71 | 3.33 | * |
| 72 | 1.11 | * |
| 73 | 1.11 | * |
| 74 | 0.37 | * |

-continued

Cytokine Induction in Human Cells

| Example Number | Lowest Effective Concentration (µM) | |
|---|---|---|
| | Interferon | Tumor Necrosis Factor |
| 75 | * | * |
| 76 | 1.11 | * |
| 77 | 0.12 | * |
| 78 | * | * |
| 79 | * | * |
| 80 | * | * |
| 81 | 1.11 | * |
| 82 | * | * |
| 83 | 0.37 | * |
| 84 | 0.37 | * |
| 85 | 0.37 | * |
| 86 | 0.37 | * |
| 87 | 1.11 | * |
| 88 | 0.37 | 30 |
| 89 | 0.37 | 10 |
| 90 | 0.12 | 10 |
| 91 | 0.37 | 10 |
| 92 | 3.33 | 3.33 |
| 93 | 0.12 | 10 |
| 94 | 0.01 | 3.33 |
| 95 | 1.11 | * |
| 96 | 0.12 | 10 |
| 97 | 1.11 | * |
| 98 | 0.37 | * |
| 99 | 0.37 | * |
| 100 | * | * |
| 101 | 0.04 | 10 |
| 102 | 0.37 | * |
| 103 | * | 10 |
| 104 | 0.12 | 10 |
| 105 | 0.37 | 1.11 |
| 106 | 0.37 | * |
| 108 | 0.00017 | 0.04 |
| 109 | 0.01 | 0.37 |
| 110 | 3.33 | * |
| 111 | 3.33 | * |
| 112 | * | * |
| 113 | 1.11 | * |
| 114 | 0.12 | 0.37 |
| 115 | 0.12 | 1.11 |
| 116 | * | * |
| 117 | * | * |
| 118 | 0.01 | 0.04 |
| 119 | 0.01 | 0.12 |
| 120 | 0.01 | 0.01 |
| 121 | 0.01 | 0.04 |
| 122 | 0.01 | 0.12 |
| 123 | 0.12 | 10 |
| 124 | 1.11 | 10 |
| 125 | 0.01 | 0.37 |
| 126 | 0.04 | 0.04 |
| 127 | 0.01 | 0.12 |
| 128 | * | * |
| 129 | 0.01 | 0.04 |
| 130 | 3.33 | 3.33 |
| 131 | * | 10 |
| 132 | 0.01 | 3.33 |
| 133 | 3.33 | * |
| 134 | * | * |
| 135 | * | * |
| 138 | 1.11 | * |
| 139 | * | * |
| 140 | * | * |
| 141 | 0.12 | 0.12 |
| 142 | 0.04 | 0.04 |
| 143 | 1.11 | 3.33 |
| 144 | 0.01 | 0.04 |
| 147 | 0.37 | 0.37 |
| 148 | 1.11 | 1.11 |
| 149 | 0.041 | 0.37 |
| 150 | 0.37 | 1.11 |

What is claimed is:

1. A pharmaceutical composition comprising a therapeutically effective amount of a compound of the formula (IV):

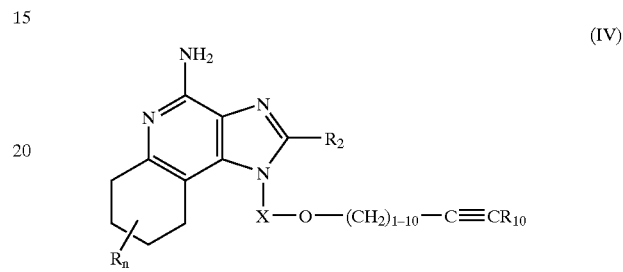

(IV)

wherein: X is —CHR$_3$—, —CHR$_3$-alkyl-, or —CHR$_3$-alkenyl-;

R$_{10}$ is selected from the group consisting of:
- —H;
- -alkyl;
- -alkenyl; and
- -aryl;

R$_2$ is selected from the group consisting of:
- -hydrogen;
- -alkenyl;
- -aryl;
- -heteroaryl;
- -heterocyclyl;
- -alkyl-Y-alkyl;
- -alkyl-Y-aryl;
- -alkyl-Y-alkenyl; and
- -alkyl or alkenyl substituted by one or more substituents selected from the group consisting of:
  - —OH;
  - -halogen;
  - —N(R$_3$)$_2$;
  - —CO—C$_{1-10}$ alkyl;
  - —CO—O—C$_{1-10}$ alkyl;
  - —N$_3$;
  - -aryl;
  - -heteroaryl;
  - -heterocyclyl;
  - —CO-aryl; and
  - —CO-heteroaryl;

each R$_3$ is independently H or C$_{1-10}$ alkyl;

Y is —O— or —S(O)$_{0-2}$—;

n is 0; and each R present is independently selected from the group consisting of C$_{1-10}$ alkyl, C$_{1-10}$ alkoxy, hydroxy, halogen and trifluoromethyl;

or a pharmaceutically acceptable salt thereof, and a pharmaceutically acceptable carrier.

* * * * *